US006489440B1

(12) United States Patent
Aoki et al.

(10) Patent No.: US 6,489,440 B1
(45) Date of Patent: Dec. 3, 2002

(54) CYCLIC COMPOUNDS

(75) Inventors: Masahiro Aoki, Chigasaki (JP); Masami Kohchi, Fujisawa (JP); Kazunao Masubuchi, Yokohama (JP); Eisaku Mizuguchi, Kamakura (JP); Takeshi Murata, Chigasaki (JP); Hiroaki Ohkuma, Tokyo (JP); Takehiro Okada, Fujisawa (JP); Masahiro Sakaitani, Chigasaki (JP); Nobuo Shimma, Chigasaki (JP); Takahide Watanabe, Kamakura (JP); Mieko Yanagisawa, Yokohama (JP); Yuri Yasuda, Chigasaki (JP)

(73) Assignee: Basilea Pharmaceutica AG, Binningen (CH)

( * ) Notice: Subject to any disclaimer, the term of this patent is extended or adjusted under 35 U.S.C. 154(b) by 0 days.

(21) Appl. No.: 09/360,476

(22) Filed: Jul. 23, 1999

(30) Foreign Application Priority Data

| | | |
|---|---|---|
| Jul. 23, 1998 | (EP) | 98113744 |
| Apr. 16, 1999 | (EP) | 99107637 |

(51) Int. Cl.[7] .......... C07K 7/50
(52) U.S. Cl. .......... 530/317; 530/327; 530/332; 514/11; 514/14
(58) Field of Search .......... 530/317, 327, 530/332; 514/9, 11, 14

(56) References Cited

U.S. PATENT DOCUMENTS

| | | | | |
|---|---|---|---|---|
| 5,446,022 A | * | 8/1995 | Fujie | 514/11 |
| 5,547,934 A | * | 8/1996 | Fujie | 514/11 |

FOREIGN PATENT DOCUMENTS

| | | |
|---|---|---|
| EP | 584 360 | 3/1994 |
| EP | 736 541 | 10/1996 |
| WO | 96/30399 | 10/1996 |

OTHER PUBLICATIONS

Davies et al., *Tetrahedron Asymmetry 2*(*3*), pp. 183–186 (1991).

Bouffard et al., *J. Med. Chem. 37:222–225* (1994).

Black et al., *Biorg. Med. Chem. Lett 7*(*22*) pp. 2879–2884 (1997).

Futaki et al, *J. Chem. Soc. Perkins Trans.* (*6*), pp. 1739–1744 (1990).

Abstract of Japanese Patent No. 09176189 published Aug. 7, 1997.

* cited by examiner

*Primary Examiner*—Christopher S. F. Low
*Assistant Examiner*—David Lukton
(74) *Attorney, Agent, or Firm*—George W. Johnston; Dennis P. Tramaloni

(57) ABSTRACT

The present invention relates to novel Aerothricins represented by the Formula (I), (I)

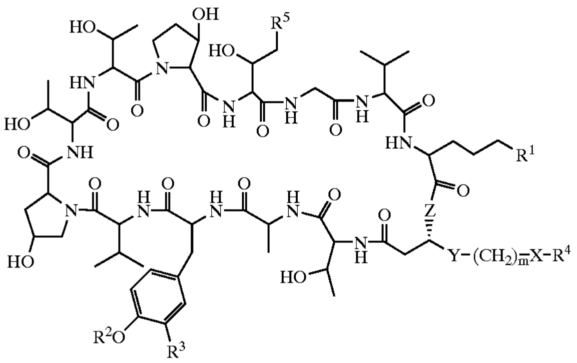

wherein $R^1$, $R^2$, $R^3$, $R^4$, $R^5$, X, Y, Z, and m are as defined in Claim 1; and pharmaceutically acceptable salts thereof.

The present invention also relates to a pharmaceutical composition comprising an Aerothricin of the Formula (I) and a pharmaceutically acceptable carrier. Furthermore, the present invention relates to the use of such Aerothricins for the preparation of medicaments, as well as to processes and intermediates for the preparation of the Aerothricins of the Formula (I).

51 Claims, 11 Drawing Sheets

CYCLIC COMPOUNDS

FIELD OF THE INVENTION

The present invention relates to novel cyclic compounds having antifungal activity (hereinafter referred to as Aerothricins), the use of Aerothricins in the medical therapy, pharmaceutical compositions containing Aerothricins as well as to processes and intermediates for the preparation of Aerothricins.

BACKGROUND

Azole antifungal agents are currently widely used for the treatment of systemic mycoses. However, long term prophylactic use of azole antifungals resulted in generation of azole resistant Candida spp. due to their fungistatic action. Therefore, fungicidal agents are particularly important for treatment of severe systemic mycoses. Furthermore, the currently available antifungal agents are not effective against Fusarium spp. which is one of the emerging pathogens among immunocompromised patients. Amphotericin B is a highly effective fungicidal agent currently used clinically, but its therapeutic index (effective dose vs. toxic dose) is rather narrow. Certain cyclic compounds such as LY303366 (EP 736 541), WF11243 (EP 584 360) are known to show fungicidal activity through inhibition of β-1,3-glucan synthase. However, they have still some disadvantages in terms of antifungal spectrum and/or safety profile. Thus, development of new fungicidal agents with better safety profile and efficacy against major systemic pathogens including newly emerging pathogens like Fusarium spp. is urgently required.

SUMMARY OF THE INVENTION

The present invention relates to novel Aerothricins represented by the Formula (I), wherein (I)

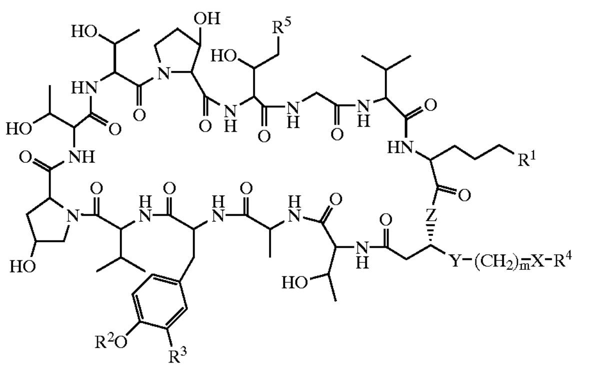

$R^1$ is guanidino, tri-lower alkylammonio, —N($R^{10}$)—$R^{11}$, —N($R^{15}$)—CO—$R^{14}$, —N($R^{15}$)—CO—CH[N($R^{10}$)$R^{11}$]—$R^{13}$, —NHCOCH($R^{13}$)—NHCOCH($NH_2$)—$R^{13}$,

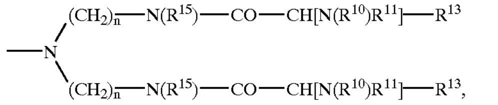

-continued

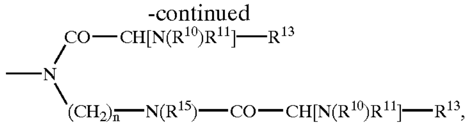

or

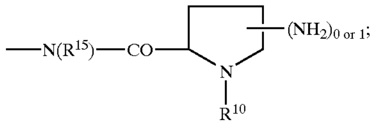

$R^{10}$ and $R^{11}$ are each independently selected from hydrogen; heteroaryl substituted with one or two amino; lower alkyl optionally substituted with one or more, preferably one or two, amino, amino-lower alkyl, cyano, guanidino, nitrogen containing heterocycle(s) or phenyl group(s) containing an amino, amidino or guanidino group;

$R^{13}$ is a residue derived from natural or unnatural amino acids;

$R^{14}$ is lower alkyl substituted with one or more, preferably one or two, amino, guanidino, nitrogen containing heterocycle(s) or phenyl group(s) containing an amino, amidino or guanidino group;

$R^{15}$ is hydrogen, lower alkyl optionally substituted with one or more, preferably one or two, amino, guanidino, nitrogen containing heterocycle(s) or phenyl group(s) containing an amino, amidino or guanidino group;

$R^2$ is hydrogen, hydroxysulfonyl, lower alkyl or lower alkenyl, wherein lower alkyl and lower alkenyl may be optionally substituted with acyl, carbamoyl, amino, mono-lower alkylamino or di-lower alkylamino;

$R^3$ is hydrogen, hydroxy, nitro, amino, acylamino, (lower alkylcarbamoyl)amino, carboxyl, lower alkoxy, lower alkoxycarbonyl, lower alkyl, lower alkenyl or lower alkynyl, wherein lower alkyl, lower alkenyl and lower alkynyl may be optionally substituted with hydroxy, amino, mono-lower alkylamino, di-lower alkylamino, lower alkoxycarbonyl or carbamoyl;

$R^4$ is alkyl, alkenyl, alkoxy or alkenyloxy which may be optionally substituted with lower alkyl, aryl, cycloalkyl or fluorine atom(s);

$R^5$ is —$CONH_2$, —CN or —$CH_2NH_2$;

X is a single bond, or an aryl, biphenyl or terphenyl group optionally containing one or more hetero atom(s) and/or being substituted with halogen atom(s) or lower alkyl;

Y is a single bond, —$CH_2$—, —CH(lower alkyl)-, —CONH— or —CON(lower alkyl)-;

Z is —O—, —NH—or —N(lower alkyl)-;

m is an integer of 0 to 4; and n is an integer of 2 to 5;

with the proviso that when —Y—$(CH_2)_{m—X—R}{}^4$ is unsubstituted alkyl or aralkyl, then $R^1$ is not amino, $R^2$ and $R^3$ are not hydrogen, $R^5$is not —$CONH_2$, and Z is not —O— or —NH— at the same time;

and pharmaceutically acceptable salts thereof.

The present invention also relates to a pharmaceutical composition comprising an Aerothricin of Formula (I) and a pharmaceutically acceptable carrier. Furthermore, the present invention relates to the use of such Aerothricins for the preparation of medicaments, as well as to processes and intermediates for the preparation of the Aerothricins of Formula (I). Additionally, the present invention relates to a method for the prophylactic and/or therapeutic treatment of infectious diseases caused by pathogenic microorganisms.

DETAILED DESCRIPTION OF THE INVENTION

Figure 1:
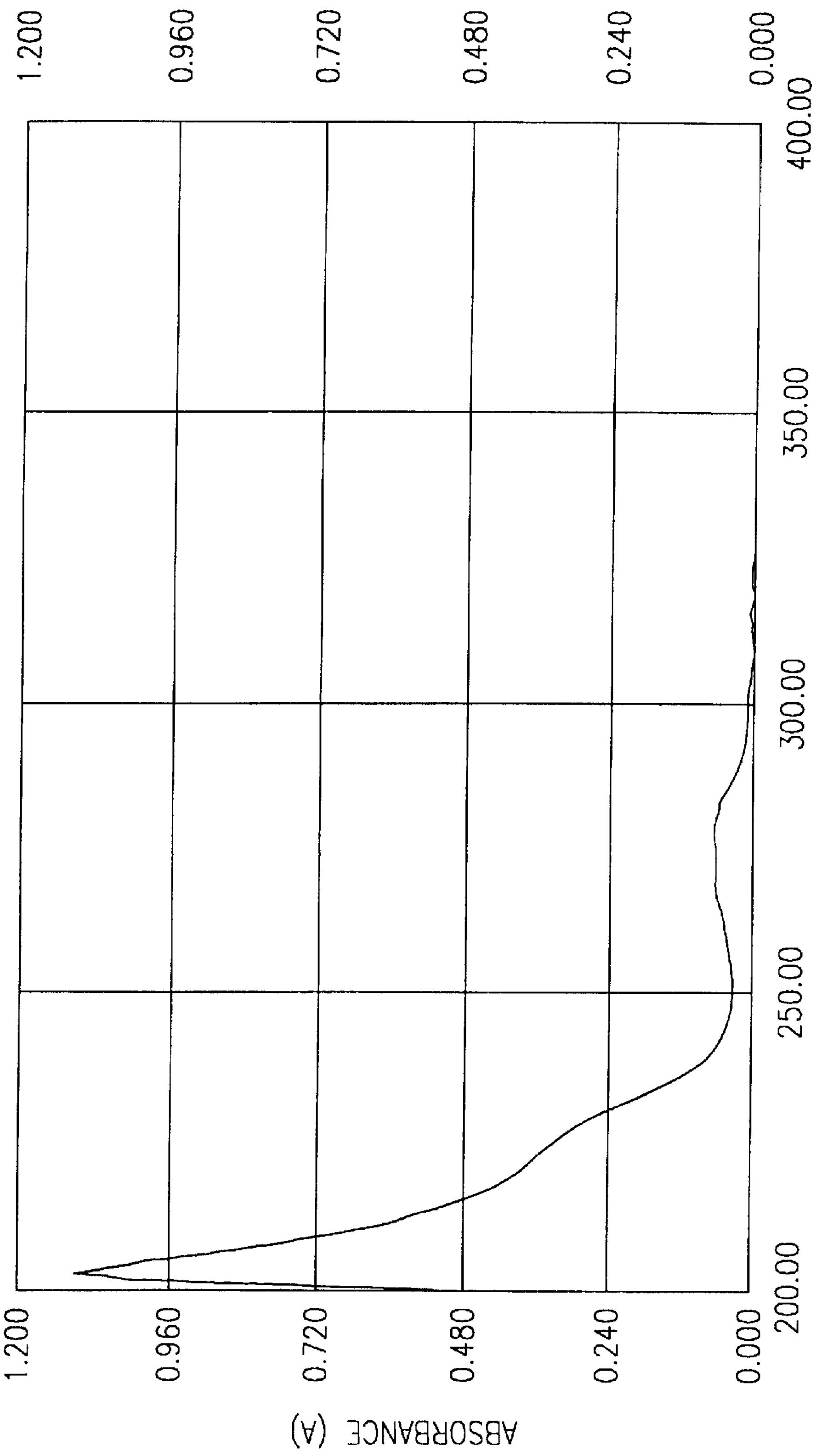
FIG. 1 is the UV spectrum, in methanol, for Aerothricin 1.

In this specification, the term "lower" is used to mean a group consisting of 1 to 6, preferably 1 to 4 carbon atom(s), unless otherwise indicated.

The term "alkyl" refers to a branched or straight chain monovalent saturated aliphatic hydrocarbon radical of one to twenty carbon atoms, preferably of one to sixteen carbon atoms. The term "lower alkyl" refers to a branched or straight chain monovalent alkyl radical of one to six carbon atoms, preferably one to four carbon atoms. This term is further exemplified by such radicals as methyl, ethyl, n-propyl, isopropyl, n-butyl, i-butyl, tert-butyl and the like.

The term "alkenyl" refers to an alkyl group containing one or more double bond(s) in the alkylene chain.

The term "alkynyl" refers to an alkyl group containing one or more triple bond(s) in the alkylene chain.

The term "alkoxy" refers to the group —O—R', where R' is an alkyl. The term "lower alkoxy" refers to the group —O—R', where R' is a lower alkyl.

The term "alkenyloxy" refers to an alkoxy group which contains one or more double bond(s) in the alkylene chain.

The term "acyl" refers to the group —C(O)—R', where R' is a lower alkyl. The term "acylamino" refers to an acyl group attached to an imino radical, i.e., —NH—.

The term "mono-lower alkylamino" refers to a lower alkyl group attached to an imino radical, i.e., —NH—. The term "di-lower alkylamino" refers to two independently selected lower alkyl groups attached to a nitrogen atom, i.e., —N(-lower alkyl)-lower alkyl. The term "tri-lower alkylammonio" means tri-lower alkylammonio containing three independently selected $C_{1-3}$-alkyl groups.

The term "lower alkoxycarbonyl" refers to the group —C(O)OR', where R' is a lower alkyl.

The term "(lower alkylcarbamoyl)amino" refers to the group —NHCONH—R', where R' is a lower alkyl.

The term "halogen atom" refers to fluorine, chlorine, bromine and iodine.

The term "aryl" refers to a monovalent carbocyclic aromatic radical (e.g. phenyl), or two condensed carbocyclic rings (e.g. naphtyl) optionally mono-, di- or tri-substituted, independently, with lower alkyl, trifluoromethyl, halogen and the like.

The term "nitrogen containing heterocycle" refers to a saturated, unsaturated or aromatic monovalent cyclic radical containing at least one nitrogen atom.

The term "heteroaryl" refers to an aromatic monovalent mono- or poly-carbocyclic radical containing at least one heteroatom, i.e. nitrogen, sulfur or oxygen. Examples of heteroaryl residues with one or more nitrogen atoms are pyridyl, pyrazinyl, pyrimidinyl, pyridazinyl, triazinyl and imidazolyl.

The term "cycloalkyl" refers to a monovalent carbocyclic radical of three to ten carbon atoms, preferably of three to six carbon atoms.

The term "pharmaceutically acceptable salts" embraces salts of the Aerothricis of the Formula (I) with inorganic or organic acid such as hydrochloric acid, hydrobromic acid, nitric acid, sulfuric acid, phosphoric acid, citric acid, formic acid, maleic acid, acetic acid, trifluoroacetic acid, succinic acid, tartaric acid, methanesulfonic acid, p-toluenesulfonic acid and the like, which are non-toxic to living organisms. Each substituent of Formula (I) set forth above is explained in more detail hereafter.

In the definition of $R^1$, the term "tri-lower alkylammonio" preferably means trimethylammonio and triethylammonio.

In the definition of $R^{10}$ and $R^{11}$, the term "heteroaryl" preferably means 2-pyridyl, 2-pyrazinyl, 2-pyrimidinyl, 2-pyridazinyl, 2-triazinyl, 2-imidazolyl and the like, more preferably 2-pyridyl and 2-imidazolyl, most preferably 2-pyridyl. The term "lower alkyl" preferably means an alkyl chain consisting of 1 to 6 carbon atoms such as methyl, ethyl, n-propyl, iso-propyl, n-butyl, iso-butyl, sec-butyl, n-pentyl, neopentyl, tert-pentyl, and n-hexyl; preferably methyl, ethyl, n-propyl or n-butyl, most preferably methyl, ethyl or n-propyl. The term "nitrogen containing heterocycles" preferably means morpholino, piperazinyl, N-methylpiperazinyl, pyrrolidinyl, piperidinyl, imidazolidinyl, pyrazolidinyl, imidazolyl, pyrazolyl, triazolyl, pyridinyl, pyrazinyl and the like, more preferably piperazinyl and morpholino, most preferably piperazinyl. The term "phenyl group(s) containing an amino, amidino or guanidino group" preferably means 4-aminophenyl, 4-amidinophenyl, 4-guanidinophenyl and the like.

In the definition of $R^{13}$, the term "a residue derived from natural or unnatural amino acids" preferably means hydrogen or lower alkyl which may be substituted with hydroxy, amino, guanidino, methylthio, mercapto, carbamoyl, carboxy, phenyl, hydroxyphenyl, aminophenyl, imidazolyl or indolyl and the like. Preferable embodiment of $R^{13}$ is lower alkyl substituted with amino or guanidino such as aminomethy, 2-aminoethyl, 3-aminopropyl, 4-aminobutyl, 4-guanidinobutyl.

In the definition of $R^{14}$, the term "lower alkyl" means the same as defined for $R^{10}$ and $R^{11}$. Preferably, it means an alkyl chain consisting of 2 to 5 carbon atoms such as ethyl, propyl, butyl and pentyl. The term "nitrogen containing heterocycles" means the same as defined for $R^{10}$ and $R^{11}$. Preferably, it means morpholino, piperazinyl, N-methylpiperazinyl, pyrrolidinyl, piperidinyl, imidazolidinyl, pyrazolidinyl, imidazolyl, pyrazolyl, triazolyl, pyridinyl, pyrazinyl and the like, more preferably piperazinyl and morpholino. The term "phenyl group(s) containing an amino, amidino or guanidino group" preferably means 4-aminophenyl, 4-amidinophenyl, 4-guanidinophenyl and the like. Preferable embodiment of $R1^4$ is 2-aminoethyl, 3-aminopropyl, 4-aminobutyl, 2-guanidinoethyl, 3-guanidinopropyl, 2-piperazinoethyl, 2-morpholinoethyl, 4-aminophenethyl and the like.

In the definition of R $^{15}$, the terms "lower alkyl", "nitrogen containing heterocycles" and "phenyl group(s) containing an amino, amidino or guanidino group" are the same as defined for $R^{14}$. Preferable embodiment of $R^{15}$ is 2-aminoethyl, 3-aminopropyl, 4-aminobutyl, 2-guanidinoethyl, 3-guanidinopropyl, 2-piperazinoethyl, 2-morpholinoethyl, 4-aminophenethyl and the like.

Preferable embodiments of —$N(R^{10})$—$R^{11}$ [wherein $R^{10}$ and $R^{11}$ are as defined above] are amino, 5-aminopyrid-2-ylamino, methylamino, ethylamino, propylamino, (2-aminoethyl)amino, (3-aminopropyl)amino, [3-[(3-aminopropyl)amino]propyl]amino, (2-piperazinylethyl) amino, (2-morpholinoethyl)amino, N,N-dimethylamino, N,N-diethylamino, N,N-dipropylamino, N,N-ethylmethylamino, N,N-bis(2-aminoethyl)amino, N,N-bis (3-aminopropyl)amino, N,N-bis(4-aminobutyl)amino, N,N-bis(2-piperazinylethyl)amino, N,N-bis(2-morpholinoethyl) amino, N,N-bis(2-guanidinoethyl)amino, N,N-bis(3-guanidinopropyl)amino, N,N-bis(2-pyridin-2-ylethyl) amino, N,N-bis(imidazol-2-ylmethyl)amino, N-(2-aminoethyl)-N-(3-aminopropyl)amino, N-(3-aminopropyl)-N-(2-piperazinylethyl)amino, N-(3-aminopropyl)-N-(2-pyridin-2-ylethyl)amino and the like. More preferable embodiments are amino, 5-aminopyrid-2-ylamino, N,N-dimethylamino, (2-aminoethyl)amino, (3-aminopropyl) amino, [3-[(3-aminopropyl)amino]propyl]amino, (2-piperazinylethyl)amino, N,N-bis(2-aminoethyl)amino, N,N-bis(3-aminopropyl)amino, N,N-bis(4-aminobutyl) amino, N,N-bis(2-piperazinylethyl)amino, N,N-bis(2-guanidinoethyl)amino, N,N-bis(3-guanidinopropyl)amino, N-(2-aminoethyl)-N-(3-aminopropyl)amino, N-(3-aminopropyl)-N-(2-piperazinylethyl)amino and the like. Most preferable embodiments are (3-aminopropyl)amino, N,N-bis(2-aminoethyl)amino, N,N-bis(3-aminopropyl) amino and N,N-bis(2-piperazinylethyl)amino.

In the definition of —$N(R^{15})$—CO—$CH[N(R^{10})R^{11}]$—$R^{13}$, the group —CO—$CH[N(R^{10})R^{11}]$—$R^{13}$ [wherein $R^{10}$ and $R^{11}$ are hydrogen; $R^{13}$ is a residue derived from natural or unnatural amino acids] preferably means sarcosyl, glycyl, alanyl, ornitinyl, lysyl, valyl, leucyl, isoleucyl, tryptophyl, phenylalanyl, methionyl, seryl, tyrosyl, threonyl, cysteinyl, asparaginyl, glutaminyl, aspartyl, glutamyl, arginyl, histidyl, 2,3-diaminopropionyl, 2,4-diaminobutyryl, 2-amino-4-triazol-1-ylbutyryl and the like.

Preferable embodiments of —$N(R^{15})$—CO—$CH[N(R^{10})$ $R^{11}]$—$R^{13}$ are acylamino groups derived from basic amino acids. Examples of such acylamino groups are ornitinylamino, lysylamino, arginylamino, histidylamino, 3-aminoprolylamino, 2,3 -diaminopropionylamino, 2,4-diaminobutyrylamino, 2-amino-4-triazol-1-ylbutyrylamino, [3 -amino-2-[bis(2-aminoethyl)amino]propionyl]amino, [4-amino-2-[bis(2-aminoethyl)amino]butyryl]amino, [5-amino-2-[bis(2-aminoethyl)amino]valeryl]amino, N-(3-aminopropyl)-N-(2,3-diaminopropionyl)amino, N-(3-aminopropyl)-N-(2,4-diaminobutyryl)amino, N-(3-aminopropyl)-N-(2,5-diaminovaleryl)amino, N-(3-aminopropyl)-N-(2,6-diaminohexanoyl)amino and the like; more preferably ornitinylamino, lysylamino, arginylamino, histidylamino, 2,3-diaminopropionylamino, 2,4-diaminobutyrylamino, [3-amino-2-[bis(2-aminoethyl) amino]propionyl]amino, [4-amino-2-[bis(2-aminoethyl) amino]butyryl]amino, [5-amino-2-[bis(2-aminoethyl) amino]valeryl]amino, N-(3-aminopropyl)-N-(2,3-diaminopropionyl)amino, N-(3-aminopropyl)-N-(2,4-diaminobutyryl)amino, N-(3-aminopropyl)-N-(2,5-diaminovaleryl)amino and N-(3-aminopropyl)-N-(2,6-diaminohexanoyl)amino, most preferably ornitinylamino, lysylamino, 2,4-diaminobutyrylamino, [4-amino-2-[bis(2-aminoethyl)amino]butyryl]amino, [5-amino-2-[bis(2-aminoethyl)amino]valeryl]amino, N-(3-aminopropyl)-N-(2,4-diaminobutyryl)amino, N-(3-aminopropyl)-N-(2,5-diaminovaleryl)amino and N-(3-aminopropyl)-N-(2,6-diaminohexanoyl)amino.

In the definition of $R^1$, preferable embodiment of

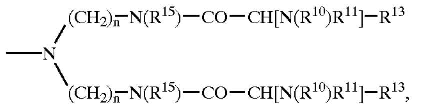

is bis[2-(ornitylamino)ethyl]amino, bis-[3-(ornitylamino) propyl]amino, [2-(lysylamino)ethyl]amino, bis-[3-(lysylamino)propyl]amino and the like.

In the definition of $R^1$, preferable embodiment of

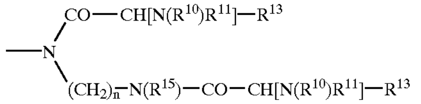

is N-ornityl-N-[2-(ornitylamino)ethyl]-amino, N-ornityl-N-[3-(ornitylamino)propyl]-amino, N-ornityl-N-[3-(lysylamino)propyl]amino, N-ornityl-N-[3-(lysylamino) propyl]-amino, N-lysyl-N-[2-(ornitylamino)ethyl]amino, N-lysyl-N-[3-(ornitylamino)propyl]-amino, N-lysyl-N-[2-(lysylamino)ethyl]amino, N-lysyl-N-[3-(lysylamino)propyl] amino and the like.

In the definition of $R^1$, preferable embodiment of

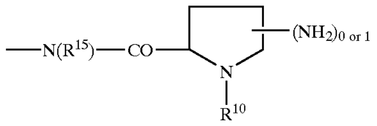

is prolylamino, 3-aminoprolylamino, 4-aminoprolylamino, N-(3-aminopropyl)-N-prolylamino, (2-aminoethyl) prolylamino and the like.

The term "—$NHCOCH(R^{13})$—$NHCOCH(NH_2)$—$R^{13}$" [wherein $R^{13}$ is as defined above] preferably means ornityl-ornitylamino, lysyl-ornitylamino, ornityl-lysylamino, lysyl-lysylamino and the like.

In the term "—$N(R^{15})$—CO—$R^{14}$ " [wherein $R^{14}$ and $R^{15}$ are as defined above], the term "nitrogen containing heterocycle" and the term "phenyl group(s) containing an amino, amidino or guanidino group" are as defined above.

Preferable embodiments of —$N(R^{15})$—CO—$R^{14}$ are 3-aminopropionylamino, 3-guanidinopropionylamino, 3-piperazinylpropionylamino, (3-pyridin-3-ylpropionyl) amino, [3-(4-aminophenyl)propionyl]amino, N-(3-aminopropionyl)-N-(3-aminopropyl)amino and the like.

In a preferred aspect, $R^1$ is —$N(R^{10})$—$R^{11}$, wherein $R^{10}$ and $R^{11}$ are as defined above. In another preferred aspect, $R^1$ is —$N(R^{15})$—CO—$CH[N(R^{10})R^{11}]$—$R^{13}$, wherein $R^{10}$, $R^{11}$, $R^{13}$ and $R^{15}$ are as defined above. In another preferred aspect, $R^1$ is —$N(R^{15})$—CO—$R^{14}$, wherein $R^{14}$ and $R^{15}$ are as defined above. In another preferred aspect, $R^1$ is

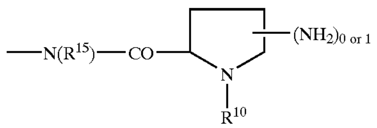

wherein $R^{10}$ and $R^{15}$ are as defined above. In another preferred aspect, $R^1$ is —NHCOCH($R^{13}$)—NHCOCH($NH_2$)—$R^{13}$, wherein $R^{13}$ is as defined above. In another preferred aspect, $R^1$ is tri-lower alkylammonio. In still another preferred aspect, $R^1$ is amino or guanidino.

In the definition of $R^2$, the term "lower alkyl optionally substituted with acyl, carboxy, carbamoyl, amino, mono-lower alkylamino or di-lower alkylamino" preferably means methyl, ethyl, n-propyl, isopropyl, butyl, oxo-lower alkyl, carboxy-lower alkyl, carbamoyl-lower alkyl, amino-lower alkyl and the like, more preferably methyl, ethyl, n-propyl, n-butyl, 2-oxopropyl, carboxymethyl, carbamoylmethyl, 3-aminopropyl and the like.

The term "lower alkenyl optionally substituted with acyl, carboxy, carbamoyl, amino, mono-lower alkylamino or di-lower alkylamino" preferably means allyl, 2-butenyl, 3-butenyl and the like, more preferably allyl.

In a preferred aspect, $R^2$ is hydrogen, hydroxysulfonyl or lower alkyl such as methyl or ethyl.

In the definition of $R^3$, the term "acylamino" preferably means lower alkylcarbonylamino such as acetylamino, propionylamino or isobutyrylamino, or an acylamino group derived from natural or unnatural amino acids such as sarcosylamino, glycylamino, alanylamino, ornitylamino, lysylamino, prolylamino, valylamino, leucylamino, isoleucylamino, tryptophylamino, phenylalanylamino, methionylamino, serylamino, tyrosylamino, threonylamino, cysteinylamino, asparaginylamino, glutamylamino, aspartylamino, glutamylamino, arginylamino, histidylamino and the like; preferably sarcosylamino, glycylamino, alanylamino, lysylamino, prolylamino and the like.

The term "(lower-alkylcarbamoyl)amino" preferably means methylcarbamoylamino, ethylcarbamoylamino, propylcarbamoylamino, butylcarbamoylamino and the like, more preferably methylcarbamoylamino or ethylcarbamoylamino.

The term "lower alkoxy" preferably means methoxy, ethoxy, propoxy, butoxy and the like, more preferably methoxy and ethoxy.

The term "lower alkoxycarbonyl" preferably means methoxycarbonyl, ethoxycarbonyl, propoxycarbonyl, butoxycarbonyl and the like, more preferably methoxycarbonyl and ethoxycarbonyl.

The term "lower alkyl which may be optionally substituted with hydroxy, amino, mono-lower alkylamino, di-lower alkylamino, lower alkoxycarbonyl or carbamoyl" preferably means methyl, ethyl, propyl, aminomethyl, aminoethyl, aminopropyl, hydroxymethyl, hydroxyethyl, methylaminomethyl, 2-(methylamino)ethyl, 3-(methylamino)propyl, dimethylaminomethyl, 2-(dimethylamino)ethyl, 3-(dimethylamino)propyl, 2-(methoxycarbonyl)ethyl, 2-(carbamoyl)ethyl and the like.

The term "lower alkenyl which may be optionally substituted with hydroxy, amino, mono-lower alkylamino, di-lower alkylamino, lower alkoxycarbonyl or carbamoyl" preferably means vinyl, 2-(methoxycarbonyl)vinyl, 2-(carbamoyl)vinyl and the like.

The term "lower alkynyl which may be optionally substituted with hydroxy, amino, mono-lower alkylamino, di-lower alkylamino, lower alkoxycarbonyl or carbamoyl" preferably means ethynyl, propynyl, hydroxypropynyl, aminopropynyl, diethylaminopropynyl and the like.

In a preferred aspect, $R^3$ is hydrogen, hydroxy, nitro, amino or acylamino. In another preferred aspect $R^3$ is (lower alkylcarbamoyl)amino, carboxyl, lower alkoxy or lower alkoxycarbonyl.

In the definition of $R^4$, the term "alkyl, alkenyl, alkoxy or alkenyloxy" preferably lo means an alkyl, alkenyl, alkoxy or alkenyloxy group containing 3 to 16 carbon atoms, such as propyl, butyl, pentyl, hexyl, heptyl, octyl, oct-4-enyl, oct-6-enyl, nonanyl, decyl, undecyl, dodecyl, tridecyl, tetradecyl, pentadecyl, hexadecyl, propoxy, butoxy, pentyloxy, hexyloxy, heptyloxy, octyloxy, oct-4-enyloxy, oct-6-enyloxy, nonanyloxy, non-5-enyloxy, decyloxy and the like.

The term "lower alkyl" preferably means methyl, ethyl, propyl, butyl, pentyl, more preferably methyl or ethyl.

The term "aryl" means an aryl group which may optionally be substituted with lower alkyl, trifluoromethyl or halogen atom(s) such as phenyl, naphtyl, 3-fluorophenyl, 3-bromophenyl, 3-chlorophenyl, 4-fluorophenyl, 4-bromophenyl, 4-chlorophenyl, 3-methylphenyl, 4-methylphenyl, 4-trifluoromethylphenyl.

The term "cycloalkyl" preferably means cyclopropyl, cyclobutyl, cyclopentyl, cyclohexyl, adamantyl and the like.

The term "alkyl, alkenyl, alkoxy or alkenyloxy which may be optionally substituted with lower alkyl, aryl, cycloalkyl or fluorine atom(s)" preferably means 5-methylhexyl, 1-methyltridecyl, 2-ethylbutoxy, 4-methylpentyloxy, 2-propylpentyloxy, 2-ethylhexyloxy, 3,7-dimethyloctyloxy, 2-phenylethoxy, 2-(4-fluorophenyl)ethoxy, 2-(4-chlorophenyl)ethoxy, 2-(3-fluorophenyl)ethoxy, 2-(4-trifluorophenyl)ethoxy, 3 -phenylpropoxy, 2-naphtylethoxy, 3-naphtylpropoxy, 2-cyclopropylethoxy, 2-cyclobutylethoxy, 2-cyclopentylethoxy, 3-cyclopentylpropoxy, 2-cyclohexylethoxy, 3-cyclohexylpropoxy, 3,3-diphenylpropoxy, 3,3,3-trifluoropropoxy, 4,4,4-trifluorobutoxy, 5,5,5-trifluoropentyloxy and the like.

In a preferred aspect, $R^4$ is alkyl or alkoxy which may be optionally substituted with lower alkyl, aryl, cycloalkyl or fluorine atom(s).

Preferable embodiments of $R^5$ are —$CONH_2$ or —$CH_2NH_2$.

In the definition of X, the term "hetero atom" preferably means nitrogen, sulfur and oxygen.

The term "aryl, biphenyl or terphenyl optionally containing one or more hetero atom(s)" preferably means

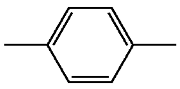,
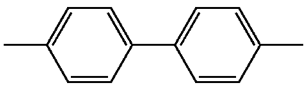,
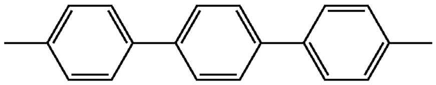,
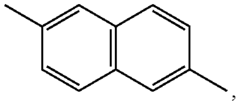,
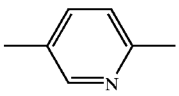,
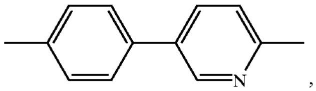,
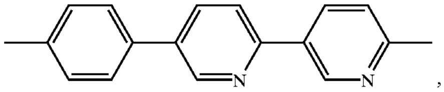,
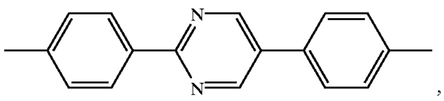,
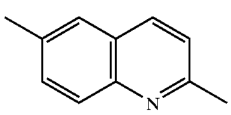,
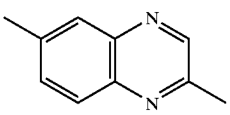,
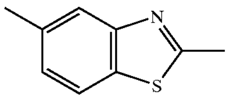,
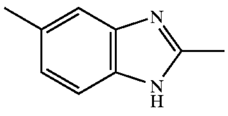, -continued

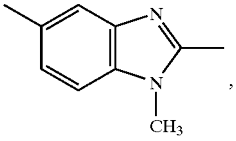,
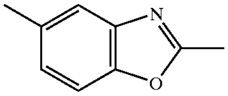,
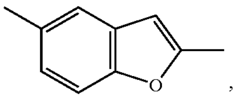,
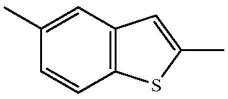
or
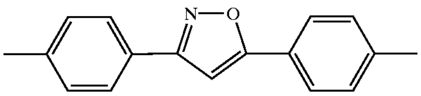

and the like, which may be further substituted with halogen atom(s) or lower alkyl. The open-ended lines in the formulas above indicate the preferred linkage in the corresponding position.

The most preferable embodiment of X is a single bond,

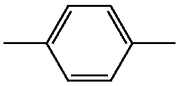,
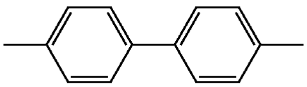
or
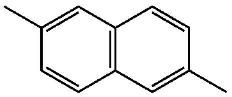, which may be further substituted with halogen atom(s) or lower alkyl, preferably methyl.

In the definition of Y, the term "lower alkyl" preferably means an alkyl group consisting of 1 to 3 carbon atoms, e.g. methyl, ethyl or propyl. The preferable embodiment of Y is a single bond, —$CH_2$—, —$CH(CH_3)$—, —CONH— or —$CON(CH_3)$—, more preferably a single bond, —CH ($CH_3$)— or —CONH—.

In the definition of Z, the term "—N(lower alkyl)-" preferably means an N-alkyl group consisting of 1 to 3 carbon atoms, e.g. N-methyl, N-ethyl or N-propyl. A preferable embodiment of Z is —O—; another preferable embodiment of Z is —NH—.

m is an integer of 0 to 4, preferably 0 to 2.

Preferred Aerothricins in accordance with the present invention are Aerothricins 2 and 4 to 131 as exemplified in the following Table 1.

TABLE 1

(I)

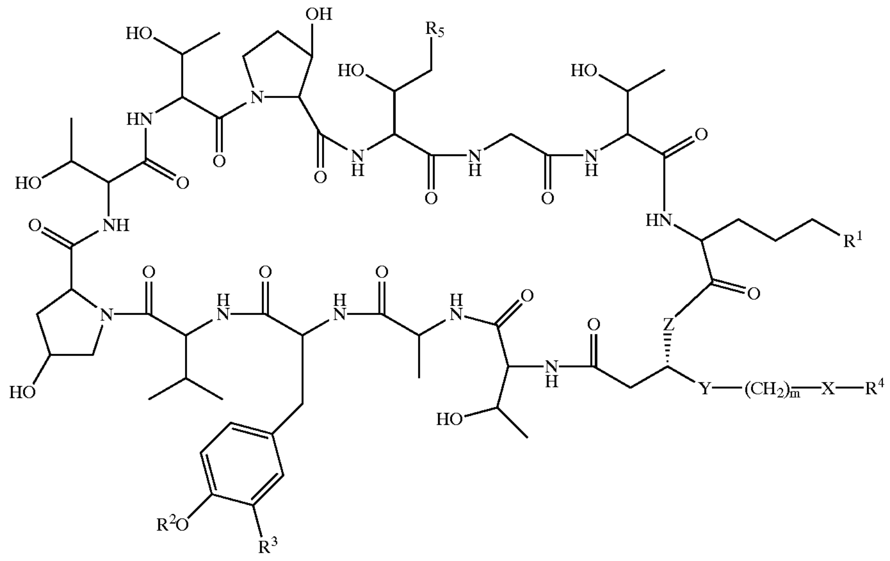

Formula (I)

| Compound name | $R^1$ | $R^2$ | $R^3$ | $R^5$ | Z | $Y-(CH_2)_m-X-R^4$ |
|---|---|---|---|---|---|---|
| Aerothricin 1 (starting material) | $NH_2$ | H | H | $CONH_2$ | O | $CH(CH_3)-(CH_2)_{11}CH_3$ |
| Aerothricin 2 | $NH_2$ | H | OH | $CONH_2$ | O | $(CH_2)_{12}CH_3$ |
| Aerothricin 3 (starting material) | $NH_2$ | H | H | $CONH_2$ | O | $(CH_2)_{12}CH_3)$ |
| Aerothricin 4 | $NHC(=NH)NH_2$ | H | H | $CONH_2$ | O | $(CH_2)_{12}CH_3$ |
| Aerothricin 5 | $NH_2$ | $CH_3$ | H | $CONH_2$ | O | $(CH_2)_{12}CH_3$ |
| Aerothricin 6 | $NH_2$ | $CH_2CH_3$ | H | $CONH_2$ | O | $(CH_2)_{12}CH_3$ |
| Aerothricin 7 | $NH_2$ | $CH_2-CH=CH_2$ | H | $CONH_2$ | O | $(CH_2)_{12}CH_3$ |
| Aerothricin 8 | $NH_2$ | $CH_2COCH_3$ | H | $CONH_2$ | O | $(CH_2)_{12}CH_3$ |
| Aerothricin 9 | $NH_2$ | $CH_2CO_2H$ | H | $CONH_2$ | O | $(CH_2)_{12}CH_3$ |
| Aerothricin 10 | $NH_2$ | $CH_2CONH_2$ | H | $CONH_2$ | O | $(CH_2)_{12}CH_3$ |
| Aerothricin 11 | $NH_2$ | $CH_3$ | $OCH_3$ | $CONH_2$ | O | $(CH_2)_{12}CH_3$ |
| Aerothricin 12 | $N(CH_3)_2$ | $CH_3$ | H | $CONH_2$ | O | $(CH_2)_{12}CH_3$ |
| Aerothricin 13 | $N(CH_3)_2$ | H | H | $CONH_2$ | O | $(CH_2)_{12}CH_3$ |
| Aerothricin 14 | $NHCOCH_2NHCH_3$ | H | H | $CONH_2$ | O | $(CH_2)_{12}CH_3$ |

TABLE 1-continued (I)

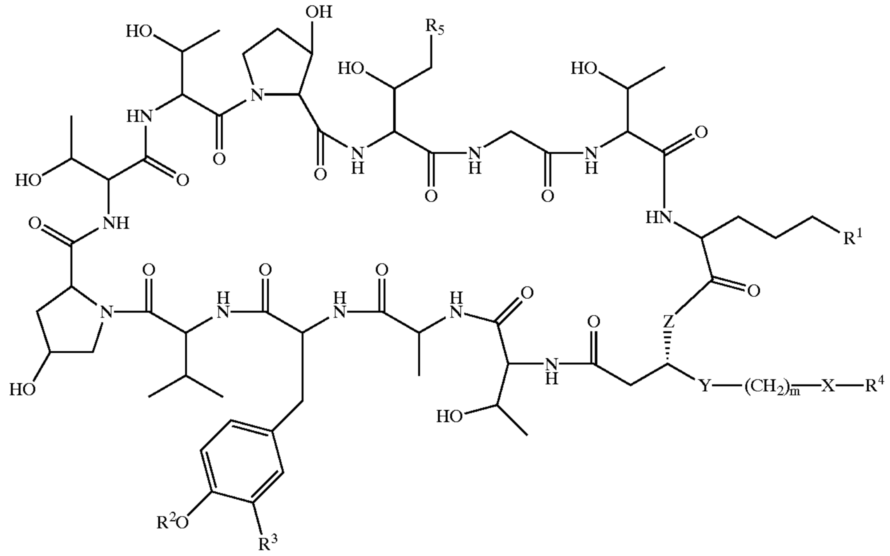

Formula (I)

| Compound name | $R^1$ | $R^2$ | $R^3$ | $R^5$ | Z | $Y—(CH_2)_m—X—R^4$ |
|---|---|---|---|---|---|---|
| Aerothricin 15 | 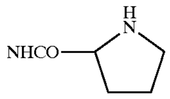 | H | H | $CONH_2$ | O | $(CH_2)_{12}CH_3$ |
| Aerothricin 16 | $NH_2$ | H | $NO_2$ | $CONH_2$ | O | $(CH_2)_{12}CH_3$ |
| Aerothricin 17 | $NH_2$ | H | $NH_2$ | $CONH_2$ | O | $(CH_2)_{12}CH_3$ |
| Aerothricin 18 | $NH_2$ | H | $NHCOCH_2NH_2$ | $CONH_2$ | O | $(CH_2)_{12}CH_3$ |
| Aerothricin 19 | $NH_2$ | H | $NHCOCH_3$ | $CONH_2$ | O | $(CH_2)_{12}CH_3$ |
| Aerothricin 20 | $NH_2$ | H | $NHCOCH(CH_3)NH_2$ | $CONH_2$ | O | $(CH_2)_{12}CH_3$ |
| Aerothricin 21 | $NHCOCH_2NH_2$ | H | $NHCOCH_2NH_2$ | $CONH_2$ | O | $(CH_2)_{12}CH_3$ |
| Aerothricin 22 | $NH_2$ | H | $NHCONHCH_3$ | $CONH_2$ | O | $(CH_2)_{12}CH_3$ |
| Aerothricin 23 | $NH_2$ | H | $NHCONHCH_2CH_3$ | $CONH_2$ | O | $(CH_2)_{12}CH_3$ |
| Aerothricin 24 | $NH_2$ | H | $CH{=}CH—CO_2CH_3$ | $CONH_2$ | O | $(CH_2)_{12}CH_3$ |
| Aerothricin 25 | $N(CH_3)_2$ | H | $NO_2$ | $CONH_2$ | O | $(CH_2)_{12}CH_3$ |
| Aerothricin 26 | $NHCOCH_2NHCH_3$ | H | $NO_2$ | $CONH_2$ | O | $(CH_2)_{12}CH_3$ |

TABLE 1-continued (I)

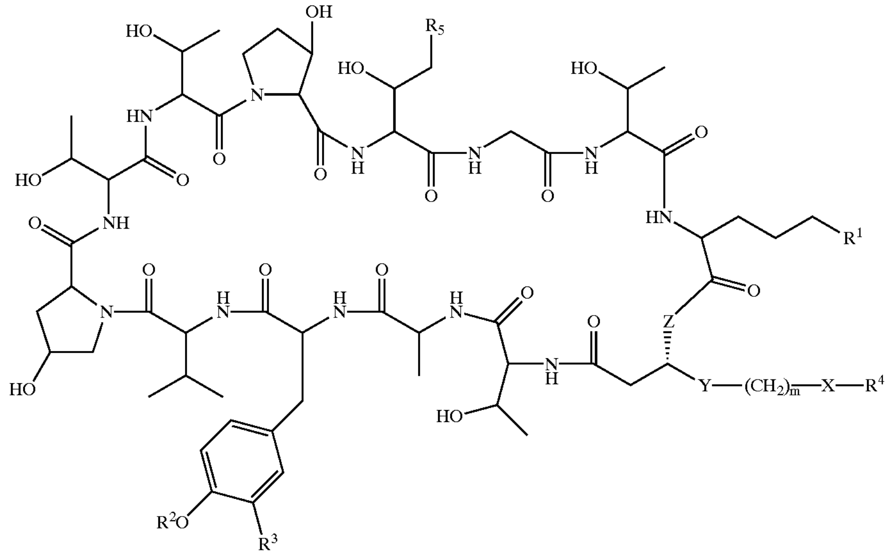

Formula (I)

| Compound name | $R^1$ | $R^2$ | $R^3$ | $R^5$ | Z | $Y—(CH_2)_m—X—R^4$ |
|---|---|---|---|---|---|---|
| Aerothricin 27 | 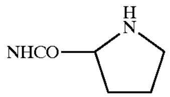 | H | $NO_2$ | $CONH_2$ | O | $(CH_2)_{12}CH_3$ |
| Aerothricin 28 | $NHCOCH_2NH_2$ | H | $NO_2$ | $CONH_2$ | O | $(CH_2)_{12}CH_3$ |
| Aerothricin 29 | $NHCOCH_2NH_2$ | H | $NH_2$ | $CONH_2$ | O | $(CH_2)_{12}CH_3$ |
| Aerothricin 30 | $N(CH_3)_2$ | H | $NHCOCH(CH_3)N(CH_3)_2$ | $CONH_2$ | O | $(CH_2)_{12}CH_3$ |
| Aerothricin 31 | $NH_2$ | H | H | $CH_2NH_2$ | O | $(CH_2)_{12}CH_3$ |
| Aerothricin 32 | $NH_2$ | H | H | CN | O | $(CH_2)_{12}CH_3$ |
| Aerothricin 33 | $NH_2$ | H | H | $CONH_2$ | NH | 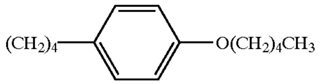 |
| Aerothricin 34 | $NH_2$ | H | H | $CONH_2$ | NH | 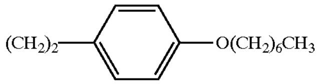 |

TABLE 1-continued
(I)
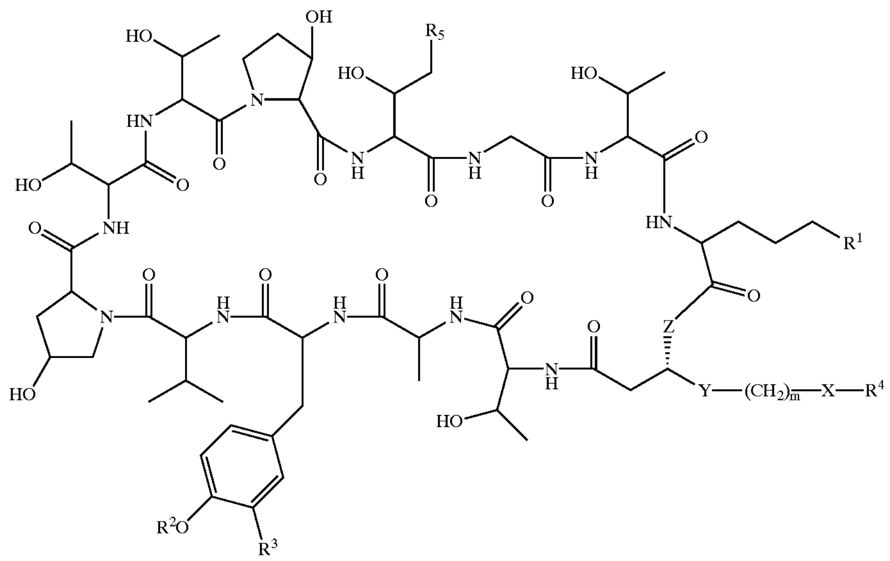
Formula (I)
| Compound name | $R^1$ | $R^2$ | $R^3$ | $R^5$ | Z | $Y—(CH_2)_m—X—R^4$ |
|---|---|---|---|---|---|---|
| Aerothricin 35 | $NH_2$ | H | H | $CONH_2$ | NH | 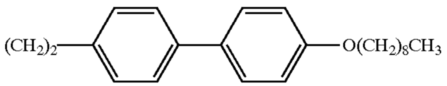 |
| Aerothricin 36 | $NH_2$ | H | H | $CONH_2$ | NH | 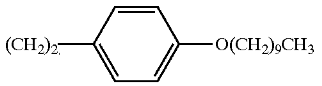 |
| Aerothricin 37 | $NH_2$ | H | H | $CONH_2$ | NH | 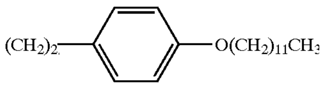 |
| Aerothricin 38 | $NH_2$ | H | H | $CONH_2$ | NH | 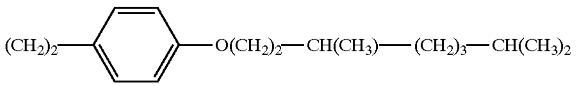 |

TABLE 1-continued
(I)
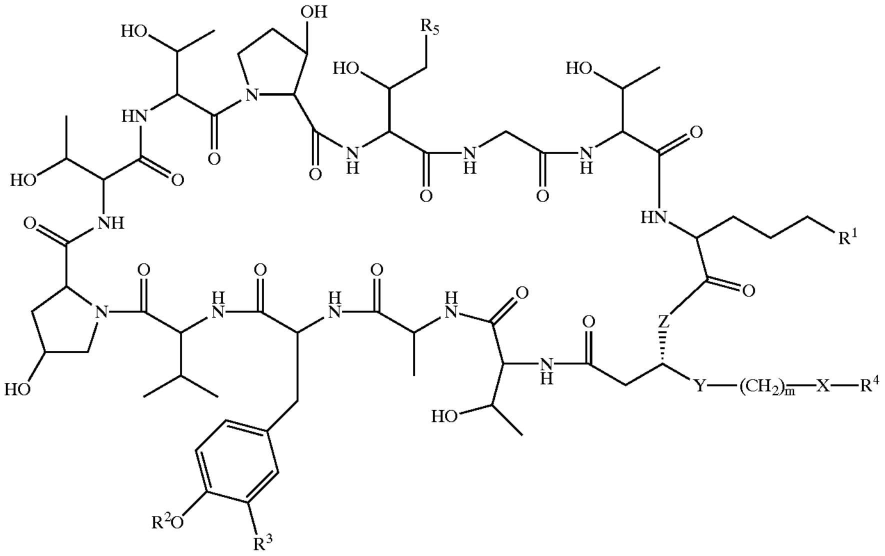
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 39 | $NH_2$ | H | $NO_2$ | $CONH_2$ | NH | $(CH_2)_{12}CH_{13}$ |
| Aerothricin 40 | $NH_2$ | H | H | $CONH_2$ | NH | 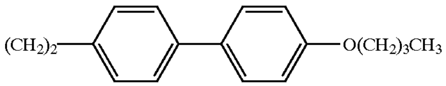 |
| Aerothricin 41 | $NH_2$ | H | H | $CONH_2$ | NH | 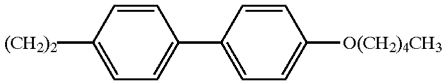 |
| Aerothricin 42 | $NH_2$ | H | H | $CONH_2$ | NH | 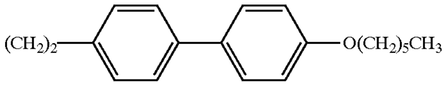 |
| Aerothricin 43 | $NH_2$ | H | H | $CONH_2$ | NH | 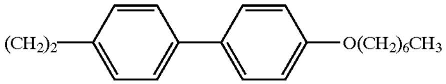 |

TABLE 1-continued
(I)
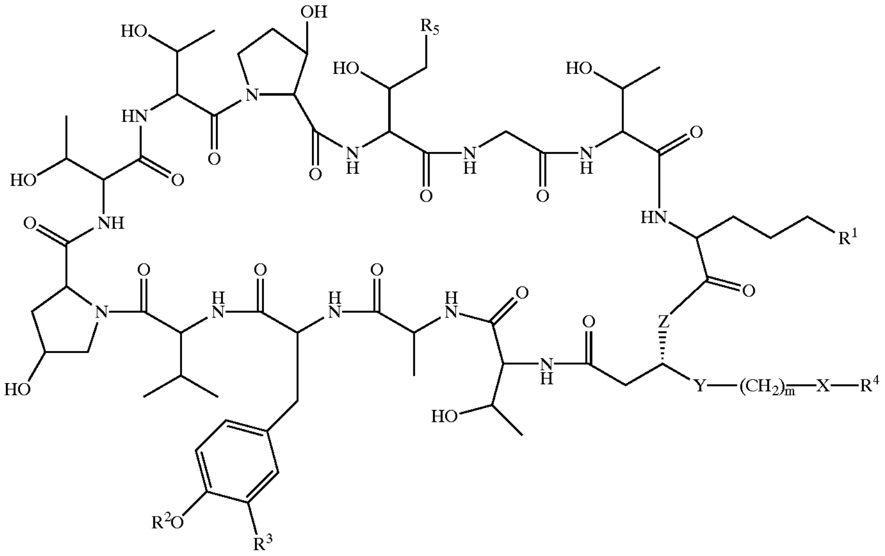
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 44 | $NH_2$ | H | H | $CONH_2$ | NH | 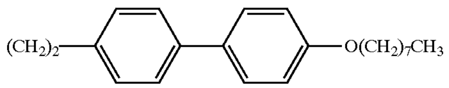 |
| Aerothricin 45 | $NH_2$ | H | H | $CONH_2$ | NH | 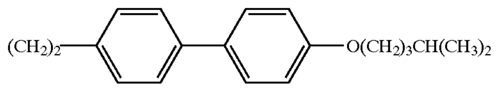 |
| Aerothricin 46 | $NH_2$ | H | H | $CONH_2$ | NH | 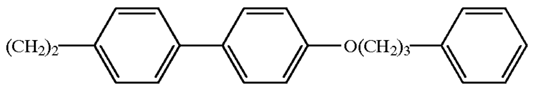 |
| Aerothricin 47 | $NH_2$ | H | H | $CONH_2$ | NH | 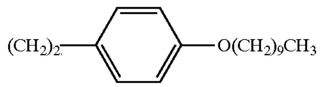 |

TABLE 1-continued
(I)
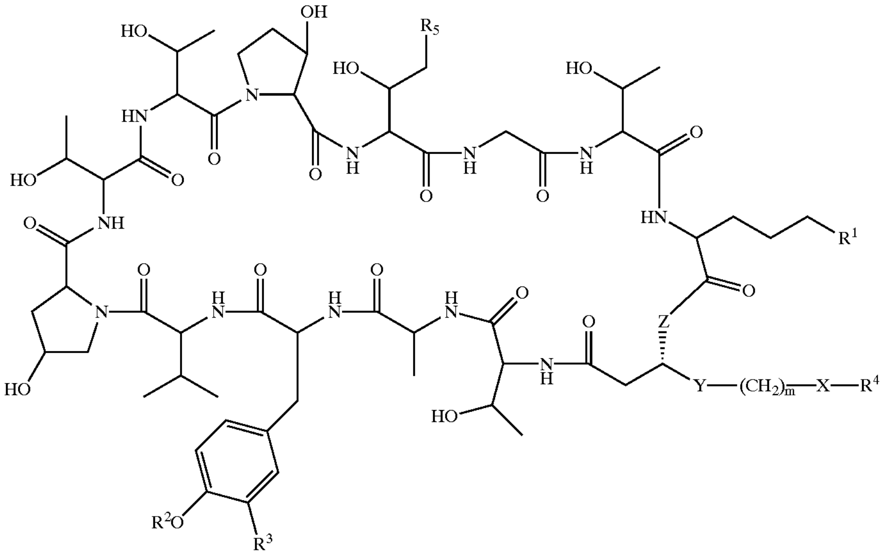
| Compound name | $R^1$ | $R^2$ | Formula (I) $R^3$ | $R^5$ | Z | $Y-(CH_2)_m-X-R^4$ |
|---|---|---|---|---|---|---|
| Aerothricin 48 | $NH_2$ | H | H | $CONH_2$ | NH | 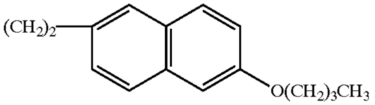 |
| Aerothricin 49 | $NH_2$ | H | H | $CONH_2$ | NH | 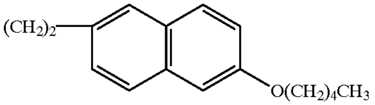 |
| Aerothricin 50 | $NH_2$ | H | H | $CONH_2$ | NH | 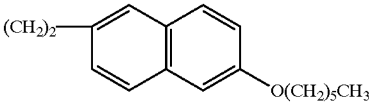 |

TABLE 1-continued
(I)
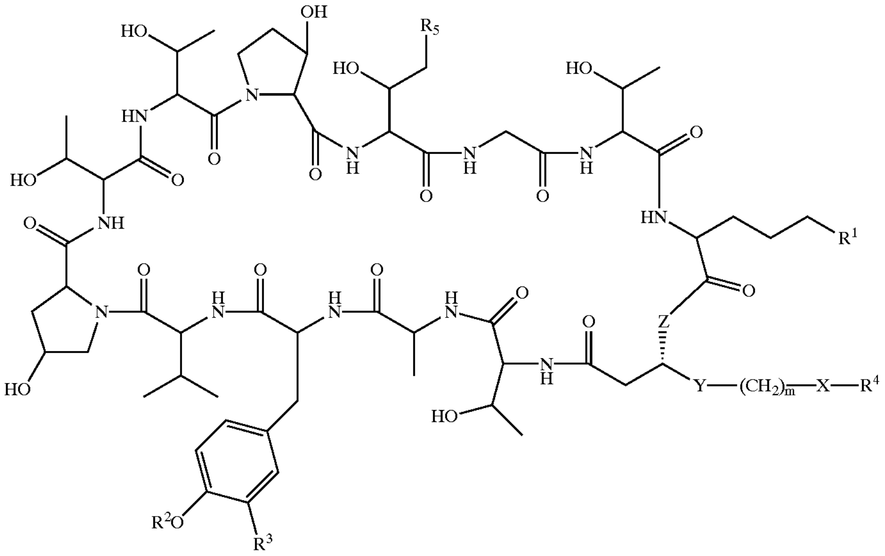
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 51 | $NH_2$ | H | H | $CONH_2$ | NH | 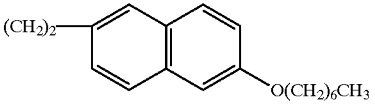 |
| Aerothricin 52 | $NH_2$ | H | H | $CONH_2$ | NH | 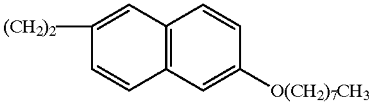 |
| Aerothricin 53 | $NH_2$ | H | H | $CONH_2$ | NH | 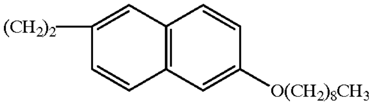 |

TABLE 1-continued
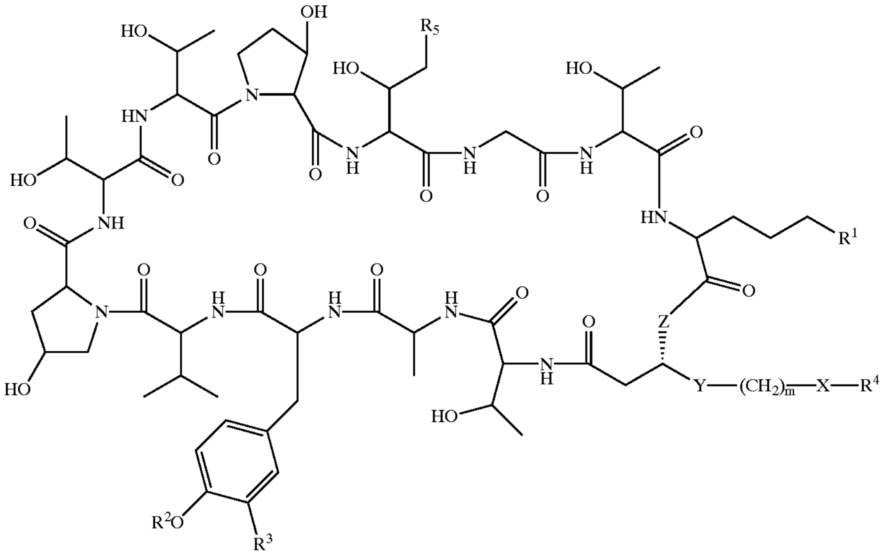
(I)
| Compound name | $R^1$ | $R^2$ | Formula (I) $R^3$ | $R^5$ | Z | $Y-(CH_2)_m-X-R^4$ |
|---|---|---|---|---|---|---|
| Aerothricin 54 | $NH_2$ | H | $NO_2$ | $CONH_2$ | NH | 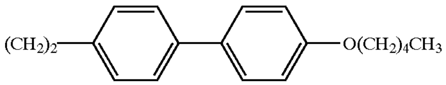 |
| Aerothricin 55 | $NH_2$ | H | $NO_2$ | $CONH_2$ | NH | 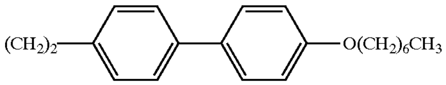 |
| Aerothricin 56 | $NH_2$ | H | $NH_2$ | $CONH_2$ | NH | 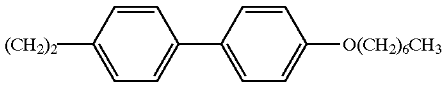 |
| Aerothricin 57 | $NH_2$ | H | $NHCOCH_3$ | $CONH_2$ | NH | 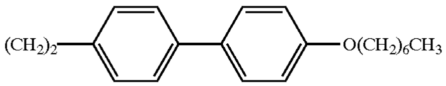 |

TABLE 1-continued
(I)
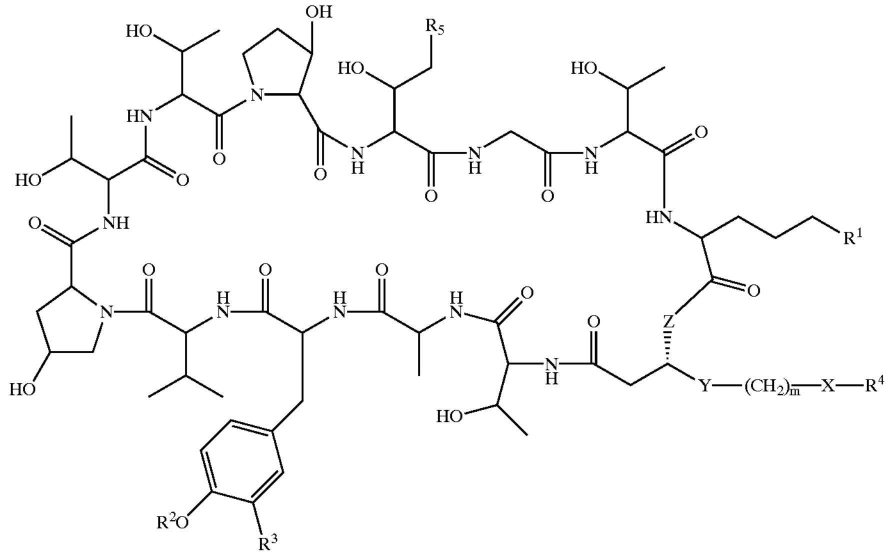
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 58 | $NH_2$ | H | $NHCOCH(CH_3)NH_2$ | $CONH_2$ | NH | 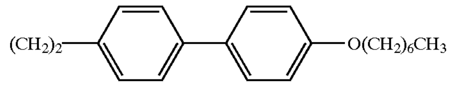 |
| Aerothricin 59 | $NH_2$ | H | $NHCOCH_2NH_2$ | $CONH_2$ | NH | 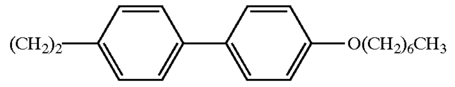 |
| Aerothricin 60 | $NH_2$ | H | $NHCOCH_2NHCH_3$ | $CONH_2$ | NH | 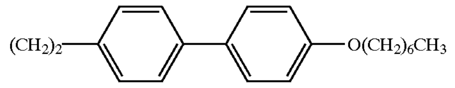 |
| Aerothricin 61 | $NH_2$ | H | $NHCO(CH_2)_2NH_2$ | $CONH_2$ | NH | 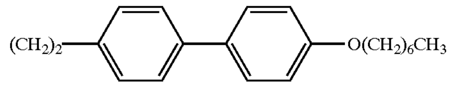 |

TABLE 1-continued (I)

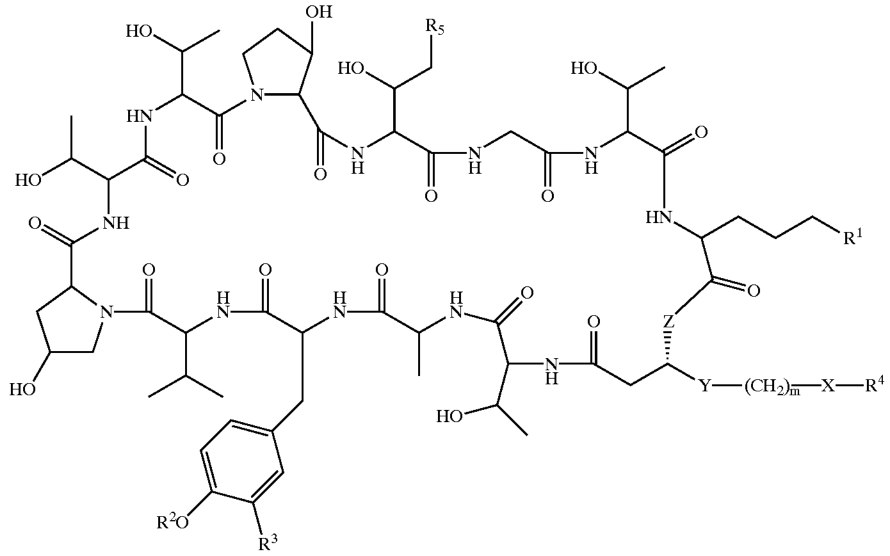

Formula (I)

| Compound name | $R^1$ | $R^2$ | $R^3$ | $R^5$ | Z | Y—$(CH_2)_m$—X—$R^4$ |
|---|---|---|---|---|---|---|
| Aerothricin 62 | $NH_2$ | H | $NHCONHCH_2CH_3$ | $CONH_2$ | NH | 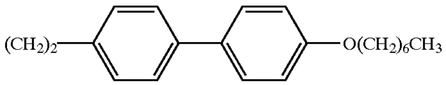 |
| Aerothricin 63 *(S) configuration | —NHCO—$\overset{*}{C}HCH_2NH_2$ with $N(CH_2CH_2NH_2)_2$ on the starred carbon | H | H | $CONH_2$ | O | $(CH_2)_{12}CH_3$ |
| Aerothricin 64 | $NH_2$ | H | H | $CONH_2$ | NH | $CONH(CH_2)_{10}CH_3$ |
| Aerothricin 65 | $NH_2$ | H | H | $CONH_2$ | NH | $CONH(CH_2)_{12}CH_3$ |
| Aerothricin 66 | $NH_2$ | H | H | $CONH_2$ | NH | $CONH(CH_2)_{14}CH_3$ |
| Aerothricin 67 | $NH_2$ | H | H | $CONH_2$ | NH | 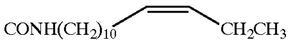 |
| Aerothricin 68 | $NH_2$ | H | H | $CONH_2$ | NH | 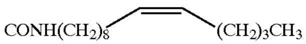 |
| Aerothricin 69 | $NH_2$ | H | H | $CONH_2$ | NH | $CON(CH_3)—(CH_2)_{12}CH_3$ |

TABLE 1-continued
(I)
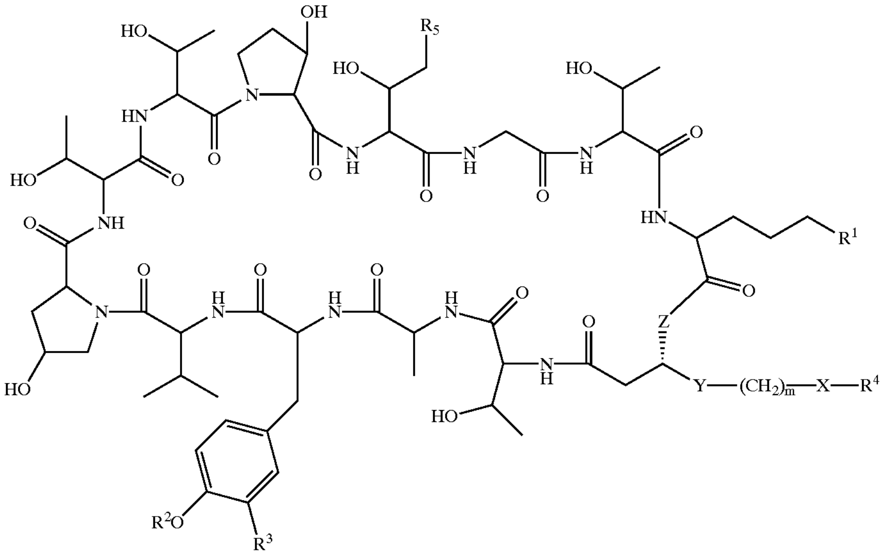
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 70 | $NH_2$ | H | H | $CONH_2$ | NH | $CON(CH_3)-(CH_2)_{14}CH_3$ |
| Aerothricin 71 | $NH_2$ | H | H | $CONH_2$ | NH | 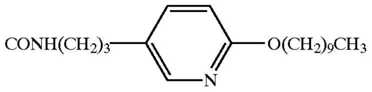 |
| Aerothricin 72 | $NH_2$ | H | H | $CONH_2$ | NH | 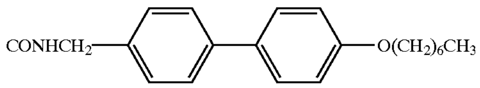 |
| Aerothricin 73 | $NH_2$ | H | H | $CONH_2$ | NH | 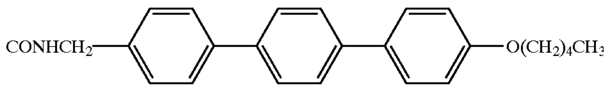 |
| Aerothricin 74 | $NHC(=NH)NH_2$ | H | H | $CONH_2$ | NH | $CONH(CH_2)_{14}CH_3$ |
| Aerothricin 75 | $N(CH_3)_2$ | H | H | $CONH_2$ | NH | $CONH(CH_2)_{14}CH_3$ |
| Aerothricin 76 | $NH_2$ | $CH_3$ | H | $CONH_2$ | NH | $CONH(CH_2)_{14}CH_3$ |

TABLE 1-continued (I)

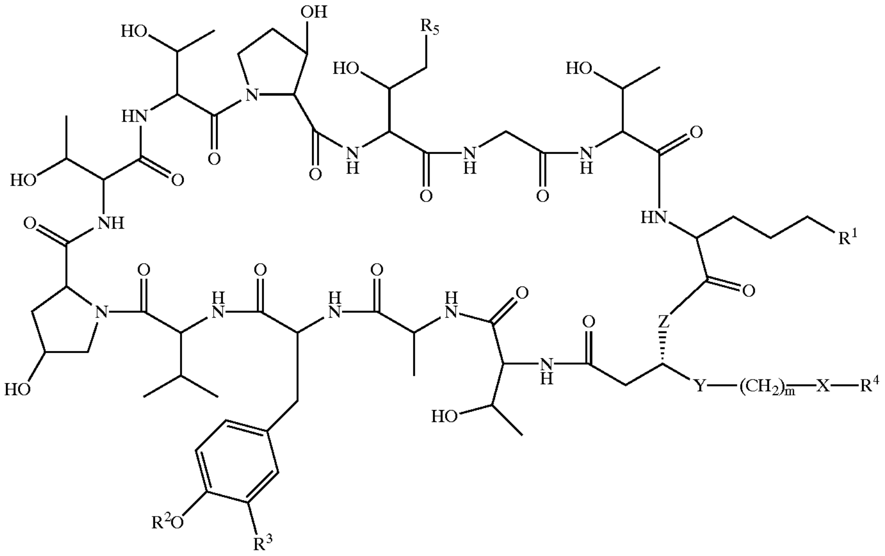

Formula (I)

| Compound name | $R^1$ | $R^2$ | $R^3$ | $R^5$ | Z | $Y—(CH_2)_m—X—R^4$ |
|---|---|---|---|---|---|---|
| Aerothricin 77 | $NH_2$ | H | $NO_2$ | $CONH_2$ | NH | $CONH(CH_2)_{14}CH_3$ |
| Aerothricin 78 | $NH_2$ | H | $NH_2$ | $CONH_2$ | NH | $CONH(CH_2)_{14}CH_3$ |
| Aerothricin 79 | $NH_2$ | H | $NHCONHCH_2CH_3$ | $CONH_2$ | NH | $CONH(CH_2)_{14}CH_3$ |
| Aerothricin 80 | $NH_2$ | H | $NHCOCH_3$ | $CONH_2$ | NH | $CONH(CH_2)_{14}CH_3$ |
| Aerothricin 81 | $NH_2$ | H | $NHCOCH_2NH_2$ | $CONH_2$ | NH | $CONH(CH_2)_{14}CH_3$ |
| Aerothricin 82 | $N(CH_3)_2$ | H | H | $CONH_2$ | NH | 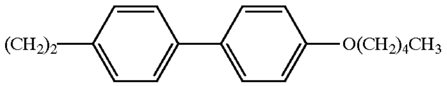 |
| Aerothricin 83 | $N(CH_3)_2$ | $CH_3$ | H | $CONH_2$ | NH | 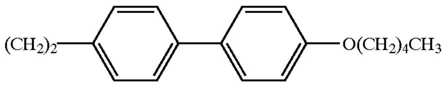 |
| Aerothricin 84 | $NH_2$ | $CH_3$ | H | $CONH_2$ | NH | 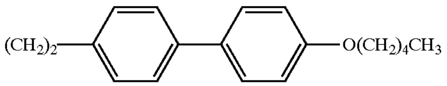 |

TABLE 1-continued
(I)
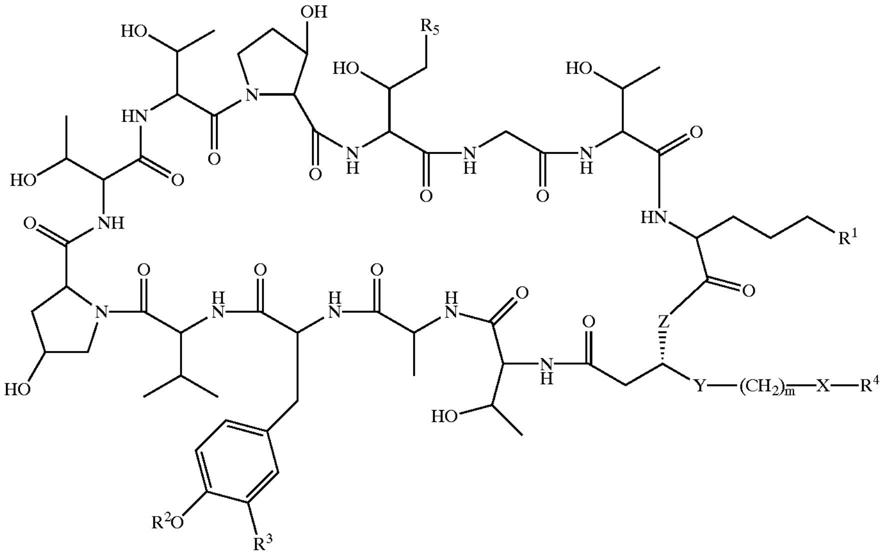
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 85 | $NH_2$ | $CH_3$ | $NO_2$ | $CONH_2$ | NH | 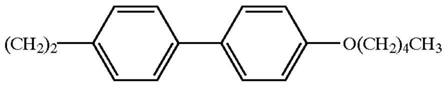 |
| Aerothricin 86 | $NH_2$ | $CH_3$ | $NO_2$ | $CONH_2$ | NH | 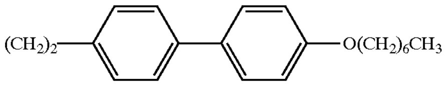 |
| Aerothricin 87 | $NH_2$ | $CH_3$ | H | $CONH_2$ | NH | 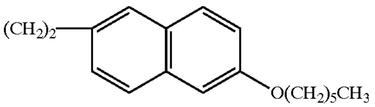 |
| Aerothricin 88 | $N(CH_3)_2$ | H | H | $CONH_2$ | NH | 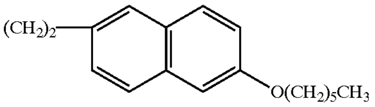 |

TABLE 1-continued
(I)
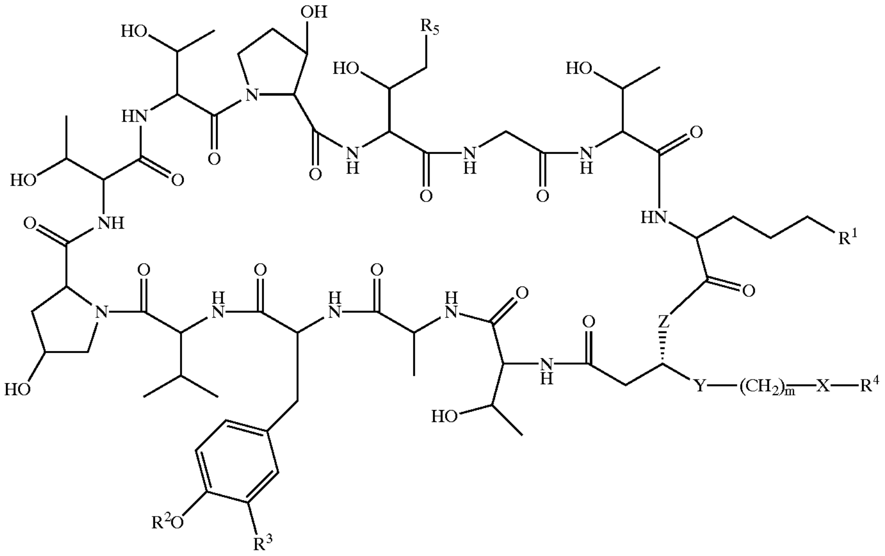
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 89 | $NH_2$ | H | H | $CONH_2$ | NH | 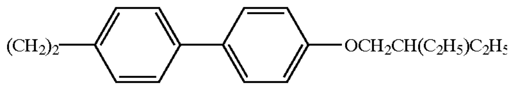 |
| Aerothricin 90 | $NH_2$ | H | H | $CONH_2$ | NH | 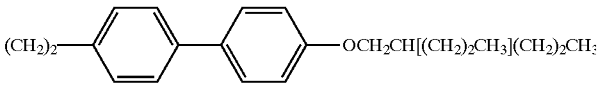 |
| Aerothricin 91 | $NH_2$ | H | H | $CONH_2$ | NH | 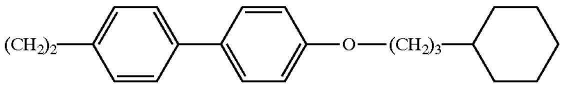 |
| Aerothricin 92 | $NH_2$ | H | H | $CONH_2$ | NH | 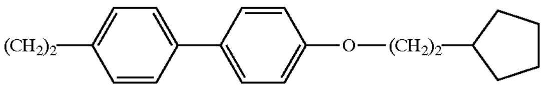 |

TABLE 1-continued
(I)
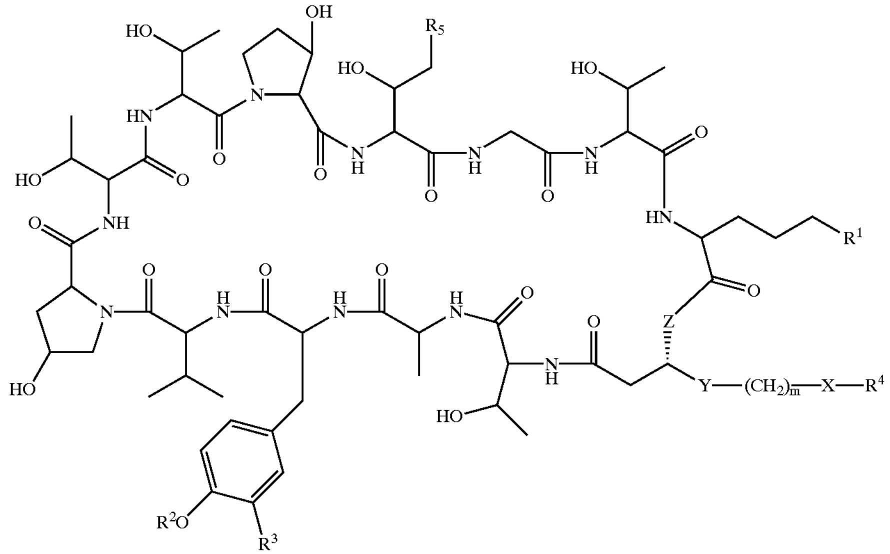
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 93 | $NH_2$ | H | H | $CONH_2$ | NH | 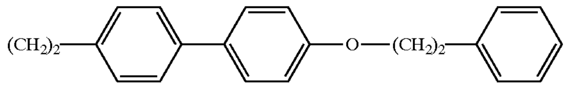 |
| Aerothricin 94 | $NH_2$ | H | H | $CONH_2$ | NH | 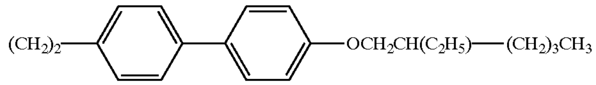 |
| Aerothricin 95 | $NH_2$ | H | H | $CONH_2$ | $NCH_3$ | $(CH_2)_{14}CH_3$ |
| Aerothricin 96 | $NH_2$ | H | $CO_2H$ | $CONH_2$ | O | $(CH_2)_{12}CH_3$ |
| Aerothricin 97 | $NH_2$ | H | H | $CONH_2$ | NH | 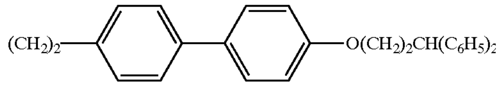 |

TABLE 1-continued
(I)
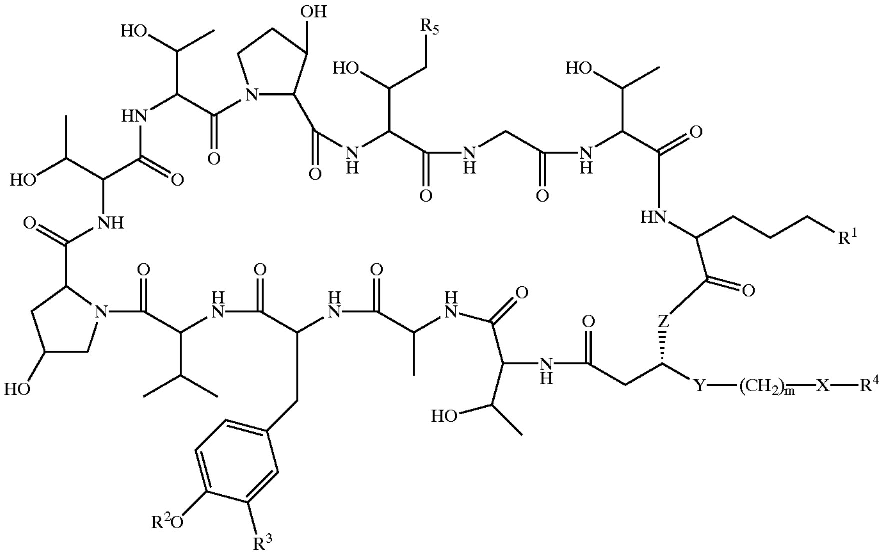
Formula (I)
| Compound name | $R^1$ | $R^2$ | $R^3$ | $R^5$ | Z | Y—$(CH_2)_m$—X—$R^4$ |
| --- | --- | --- | --- | --- | --- | --- |
| Aerothricin 98 | $NH_2$ | H | H | $CONH_2$ | NH | 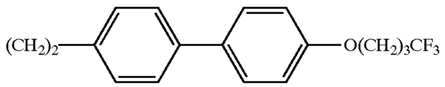 |
| Aerothricin 99 | $NH_2$ | H | H | $CONH_2$ | NH | 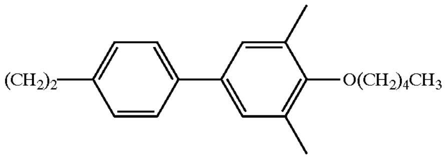 |
| Aerothricin 100 | bis(2-aminoethyl)-amino | H | H | $CONH_2$ | NH | 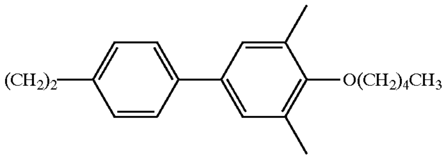 |

TABLE 1-continued (I)

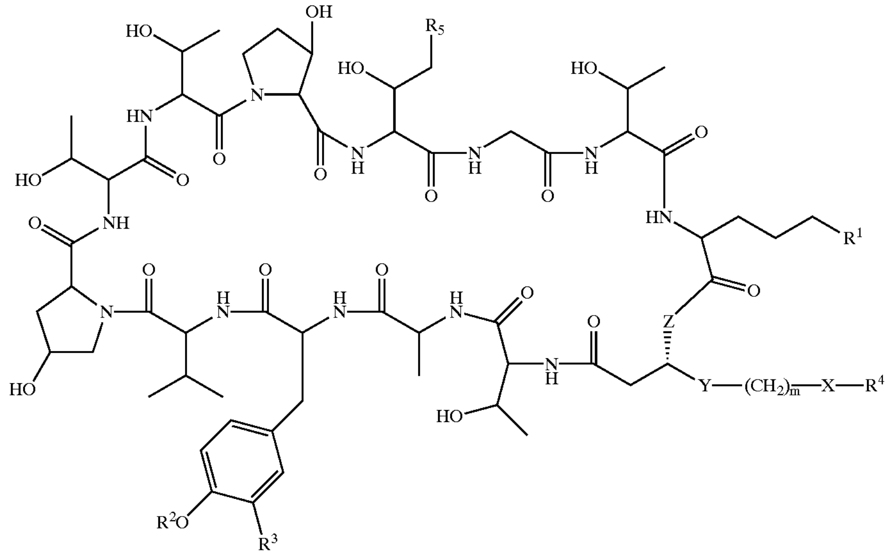

Formula (I)

| Compound name | $R^1$ | $R^2$ | $R^3$ | $R^5$ | Z | $Y-(CH_2)_m-X-R^4$ |
|---|---|---|---|---|---|---|
| Aerothricin 101 | L-ornitinylamino | H | H | $CONH_2$ | O | $(CH_2)_{12}CH_3$ |
| Aerothricin 102 | L-lysylamino | H | H | $CONH_2$ | O | $(CH_2)_{12}CH_3$ |
| Aerothricin 103 | L-argininylamino | H | H | $CONH_2$ | O | $(CH_2)_{12}CH_3$ |
| Aerothricin 104 | (2S)-(2,4-diamino-butyryl)amino | H | H | $CONH_2$ | O | $(CH_2)_{12}CH_3$ |
| Aerothricin 105 | (2S)-(2,3-diamino-propionyl)amino | H | H | $CONH_2$ | O | $(CH_2)_{12}CH_3$ |
| Aerothricin 106 | D-ornitinylamino | H | H | $CONH_2$ | O | $(CH_2)_{12}CH_3$ |
| Aerothricin 107 | D-lysylamino | H | H | $CONH_2$ | O | $(CH_2)_{12}CH_3$ |
| Aerothricin 108 | D-argininylamino | H | H | $CONH_2$ | O | $(CH_2)_{12}CH_3$ |
| Aerothricin 109 | (2R)-(2,4-diamino-butyryl)amino | H | H | $CONH_2$ | O | $(CH_2)_{12}CH_3$ |
| Aerothricin 110 | (2R)-(2,3-diamino-propionyl)amino | H | H | $CONH_2$ | O | $(CH_2)_{12}CH_3$ |
| Aerothricin 111 | bis(2-aminoethyl)-amino | H | H | $CONH_2$ | O | $(CH_2)_{12}CH_3$ |
| Aerothricin 112 | bis(3-aminopropyl)-amino | H | H | $CONH_2$ | O | $(CH_2)_{12}CH_3$ |
| Aerothricin 113 | (3-aminopropyl)-amino | H | H | $CONH_2$ | O | $(CH_2)_{12}CH_3$ |
| Aerothricin 114 | bis(2-piperazinyl-ethyl)amino | H | H | $CONH_2$ | O | $(CH_2)_{12}CH_3$ |
| Aerothricin 115 | [N-(2-aminoethyl)-N-(3-aminopropyl)]amino | H | H | $CONH_2$ | O | $(CH_2)_{12}CH_3$ |
| Aerothricin 116 | bis(2-guanidinyl-ethyl)amino | H | H | $CONH_2$ | O | $(CH_2)_{12}CH_3$ |
| Aerothricin 117 | (2-piperazinyl-ethyl)amino | H | H | $CONH_2$ | O | $(CH_2)_{12}CH_3$ |
| Aerothricin 118 | (2S)-(2-amino-4-triazol-1-ylbutyryl)amino | H | H | $CONH_2$ | O | $(CH_2)_{12}CH_3$ |

TABLE 1-continued (I)

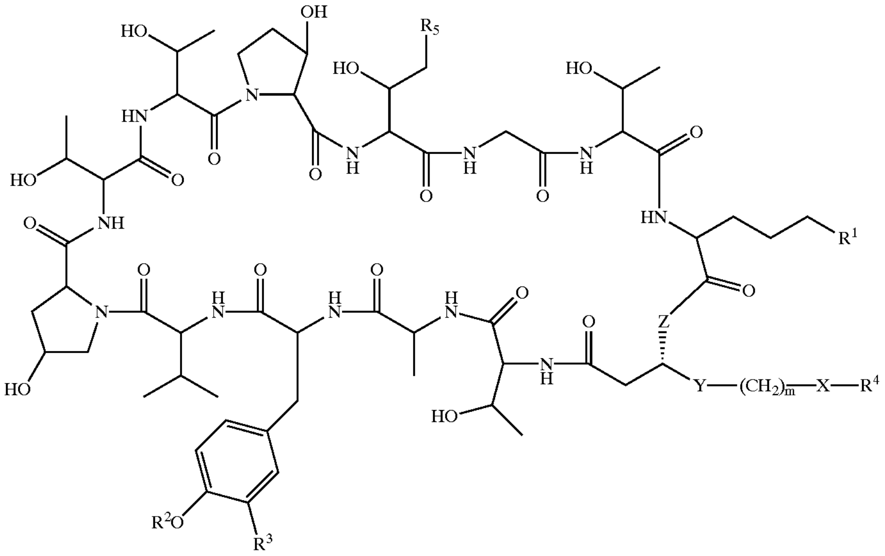

Formula (I)

| Compound name | $R^1$ | $R^2$ | $R^3$ | $R^5$ | Z | $Y—(CH_2)_m—X—R^4$ |
|---|---|---|---|---|---|---|
| Aerothricin 119 | L-histidylamino | H | H | $CONH_2$ | O | $(CH_2)_{12}CH_3$ |
| Aerothricin 120 | (2-cyanoethyl)-amino | H | H | $CONH_2$ | O | $(CH_2)_{12}CH_3$ |
| Aerothricin 121 | trimethyl-ammonio(iodide) | H | H | $CONH_2$ | O | $(CH_2)_{12}CH_3$ |
| Aerothricin 122 | $NH_2$ | $SO_3H$ | H | $CONH_2$ | O | $(CH_2)_{12}CH_3$ |
| Aerothricin 123 | $NH_2$ | H | H | $CONH_2$ | NH | 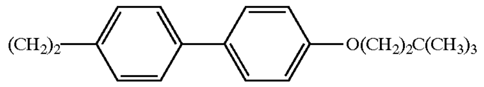 |
| Aerothricin 124 | 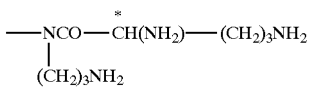 | H | H | $CONH_2$ | O | $(CH_2)_{12}CH_3$ |
| Aerothricin 125 | 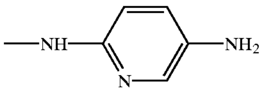 | H | H | $CONH_2$ | O | $(CH_2)_{12}CH_3$ |
| Aerothricin 126 | $—NHCH_2CH—(CH_2NH_2)_2$ | H | H | $CONH_2$ | O | $(CH_2)_{12}CH_3$ |

TABLE 1-continued
(I)
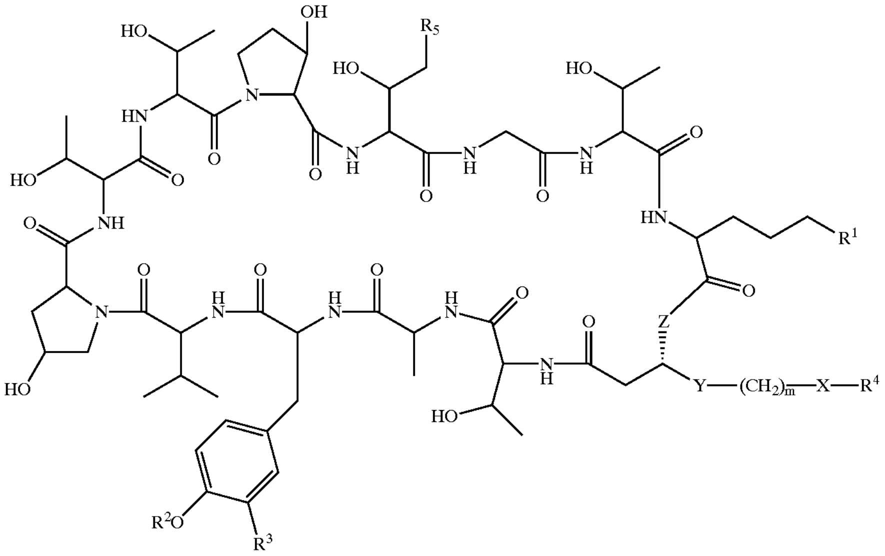
Formula (I)
| Compound name | $R^1$ | $R^2$ | $R^3$ | $R^5$ | Z | $Y-(CH_2)_m-X-R^4$ |
|---|---|---|---|---|---|---|
| Aerothricin 127 | $-NHCO-\overset{*}{C}H(CH_2)_3NH_2$ with $N(CH_2CH_2NH_2)_2$ | H | H | $CONH_2$ | O | $(CH_2)_{12}CH_3$ |
| Aerothricin 128 | $-NHCO-\overset{*}{C}H(CH_2)_3NH_2$ with $NHCO\overset{*}{C}H(CH_2)_3NH_2$ with $NH_2$ | H | H | $CONH_2$ | O | $(CH_2)_{12}CH_3$ |
| Aerothricin 129 | $-NHCO-\overset{*}{C}H(CH_2)_3NH_2$ with $NH(CH_2)_3NH_2$ | H | H | $CONH_2$ | O | $(CH_2)_{12}CH_3$ |

TABLE 1-continued
(I)
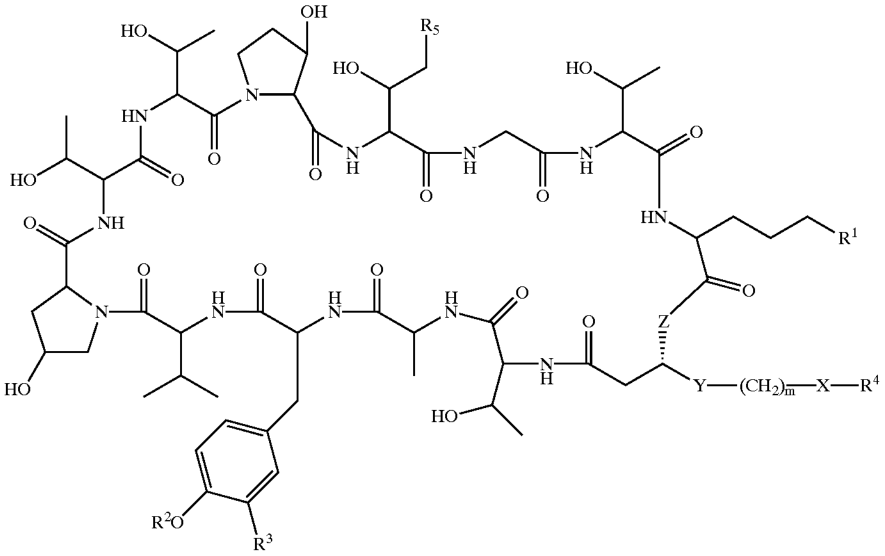
Formula (I)
| Compound name | R[1] | R[2] | R[3] | R[5] | Z | Y—(CH$_2$)$_m$—X—R[4] |
|---|---|---|---|---|---|---|
| Aerothricin 130 | 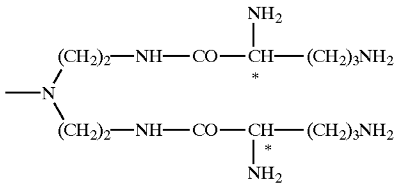 | H | H | $CONH_2$ | O | $(CH_2)_{12}CH_3$ |
| Aerothricin 131 | 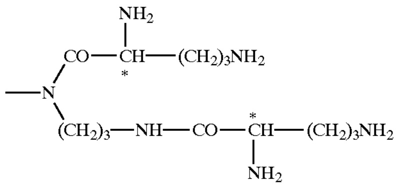 | H | H | $CONH_2$ | O | $(CH_2)_{12}CH_3$ |
*(R) configuration Particularly preferred are the Aerothricins selected from the group consisting of Aerothricins 2, 4 to 32, 63, 96–99, 101 to 131. Also particularly preferred are the Aerothricins selected from the group consisting of Aerothricins 14, 15, 21, 26–29, 63, 98, 99, 101–131.

Aerothricins represented by Formula (I) can be produced according to the following methods.

Process A

Aerothricins of the Formula (II) can be produced by cultivating a microorganism belonging to Deuteromycotina capable of producing Aerothricins 1, 2 and 3 [Aerothricin 3 (=WF11243) is described in Reference Example 1] under aerobic conditions in an aqueous or a solid medium and isolating Aerothricins 1, 2 and 3 from the culture.

(II)

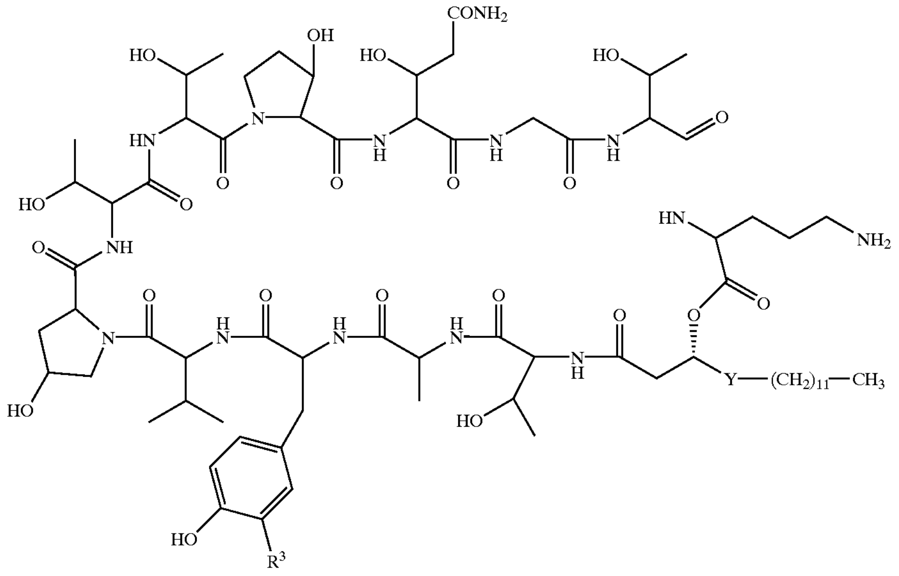

[wherein $R^3$ is hydrogen or hydroxy, Y is —$CH(CH_3)$— or —$CH_2$—]

Process B

Aerothricins of the Formula (I) [wherein $R^1$ is amino; Y is —CONH—, —CON(lower alkyl)-, —$CH_2$— or a single bond; Z is —NH— or —N(lower alkyl)-; $R^2$, $R^3$, $R^4$, $R^5$, X and m are as defined above] can be prepared by condensation of a compound of the Formula (III), (III)

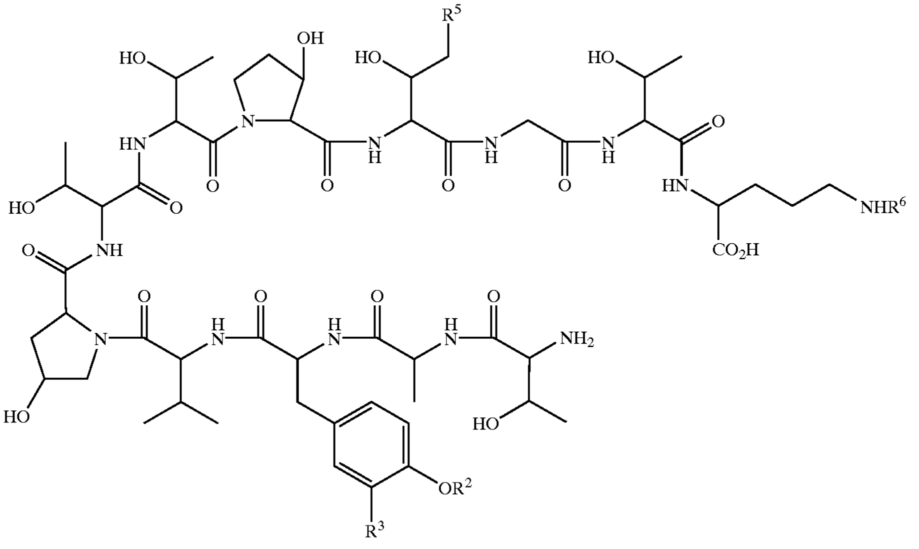

[wherein $R^6$ is an amino protecting group; $R^2$, $R^3$ and $R^5$ are as defined above], with a compound of the Formula (IV), (IV)

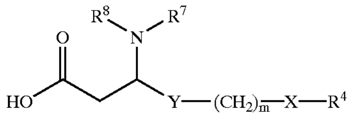

[wherein $R^7$ is an amino protecting group; $R^8$ is hydrogen or lower alkyl; $R^4$, X, Y and m are as defined above], using a carboxy activating agent for peptide synthesis, followed by selective removal of the amino protecting group $R^7$ of the resulting linear peptide, the successive cyclization with a carboxy activating agent for peptide synthesis, and removal of the amino protecting group $R^6$.

Process C

Aerothricins of the Formula (I) [wherein $R^3$ is a nitro group; $R^1$, $R^2$, $R^4$, $R^5$, X, Y, Z and m are as defined above] can be prepared by nitration of Aerothricins of the Formula (I) [wherein $R^3$ is hydrogen; $R^1$, $R^2$, $R^4$, $R^5$, X, Y, Z and m are as defined above].

Process D

Aerothricins of the Formula (I) [wherein $R^3$ is an amino group; $R^1$, $R^2$, $R^4$, $R^5$, X, Y, Z and m are as defined above] can be prepared by reduction of the nitro group of Aerothricins of the Formula (I) [wherein $R^3$ is a nitro group; $R^1$, $R^2$, $R^4$, $R^5$, X, Y, Z and m are as defined above].

Process E

Aerothricins of the Formula (I) [wherein $R^3$ is acylamino or (lower alkylcarbamoyl)amino; $R^1$, $R^2$, $R^4$, $R^5$, X, Y, Z and m are as defined above] can be prepared by acylation of the amino group of Aerothricins of the Formula (I) [wherein $R^3$ is an amino group; $R^1$, $R^2$, $R^4$, $R^5$, X, Y, Z and m are as defined above] with acid chloride, acid anhydride, carboxylic acid/condensation agent or lower alkylcarbamoyl chloride, followed, if necessary, by removal of the amino protecting group.

Process F

Aerothricins of the Formula (I) [wherein $R^1$ is (3-aminopropyl)amino, (2-cyanoethyl)amino, 3-amino-2-(aminomethy)propyl]amino or $—N(R^{15})—COCH[NH(CH_2)_3NH_2]—R^{13}$ [wherein $R^{13}$ and $R^{15}$ are as defined above] can be prepared by reacting the amino group of Aerothricins of Formula (I) [wherein $R^1$is an amino group or $—N(R^{15})—COCH(NH_2)—R^{13}$ [wherein $R^{13}$ and $R^{15}$ are as defined above]; $R^2$, $R^3$, $R^4$, $R^5$, X, Y, Z and m are as defined above] with acrylonitrile, ethoxymethylenemalononitrile or (1-ethoxyethylidene)malononitrile, followed by reduction of the resulting nitrile group(s) into amino group(s), and if necessary by removal of protecting group(s).

Process G

Aerothricins of the Formula (I) [wherein $R^1$ is $—N(R^{10})—R^{11}$ [wherein $R^{10}$ and $R^{11}$ are each independently selected from hydrogen, lower alkyl optionally substituted with one or more amino, guanidino, nitrogen containing heterocycle(s) or phenyl group(s) containing an amino, amidino or guanidino group] or $—N(R^{15})—CO—CH[N(R^{10})R^{11}]—R^{13}$ [wherein $R^{10}$ and $R^{11}$ are each a lower alkyl optionally substituted with one or more amino, amino-lower alkyl, guanidino, nitrogen containing heterocycle(s) or phenyl group(s) containing an amino, amidino or guanidino group; $R^{13}$ and $R^{15}$ are as defined above]; $R^2$, $R^3$, $R^4$, $R^5$, X, Y, Z and m are as defined above] can be prepared by reductive alkylation of the amino group of Aerothricins of the Formula (I) [wherein $R^1$ is amino, (2-cyanoethyl)amino or $—N(R^{15})—CO—CH[N(R^{10})R^{11}]—R^{13}$ [wherein $R^{10}$ and $R^{11}$ are each independently a hydrogen atom or (2-cyanoethyl)amino; $R^{13}$ and $R^{15}$ are as defined above]; $R^2$, $R^3$, $R^4$, $R^5$, X, Y, Z and m are as defined above] with an aldehyde of the Formula (V), $R^9—CHO$ (V)

[wherein $R^9$ is hydrogen, lower alkyl which may be further substituted with one or more protected amino, nitrogen containing heterocycle(s) or phenyl group(s) containing a protected amino group], followed, if necessary, by removal of amino protecting group(s) or reduction of a cyano group.

Process H

Aerothricins of the Formula (I) [wherein $R^1$ is $—N(R^{10})—R^{11}$ [wherein $R^{10}$ and $R^{11}$ are each independently selected from hydrogen or heteroaryl substituted with one or two amino group(s)]; $R^2$, $R^3$, $R^4$, $R^5$, X, Y, Z and m are as defined above] can be prepared by reacting the amino group of Aerothricins of the Formula (I) [wherein $R^1$ is an amino group; $R^2$, $R^3$, $R^4$, $R^5$, X, Y, Z and m are as defined above] with a compound of the Formula (VI), $R^{12}—Q$ (VI)

[wherein $R^{12}$ is a nitrogen containing heteroaryl which may be further substituted with a protected amino or nitro group, Q is a halogen atom such as chloro or bromo], followed, if necessary, by removal of an amino protecting group or reduction of a nitro group.

Process I-1

Aerothricins of the Formula (I) [wherein $R^1$ is

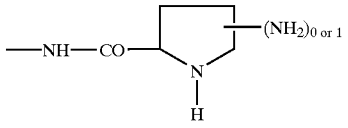

$—NHCO—CH(NH_2)—R^{13}$ [wherein $R^{13}$ is a residue derived from natural or unnatural amino acids] or $—NHCO—R^{14}$ [wherein $R^{14}$ is as defined above]; $R^2$, $R^3$, $R^4$, $R^5$, X, Y, Z and m are as defined above] can be prepared by acylation of the amino group of Aerothricins of the Formula (I) [wherein $R^1$ is an amino group; $R^2$, $R^3$, $R^4$, $R^5$, X, Y, Z and m are as defined above] with an acid of the Formula (VII) or (VII'), $HO(O{=})C—CH(NH—R^7)—R^{13}$ (VII)

(VII')

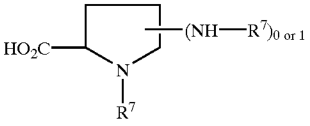

[wherein $R^{13}$ is a residue derived from natural or unnatural amino acids whose functional group is suitably protected, $R^7$ is an amino protecting group], or an acid of the Formula (VIII), $HO(O{=})C—R^{14}$ (VIII)

[wherein $R^{14}$ is lower alkyl having one or more protected amino group(s), nitrogen containing heterocycle(s) or phenyl group(s) containing protected amino group];

followed, if necessary, by removal of the protecting group (s).

Process I-2

Aerothricins of the Formula (I) wherein $R^1$ is

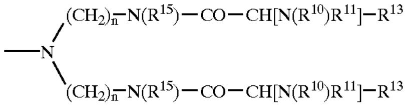

[wherein $R^{10}$, $R^{11}$, $R^{13}$, $R^{15}$, and m are as defined above], or

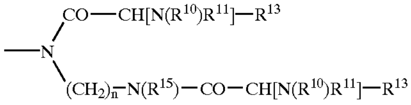

[wherein $R^{10}$, $R^{11}$, $R^{13}$, $R^{15}$, and m are as defined above] can be prepared by acylation of the amino group of Aerothricins of the Formula (I), wherein $R^1$ is —N($R^{10}$)—$R^{11}$ [wherein $R^{10}$ and $R^{11}$ are both lower alkyl substituted with an amino group] or —N($R^{15}$)—CO—CH[N($R^{10}$)$R^{11}$]—$R^{13}$ [wherein $R^{15}$ is lower alkyl substituted with an amino group; $R^{10}$, $R^{11}$, and $R^{13}$ are as defined in Claim 1 with the proviso that the amino group(s) present in $R^{10}$, $R^{11}$ and $R^{13}$ are protected], with an acid of the Formula (VII)

$$HO(O{=})C—CH(NH—R^7)—R^{13} \qquad (VII)$$

[wherein $R^{13}$ is a residue derived from natural or unnatural amino acids whose functional group is suitably protected, $R^7$ is an amino protecting group];

followed by removal of the protecting group(s).

Process J

Aerothricins of the Formula (I) [wherein $R^1$ is —N($R^{15}$)—CO—CH[N($R^{10}$)$R^{11}$]—$R^{13}$ [wherein $R^{10}$ and $R^{11}$ are hydrogen, $R^{13}$ is as defined above and $R^{15}$ is lower alkyl optionally substituted with one or more amino, guanidino, nitrogen containing heterocycle(s) or phenyl group(s) containing an amino, amidino or guanidino group],

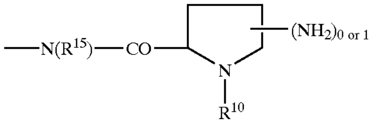

[wherein $R^{10}$ is hydrogen and $R^{15}$ is lower alkyl optionally substituted with one or more amino, guanidino, nitrogen containing heterocycle(s) or phenyl group(s) containing an amino, amidino or guanidino group], or —N($R^{15}$)—CO—$R^{14}$ [wherein $R^{15}$ is lower alkyl optionally substituted with one or more amino, guanidino, nitrogen containing heterocycle(s) or phenyl group(s) containing an amino, amidino or guanidino group, $R^{14}$ is as defined above]; $R^2$, $R^3$, $R^4$, $R^5$, X, Y, Z and m are as defined above] can be prepared by mono N-alkylation of the amino group of Aerothricins of the Formula (I) [wherein $R^1$ is an amino group; $R^2$, $R^3$, $R^4$, $R^5$, X, Y, Z and m are as defined above] as described in process F, followed by acylation with a corresponding compound of the Formula (VII), (VII') or (VIII) as described in the process I, followed, if necessary, by removal of the protecting group(s).

Process K

Aerothricins of the Formula (I) [wherein $R^1$ is a guanidino group, —N($R^{10}$)—$R^{11}$ [wherein $R^{10}$ and $R^{11}$ are each independently selected from lower alkyl substituted with guanidino or phenyl group(s) containing a guanidino group], —N($R^{15}$)—CO—CH[N($R^{10}$)$R^{11}$]—$R^{13}$ [wherein $R^{10}$, $R^{11}$ and $R^{13}$ are as defined above and $R^{15}$ is lower alkyl optionally substituted with one or more guanidino group(s), nitrogen containing heterocycle(s) or phenyl group(s) containing a guanidino group] or —N($R^{15}$)CO—$R^{14}$ [wherein $R^{14}$ is lower alkyl substituted with one or more guanidino group(s), nitrogen containing heterocycle(s) or phenyl group (s) containing a guanidino group; $R^2$, $R^3$, $R^4$, $R^5$, X, Y, Z and m are as defined above] can be prepared by reacting Aerothricins of the Formula (I) [wherein $R^1$ is an amino group; —N($R^{10}$)—$R^{11}$ [wherein $R^{10}$ and $R^{11}$ are each independently selected from lower alkyl substituted with amino group(s) or phenyl group(s) containing an amino group], —N($R^{15}$)—CO—CH[N($R^{10}$)$R^{11}$]—$R^{13}$ [wherein $R^{10}$,$R^{11}$ and $R^{13}$ are as defined above and $R^{15}$ is lower alkyl optionally substituted with one or more amino group(s), nitrogen containing heterocycle(s) or phenyl group(s) containing an amino group]; or —NHCO—$R^{14}$ [wherein $R^{14}$ is lower alkyl substituted with one or more amino group(s), nitrogen containing heterocycle(s) or phenyl group(s) containing an amino group; $R^2$, $R^3$, $R^4$, $R^5$, X, Y, Z and m are as defined above] with an activated amidine derivative.

Process L

Aerothricins of the Formula (I) [wherein $R^2$ is lower alkyl or lower alkenyl optionally substituted with acyl, carboxy, carbamoyl, hydroxy, amino, mono-lower alkylamino or di-lower alkylamino; $R^1$, $R^3$, $R^4$, $R^5$, X, Y, Z and m are as defined above] can be prepared by 0-alkylation of the phenolic hydroxyl group of Aerothrricins of the Formula (I) [wherein $R^2$ is hydrogen; $R^1$, $R^3$, $R^4$, $R^5$, X, Y, Z and m are as defined above] with an alkylating agent.

Process M

Aerothricins of the Formula (I) [wherein $R^3$ is carboxyl, lower alkoxycarbonyl, lower alkyl, alkenyl or alkynyl which may be optionally substituted with hydroxy, amino, mono-lower alkylamino, di-lower alkylamino, lower alkoxycarbonyl or carbamoyl; $R^2$ is hydrogen; $R^1$, $R^4$, $R^5$, X, Y, Z and m are as defined above] can be prepared by iodination of Aerothricins of the Formula (I) [wherein $R^2$ and $R^3$ are hydrogen; $R^1$, $R^4$, $R^5$, X, Y, Z and m are as defined above] with an iodination agent, followed by palladium(0) catalyzed coupling of the resulting iodo derivative of the Formula (I) [wherein $R^3$ is an iodo; $R^1$, $R^2$, $R^4$, $R^5$, X, Y, Z and m are as defined above] with carbon monoxide, methyl acrylate and the like, and if necessary, by removal of the protecting group(s).

Process N

Aerothricins of the Formula (I) [wherein $R^5$ is —CN; $R^1$, $R^2$, $R^3$, $R^4$, X, Y, Z and m are as defined above] can be prepared by dehydration of the carbamoyl group of Aerothricins of the Formula (I) [wherein $R^5$ is —$CONH_2$; $R^1$, $R^2$, $R^3$, $R^4$, X, Y, Z and m are as defined above] with a dehydrating agent, and if necessary, by removal of the amino protecting group(s).

Process O

Aerothricins of the Formula (I) [wherein $R^5$ is —$CH_2NH_2$; $R^1$, $R^2$, $R^3$, $R^4$, X, Y, Z and m are as defined above] can be prepared by reduction of the carbamoyl or cyano group of Aerothricins of the Formula (I) [wherein $R^5$ is —$CONH_2$ or —CN; $R^1$, $R^2$, $R^3$, $R^4$, X, Y, Z and m are as defined above] with a reducing agent, and if necessary, by removal of the amino protecting group(s).

Process P

Aerothricins of the Formula (I) [wherein $R^2$ is hydroxysufonyl; $R^1$, $R^3$, $R^4$, $R^5$, X, Y, Z and m are as defined above] can be prepared by hydroxysulfonation of the tyrosine residue of Aerothricins of the Formula (I) [wherein $R^2$ is hydrogen; $R^1$, $R^3$, $R^4$, $R^5$, X, Y, Z and m are as defined above], followed by removal of protecting group(s).

Process Q

Aerothricins of the Formula (I) [wherein —Y—(CH$_2$)m-X—$R^4$ is n-tridecanyl or 1-methytridecanyl, $R^5$ is —$CONH_2$, Z is an oxygen atom and $R^1$, $R_2$, and $R^3$ are as defined above] can be prepared from the linear peptide of the Formula (IX) by the method outlined in Scheme 1.

The compound of above formula (III), wherein $R^2$, $R^3$ and $R^5$ are as defined above and $R^6$ is an amino protecting group, with the proviso that when $R^5$ is —$CONH_2$, then $R^2$ or $R^3$ are other than hydrogen, and salts thereof are new and are also subject of the present invention. Furthermore, the linear peptides of Formulas (IX), (X) and (XII) shown in Scheme 1 and optionally salts thereof are new and are also subject of the present invention.

scheme 1
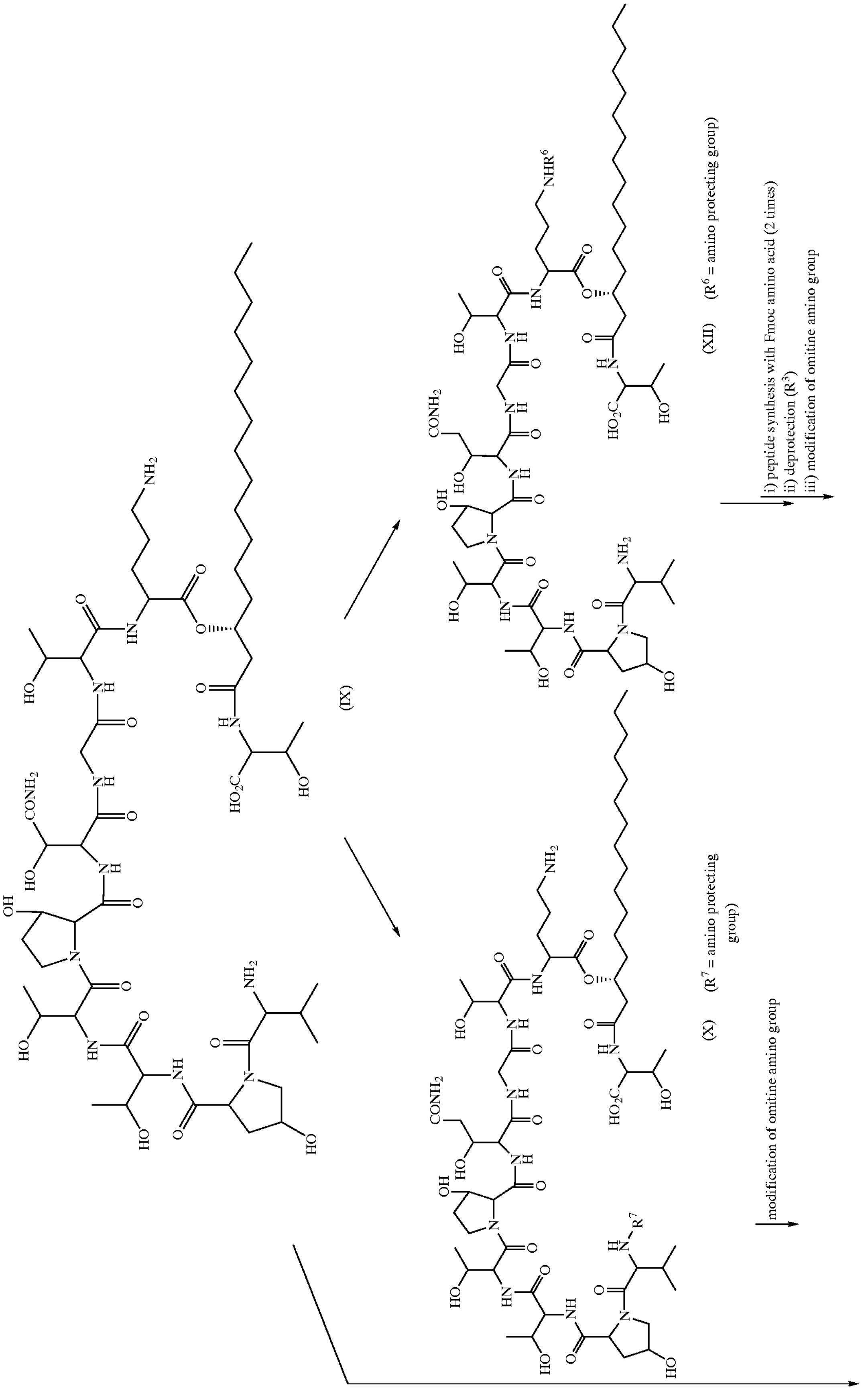
(IX)
(X) ($R^7$ = amino protecting group)
(XII) ($R^6$ = amino protecting group)

-continued
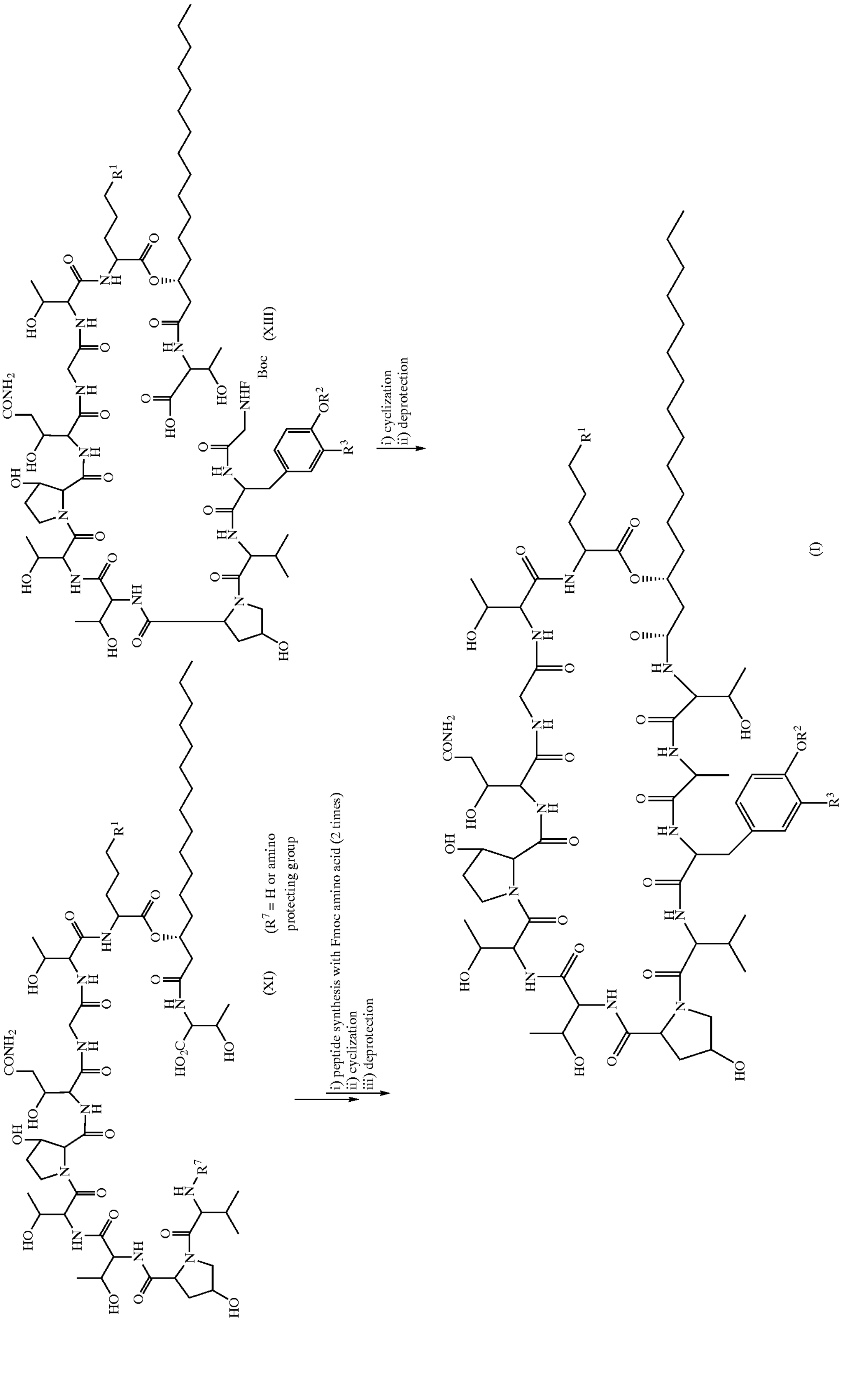
(XI)
(XIII)
(I)

The Processes A to Q can be illustrated in more detail as follows:

Process A

The microorganism used in the present invention can be any strains including mutants and variants belonging to Deuteromycotina capable of producing Aerothricins 1, 2 and 3. Especially preferred is strain NR 7379 which was isolated from fallen leaves collected at Kagoshima pref. in Japan, and identified as a strain belonging to Deuteromycotina.

The cultural and morphological characteristics of strain NR 7379 are as follows:

1. Cultural characteristics

Corn meal agar (CMA): Growth was not extensive. The colonies reached 11 mm in diameter from inoculum (4.5 mm diam. agar plug) after 14 days at 25° C. They were plane and pale cream yellow. The reverse side was pale cream yellow. Colorless and mucilaginous exudates were present.

Miura's medium (LCA): Growth was not extensive. The colonies reached 11 mm in diameter from inoculum after 14 days at 25° C. They were plane and pale cream yellow. The reverse side was pale cream yellow. Exudates were absent.

Malt extract agar (MEA): Growth was not extensive. The colonies were pustuliform and attained a diameter of 18 mm from inoculum after 14 days at 25° C. The color of colonies was light yellowish brown. The reverse side was of the same color. Exudates were colorless and mucilaginous.

Potato-dextrose agar (PDA): Growth was not extensive. The colonies were pustuliform and reached 14 mm in diameter from inoculum after 14 days at 25° C. The color and texture of colonies were similar to those on MEA. Exudates were colorless and mucilaginous.

Germination was observed between 5° C. and 30° C. on CMA, LCA, MEA, and PDA.

2. Morphological characteristics

Mycelia were partly immersed, partly superficial, branched, septate, and pale brown to cream yellow. Conidiophores were formed from immersed mycelium. They were hyaline, septate, branched, irregular. Conidiogenous cells were on distinct conidiophores or irregular hyphae. They were enteroblastic, phialidic, terminal or subterminal. Terminal or subterminal phialides were variable in length and shape. They were cylindrical to lageniform and their length and width were up to 5.5 to 10 $\mu$m and 2.5 to 5.5 $\mu$m respectively. Irregularly filiform Conidiophores with lateral conidiogenous cells immediately below septa were often formed. Conidia were one-celled, hyaline, smooth, globose to subglobose, 2.0 to 5.5 $\mu$m in length and 2.0 to 5.0 $\mu$m in width.

On the basis of these distinct cultural and morphological characteristics, the present strain belonged to Deuteromycotina designated as Deuteromycotina NR 7379.

The strain denoted as Deuteromycotina NR 7379 has been deposited with the National Institute of Bioscience and Human-Technology, Agency of Industrial Science and Technology, Japan in the name of Nippon Roche K. K., of 6-1, Shiba 2-chome, Minato-ku Tokyo, 105 Japan on Jun. 16, 1998 under the Budapest Treaty as follows: Deuteromycotina NR 7379 (FERM BP-6391).

The cultivation in accordance with the process provided by the present invention can be carried out in a culture medium which contains customary nutrients usable by the microorganism being cultivated. As carbon sources there can be mentioned, for example, glucose, sucrose, starch, glycerol, molasses, dextrin and mixtures thereof. Nitrogen sources are, for example, soybean meal, cottonseed meal, meat extract, peptone, dried yeast, yeast extract, corn steep liquor, ammonium sulfate, sodium nitrate and mixtures thereof. Moreover, there may be added to the culture medium other organic or inorganic substances for promoting the growth of the microorganism and for increasing the production of Aerothricin 1. Examples of such substances are inorganic salts, such as calcium carbonate, sodium chloride, phosphates and the like.

The cultivation is carried out under aerobic conditions preferably in a liquid medium by submerged fermentation, or in a solid medium by static fermentation. A temperature of 20° C. to 30° C., with an optimal temperature of 27° C. is suitable for cultivation. The cultivation is preferably carried out at a pH of 3 to 9. The cultivation time depends on the conditions under which the cultivation is carried out. In general, it is sufficient to carry out the cultivation for 20 to 360 h.

For harvesting the objective Aerothricins 1, 2 and 3 from the cultures, separation methods which are usually employed to isolate metabolites produced by microbes from their cultures can be properly used. For example, Aerothricin 1, which is a methanol extractable amphoteric substance, is recovered advantageously by the following procedures.

That is, the whole culture solid obtained by solid state fermentation is extracted with an appropriate solvent to recover the proposed product. The solvents which can be used to extract the objective compound from the whole cultured solid include water-soluble organic solvents or hydrous solutions of water-soluble organic solvents, such as methanol, ethanol and hydrous alcohols.

For removing salts, water soluble substances, etc. from the resulting extract, use is made of, with advantage, solvent partition between water and water-immiscible organic solvents, such as n-butanol, ethyl acetate, etc. For removing coloring substances, fat-soluble substance or the like from the extract, use is made of, with advantage, solvent purification by methanol, ethanol, a mixture of acetonitrile-0.1% aqueous trifluoroacetic acid, etc.

For complete purification of Aerothricins, column chromatography is used with advantage. Carriers which can be used in such a column chromatography are such as YMC-GEL ODS (Yamamura Chemical Laboratories, Japan) or Preparative C18 (Waters Millipore Corporation). As an eluent, use is made of a solvent system consisting a mixture of aqueous trifluoroacetic acid and appropriate water-soluble organic solvents such as methanol, ethanol, acetonitrile, etc. The eluate fraction thus purified, which contains each component, can be subjected to concentration or freeze-drying to pulverize Aerothricins 1, 2 and 3.

Aerothricins 1, 2 and 3 were isolated as a trifluoroacetic acid salt, but the free Aerothricins 1, 2 and 3 can be prepared by the following procedure. Namely, Aerothricins 1, 2 and 3 trifluoroacetic acid salt are dissolved in water, to which was added one equivalent of sodium hydroxide, and the mixture is subjected to Sephadex LH-20 column Chromatography, followed by elution with a hydrous alcohol such as methanol-water, etc. to thereby obtain Aerothricins 1, 2 and 3 (free form), respectively.

Process B

The starting compound of the Formula (III) can be prepared from Aerothricins of the Formula (I) [which includes Aerothricins 1 to 3 as well as those converted from Aerothricins 1 to 3 by use of a process selected from the processes C to Q] by the method similar to that described in WO 96/30399. This method comprises alkaline hydrolysis of the lactone ring followed by enzymatic cleavage of the fatty acid chain. The preferable amino protecting groups for $R^6$ in the Formula (III) and $R^8$ in the Formula (IV) are tert-butoxycarbony (Boc) and 9-fluorenylmethyloxycarbonyl (Fmoc), respectively.

The starting compound of the Formula (III) can also be prepared from the linear peptide of the Formula (IX), obtained by fermentation of Deuteromycotina, by conventional peptide synthesis mentioned herein after.

The starting compound of the Formula (IV) [wherein Y is —CONH—; $R^4$, $R^8$, and X are as defined above] can be prepared by condensation of the compound of the Formula (XIV), (XIV)

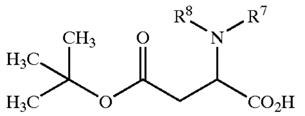

[wherein $R^7$ is an amino protecting group, such as a Fmoc group, and $R^8$ is as defined above], with a compound of the Formula (XV), $R^8NH—(CH_2)_m—X—R^4$ (XV)

[wherein $R^4$, $R^8$, X and m are as defined above], followed by removal of the tert-butyl group. The compound of the Formula (XIV) is commercially available.

The starting compounds of the Formula (XV) [wherein X is a single bond, aryl, biphenyl or terphenyl group optionally containing one or more hetero atom(s) and/or being substituted with halogen atom(s) or lower alkyl] are commercially available or can be prepared by the methods similar to those described in EP 736 541 and Scheme 2: for example, $LiAlH_4$ reduction of the carboxyamnide prepared from the carboxylic acid intermediates in Scheme 2 mentioned herein after, followed by protection of amino group with Fmoc chloride and the like.

The representative compounds of the Formula (IV) [wherein Y is —CONH— or —CON(lower alkyl)-; $R^4$, $R^7$, $R^8$ and X are as defined above] are The starting compound of the Formula (IV) [wherein Y is a single bond or $—CH_2—$;, $R^4$, $R^8$, and X are as defined above] can be prepared by Michael addition of (R)-(+)-N-benzyl-1-phenylethylamnine to a compound of the Formula (XVI), (XVI)

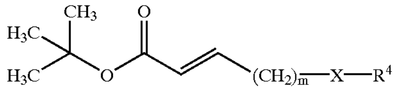

[wherein $R^4$, X and m are as defined above]

in the presence of strong base such as LDA [cf. Tetrahedron Asymmetry, 2 (3), 183 (1991)], followed by i) N-debenzylation by catalytic hydrogenation, ii) protection of the resulting primary amine with Fmoc chloride and the like, and iii) removal of tert-butyl group.

The starting compounds of the Formula (XVI) can be prepared by the method outlined in the following Scheme 2.

Scheme 2

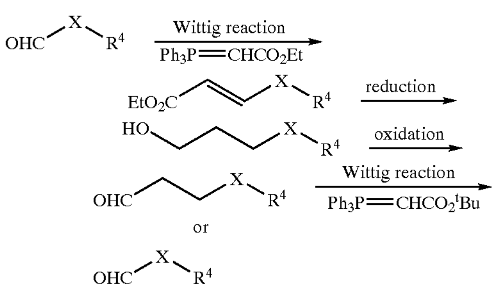

$HO_2C—CH_2CH(NHFmoc)—CONH—(CH_2)_{10}CH_3$, $HO_2C—CH_2CH(NHFmoc)—CONH—(CH_2)_{12}CH_3$, $HO_2C—CH_2CH(NHFmoc)—CONH—(CH_2)_{14}CH_3$, $HO_2C—CH_2CH(NHFmoc)—CONH—(CH_2)_{11}CH(CH_3)_2$, $HO_2C—CH_2CH(NHFmoc)—CONH—(CH_2)_{10}—CH{=}CH—CH_2CH_3$, $HO_2C—CH_2CH(NHFmoc)—CONH—(CH_2)_8—CH{=}CH—(CH_2)_3CH_3$,

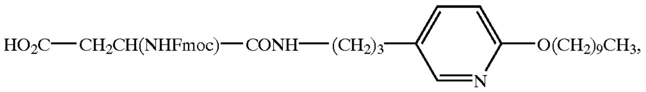

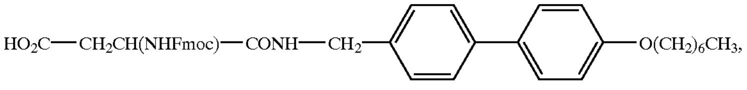

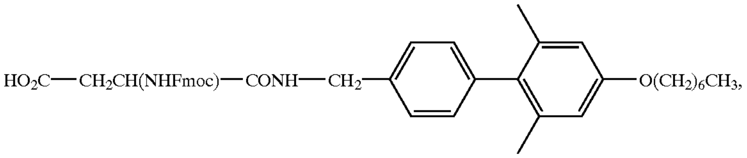

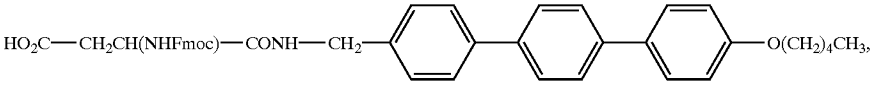

$HO_2C—CH_2CH(NHFmoc)—CON(CH_3)—(CH_2)_{12}CH_3$, $HO_2C—CH_2CH(NHFmoc)—CON(CH_3)—(CH_2)_{14}CH_3$, and the like.

-continued
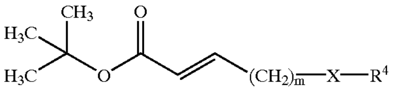
(XVI)
The compounds of the Formula (XVI), wherein m is 4, can be prepared by repeating the steps 1 to 3 in Scheme 2 before the last Wittig reaction.
The representative compounds of the Formula (IV) [wherein Y is a single bond or $—CH_2—$; $R^4$, $R^7$, and X are as defined above] are:
$HO_2C—CH_2CH(NHFmoc)—(CH_2)_{12}CH_3$,
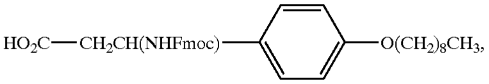
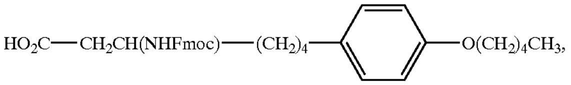
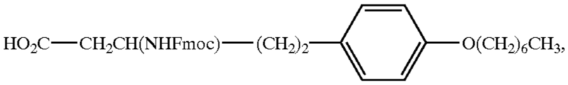
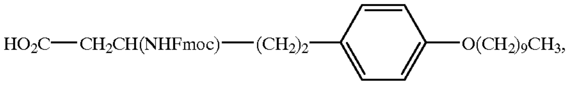
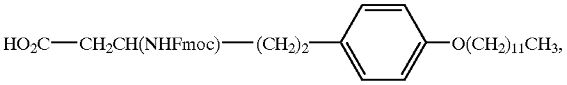
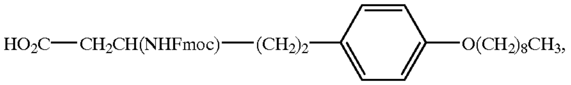
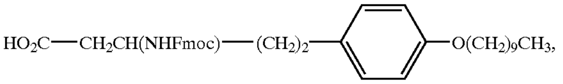
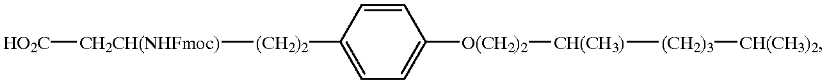
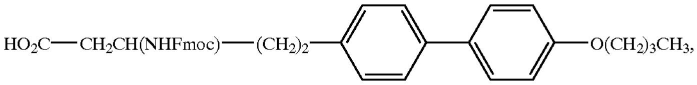
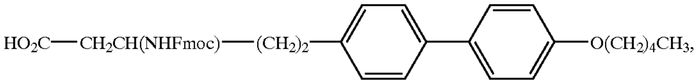
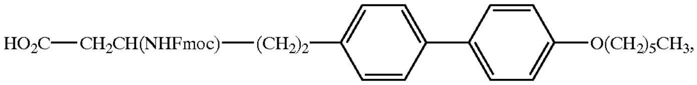
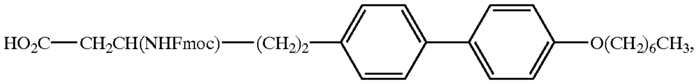
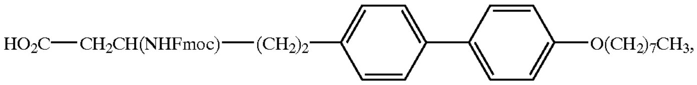
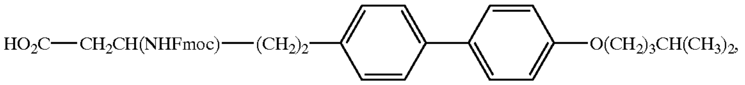
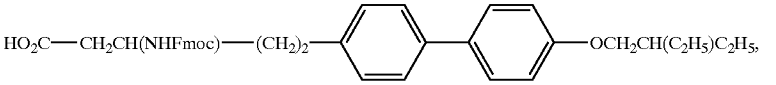
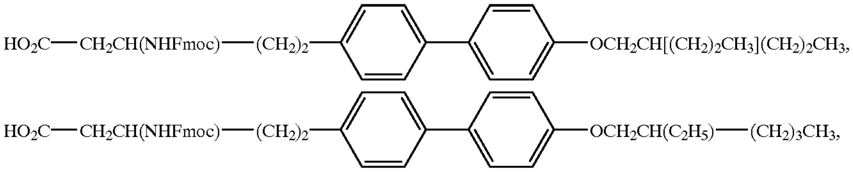
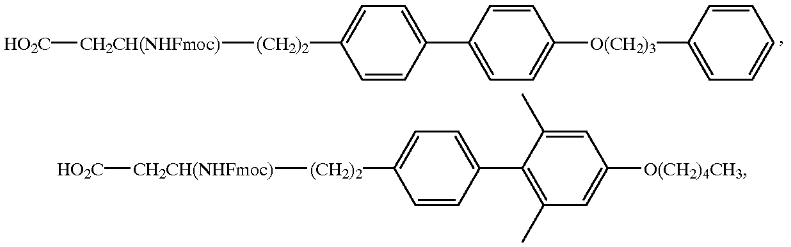

-continued

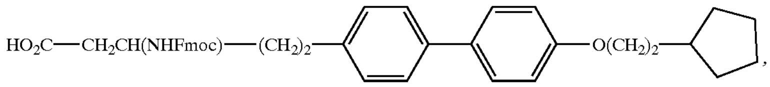
,

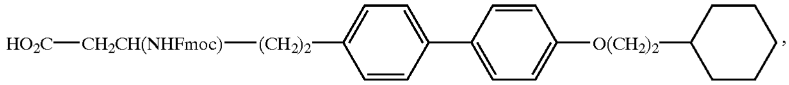
,

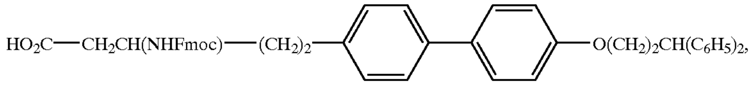
,

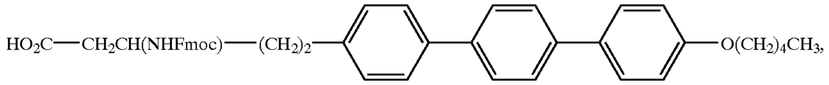
,

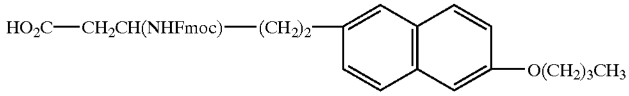

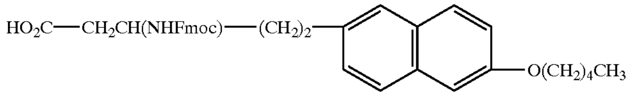

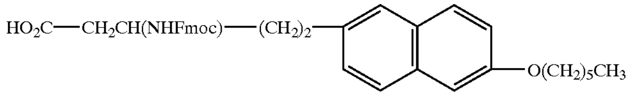

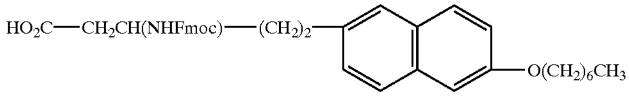

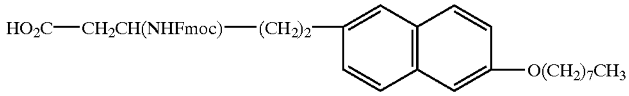

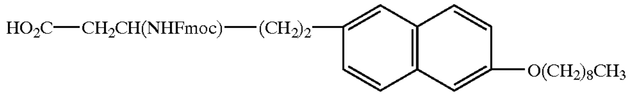

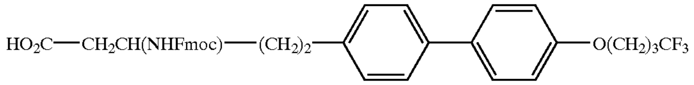

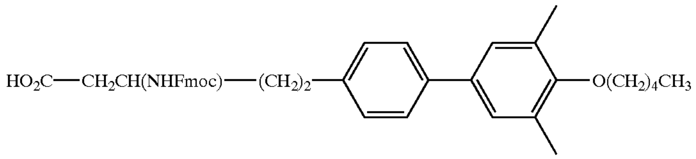

$HO_2C—CH_2CH(N(CH_3)Fmoc)—(CH_2)_{14}CH_3$ and the like.

The first peptide bond formation reaction as well as the cyclization of the resulting linear peptide can be performed by the method known to those skilled in the peptide chemistry [cf. The practice of Peptide Synthesis, M. Bodansky and A. Bodansky/2nd ed., 1994 (Springer-Verlag)]. The preferable condensation agent is BOP-HOBt, PyBOP™-HOBt, PyBroP™-HOBt and the like [coupling reagents: commercially available (cf. The Combinatorial Chemistry Catalog, February, 1997; Novabiochem.)].

The reaction can be carried out in a solvent such as methanol, ethanol, pyridine, N,N-dimethylformamide, N-methylpyrrolidone and the like in the presence or absence of a base such as triethylamine, di-isopropylethylamine, pyridine and the like at a temperature between −20° C. and +50° C., preferably at 0° C. to +25° C.

Process C

Nitration of the Aerothricin of the Formula (I) can be performed by the method known to those skilled in the art; typically by sodium nitrite/acetic acid, tetranitromethane/pyridine and the like.

The reaction can be carried out at a temperature between −20° and 0° C., preferably at 0° C.

Process D

Reduction of nitro group(s) can be done by the method known to those skilled in the art; typically by catalytic hydrogenation using a catalyst such as palladium-C, platinum oxide and the like.

The reaction can be carried out at room temperature in a solvent such as methanol, ethanol, acetic acid, and the like.

Processes E and I

N-acylation of an amino group existing in $R^1$ or $R^3$ of the Formula (I) can be done with acid anhydride or carbamoyl chloride by the method known to those skilled in the art, or with carboxylic acid using condensation agents such as dicyclohexylcarbodiimide, BOP, HBTU, TNTU, PyBroP™, PyBOP™, TBTU, TSTU, HOBt and the like, or the combination of two of them.

The reaction can be carried out in a solvent such as methanol, ethanol, pyridine, N,N-dimethylformamide, N-methylpyrrolidone and the like in the presence or absence of a base such as triethylamine, di-isopropylethylamine, pyridine and the like at a temperature between −20° C. and +50° C., preferably at 0° C. to +25° C.

The removal of the amino protecting group, when using N-protected amino acid for the condensation reaction, can be done by the method known to those skilled in the art, e.g. treatment with trifluoroacetic acid for Boc group, or piperidine for Fmoc group.

Process F

N-monoalkylation of an amino group existing in $R^1$ of the Formula (I) can be done using acrylonitrile, ethoxymethylene-malononitrile or (1-ethoxyethylidene) malononitrile according to the method described in Organic Synthesis col. Vol. 111, page 93, followed by reduction of the resulting nitrile group by catalytic hydrogenation or reduction with sodium borohydride/cobalt chloride, borane-methylsulide complex and the like [cf. J. Med. Chem., 37, 222 (1994)].

Process G

N-alkylation of the primary or secondary amino group existing in $R^1$ of the Formula (I) can be done by the conventional reductive alkylation with aldehyde derivatives of the Formula (V) using a reducing agent such as sodium cyanoborohydride in the presence or absence of weak acid such as acetic acid.

The reaction can be carried out at room temperature in a solvent such as methanol, ethanol, acetic acid and the like.

Process H

Examples of the compound ($R^{12}$-Q) of Formula (VI) for the substitution reaction are 2-bromo-5-nitropyridine, 2-chloropyrimidine, chloropyrazine and the like.

The substitution reaction can be carried out at a temperature between −20° C. and +50° C., preferably at 0° C. to +25° C., in a solvent such as acetonitrile, N,N-dimethylformamide and the like in the presence or absence of acid scavenger such as potassium carbonate, triethylamine, di-isopropylethyamine and the like.

Process J

The first mono-N-alkylation of an amino group existing in $R^1$ of the Formula (I) can be done by the method described in Process F. The successive N-acylation can be done by the method described in Process E and I.

Process K

The conversion of an amino group existing in $R^1$ of the Formula (I) into a guanidino group can be done by an activated amidine derivative such as 3,5-dimethyl-lH-pyrazole-1-carboxamidine, formamidinesulfonic acid, benztriazol-1-carboxamidinium tosylate and the like.

The reaction can be carried out in a solvent such as methanol, ethanol, water, N,N-dimethylformamide and the like at a temperature between 0° C. and ~50° C., preferably at 20° C. to ~30° C.

Process L

O-alkylation of a hydroxy group of the tyrosine residue in the Formula (I) can be done by the method known to those skilled in the art in the presence of acid scavenger such as sodium carbonate, diisopropylethylamine and the like [Can. J. Chem., 36, 1521 (1958)].

The reaction can be carried out in a solvent such as methanol, ethanol, acetone, N,N-dimethylformamide and the like at a temperature between 0° C. and +50° C., preferably at 0° C. to +25° C.

Process M

Iodination at the ortho position of the phenol group in a tyrosine residue can be done by treatment of Aerothricins of the Formula (I), wherein $R^2$ is hydrogen, with iodine monochloride or sodium iodide/aqueous sodium hypochlorite in a solvent such as methanol, ethanol and the like at room temperature.

The palladium(O) catalyzed coupling reaction with carbon monoxide, methyl acrylate and the like can be carried out using a palladium(0) catalyst such as $Pd(OAc)_2$, $Pd(OAc)_2(dppp)_2$ in a solvent such as methanol, ethanol, N,N-dimethylformamide, acetonitrile and the like in the presence of base such as triethylamine at a temperature between 20° C. and +100° C., preferably at 20° C. to +70° C. [Bioorg. Med. Chem. Lett., 7 (22), 2879 (1997)].

Process N

Dehydration of the carbamoyl group ($R^5$) of the Formula (I) can be done by Burgess reagent [available from Aldrich], cyanuric chloride, oxalyl chloride and the like [cf. J. Med. Chem., 37, 222 (1994)].

The reaction can be carried out in a solvent such as N,N-dimethylformamide, N-methylpyrrolidone and the like at room temperature.

Process O

The reduction of the carbamoyl or cyano group ($R^5$) of the Formula (I) can be done by sodium borohydride/cobalt chloride, borane-methylsulfide complex and the like [cf. J. Med. Chem., 37, 222 (1994)].

The reaction can be carried out in a solvent such as methanol, ethanol and the like at room temperature.

Process P

The hydroxysulfonation of the tyrosine residue of the Formula (I) can be carried out by sulfurtrioxide-DMF complex, sulfurtrioxide-pyridine complex or sulfurtrioxide-triethylamine complex in a solvent such as N,N-dimethylformamide, N-methylpyrrolidone, 1,4-dioxane, tetrahydrofuran and the like at a temperature between −30 to +70 ° C., preferably at room temperature [ cf. J. Chem. Soc. Perkin Trans, (6) 1739 (1990)].

Process Q

The reactions involved in this process can be done by the methods similar to those described in the process B—O.

The starting material, a linear peptide of the Formula (IX) can be obtained by cultivating a microorganism belonging to Deuteromycotina under aerobic conditions in an aqueous or a solid medium and isolating a linear peptide of Formula (IX) from the culture.

The microorganism used in the present invention can be any strains including mutants and variants belonging to Deuteromycotina capable of producing a linear peptide of Formula (IX). Especially preferred is strain NR 7379 which was isolated from fallen leaves collected at Kagoshima pref. in Japan, and identified as a strain belonging to Deuteromycotina.

The strain denoted as Deuteromycotina NR 7379 has been deposited with the National Institute of Bioscience and Human-Technology, Agency of Industrial Science and Technology, Japan on Jun. 16, 1998 under the Budapest Treaty as follows: Deuteromycotina NR 7379 (FERM BP-6391).

The cultivation in accordance with the process provided by the present invention can be carried out in a culture medium which contains customary nutrients usable by the microorganism being cultivated. As carbon sources there can be mentioned, for example, glucose, sucrose, starch, glycerol, molasses, dextrin and mixtures thereof. Nitrogen sources are, for example, soybean meal, cottonseed meal, meat extract, peptone, dried yeast, yeast extract, corn steep liquor, ammonium sulfate, sodium nitrate and mixtures thereof. Moreover, there may be added to the culture medium other organic or inorganic substances for promoting the growth of the microorganism and for increasing the production of a linear peptide of Formula (IX). Examples of such substances are inorganic salts such as, calcium carbonate, sodium chloride, phosphates and the like.

The cultivation is carried out under aerobic conditions preferably in a liquid medium by submerged fermentation, or in a solid medium by static fermentation. A temperature of 20° C. to 30° C., with an optimal temperature of 27° C. is suitable for cultivation. The cultivation is preferably carried out at a pH of 3 to 9. The cultivation time depends on the conditions under which the cultivation is carried out. In general, it is sufficient to carry out the cultivation for 120 to 672 h.

For harvesting the objective linear peptide of Formula (IX) from the cultures, separation methods which are usually employed to isolate metabolites produced by microbes from their cultures can be properly used. For example, a linear peptide of Formula (IX), which is a methanol extractable amphoteric substance, is recovered advantageously by the following procedures.

That is, the cultured broth obtained by liquid fermentation is extracted with an appropriate solvent to recover the proposed product. The solvents which can be used to extract the objective compound from the cultured broth include water-soluble organic solvents or hydrous solutions of water-soluble organic solvents, such as methanol, ethanol and hydrous alcohols, or water-immiscible organic solvent such as n-BuOH.

For removing salts, water soluble substances, etc. from the resulting extract, use is made of, with advantage, solvent partition between water and water-immiscible organic solvents, such as n-butanol, ethyl acetate, etc. For removing coloring substances, fat-soluble substance or the like from the extract, use is made of, with advantage, solvent purification by methanol, ethanol, a mixture of acetonitrile-0.1% aqueous trifluoroacetic acid, etc.

For complete purification of a linear peptide of Formula (IX), column chromatography is used with advantage. Carriers which can be used in such a column chromatography are such as Capcel Pak C18 UG80 (Shiseido Co. LTD, Japan). As an eluent, use is made of a solvent system consisting of a mixture of aqueous trifluoroacetic acid and appropriate water-soluble organic solvents such as methanol, ethanol, acetonitrile, etc. The eluate fraction thus purified, which contains a linear peptide of Formula (IX), can be subjected to concentration or freeze-drying to pulverize a linear peptide of Formula (IX).

A linear peptide of Formula (IX) was isolated as a trifluoroacetic acid salt, but the free linear peptide of Formula (IX) can be prepared by the following procedure. Namely, the linear peptide of Formula (IX) trifluoroacetic acid salt is dissolved in water, to which was added one equivalent of sodium hydroxide, and the mixture is subjected to Sephadex LH-20 column chromatography, followed by elution with a hydrous alcohol such as methanol-water, etc. to thereby obtain a linear peptide of Formula (IX).

The linear peptide of Formula (IX) provided by the present invention does not exhibit any fungicidal activity against various fungi, however, can be a key intermediate to produce potent antifungal agent such as Aerothricins.

The present invention is also concerned with acid addition salts of Aerothricins. The acid addition salt can be obtained as trifluoroacetic acid salt after normal course of isolation. The salt thus obtained may be dissolved in water and passed through an anion exchange column bearing the desired anion. The eluate containing the desired salt may be concentrated to recover the salt as a solid product.

The Aerothricins of Formula (I) may be converted to a corresponding salt by virtue of the presence of the tertiary nitrogen atoms.

The acid addition salt of Aerothricins of Formula (I) can be obtained by treatment of the free base of Aerothricins with at least a stoichiometric amount of an appropriate acid, such as mineral acids, e.g., hydrochloric acid, hydrobromic acid, sulfuric acid, nitric acid, phosphoric acid, and the like, and organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Typically, the free base is dissolved in an inert organic solvent such as ethanol, methanol, and the like, and the acid added in a similar solvent. The temperature is maintained at about 40° C. The resulting salt precipitates spontaneously or may be brought out of solution with a less polar solvent.

The acid addition salts of the Aerothricins of Formula (I) may be converted to the corresponding free base by treatment with at least a stoichiometric amount of a suitable base such as sodium or potassium hydroxide, potassium carbonate, sodium bicarbonate, ammonia, and the like.

Aerothricins provided by the present invention exhibit broad fungicidal activity against various fungi and can be used as agents for treatment and prophylaxis of fungal infectious diseases. The in vitro and in vivo antifungal activity (see Tables 2 and 3) as well as the toxicity to hepatocytes (see Table 4) of the representative Aerothricins of Formula (I) are shown as follows:

1. In vitro antifungal activities

The in vitro antifungal activities of the representative Aerothricins of the present study were evaluated by determining the 50% inhibitory concentration ($IC_{50}$), which was calculated as the lowest concentration of an antifungal to inhibit the growth of fungus to 20% turbidity compared with the drug-free control growth spectrophotometrically.

The $IC_{50}$ values were determined by the broth microdilution procedure based on NCCLS Approved Standard with the following minor modifications (National Committee for Clinical Laboratory Standards. (1997) Reference method for broth dilution antifungal susceptibility testing for yeasts. Approved standard. Document M27-A). Yeast Nitrogen Base (YNB; Difco Lab.) supplemented with 1% glucose and 0.25% $K_2HPO_4$ was used as testing medium for yeast, the same medium solidified with 0.2% low melting point agarose (BRL) was used for filamentous fungi. Inoculum size was 1–3×$10^4$ cells/ml, and incubation was performed for 1–2 days at 35° C.

TABLE 2

In vitro Antifungal activity, $IC_{50}$ (μg/ml)

| | *Candida albicans* CY1002 | *Aspegillus fumigatus* CF1003 | *Fusarium solani* CF1088 |
|---|---|---|---|
| Aerothricin 1 | 0.03 | 0.06 | 0.21 |
| Aerothricin 5 | 0.03 | 0.07 | 0.19 |
| Aerothricin 12 | 0.09 | 0.10 | 2.20 |
| Aerothricin 31 | 0.07 | 0.49 | 0.70 |
| Aerothricin 36 | 0.08 | 0.05 | 1.00 |
| Aerothricin 39 | 0.09 | 0.17 | 0.70 |
| Aerothricin 41 | 0.08 | 0.03 | 2.40 |
| Aerothricin 43 | 0.05 | 0.04 | 0.70 |
| Aerothricin 45 | 0.07 | 0.08 | 2.30 |
| Aerothricin 46 | 0.09 | 0.08 | 1.80 |
| Aerothricin 47 | 0.09 | 0.11 | 1.40 |
| Aerothricin 53 | 0.11 | 0.09 | 2.30 |
| Aerothricin 54 | 0.15 | 0.17 | 0.74 |
| Aerothricin 55 | 0.04 | 0.04 | 0.39 |

TABLE 2-continued

| In vitro Antifungal activity, $IC_{50}$ ($\mu$g/ml) | | | |
|---|---|---|---|
| | *Candida albicans* CY1002 | *Aspegillus fumigatus* CF1003 | *Fusarium solani* CF1088 |
| Aerothricin 57 | 0.14 | 0.05 | 1.30 |
| Aerothricin 75 | 0.15 | 0.10 | 1.40 |
| Aerothricin 77 | 0.13 | 0.10 | 0.67 |
| Aerothricin 95 | 0.14 | 0.10 | 0.74 |

2. In vivo antifungal efficacy

In vivo antifungal efficacy of Aerothricins of the present invention is shown in the following Table 3. Mice of a conventional immunocompetent mouse strain, Crj: CD-1 (ICR) were used for experimental infection models of systemic candidiasis. 4 weeks old Crj: CD-1 (ICR) mice were used for systemic candidiasis by injecting *Candida albicans* $5\times10^6$ conidia/mouse via the tail vein. Treatments were given twice (0, 4 h after infection) on the first day and once daily on following 2 days for systemic candidiasis (b.i.d×1 day followed by q.d.×2 days), intravenously (i.v.). 50% of effective dose ($ED_{50}$) values was calculated from the survival number at each dose on day 14.

TABLE 3

| In vivo antifungal activity against systemic candidiasis in mice, $ED_{50}$ (mg/kg) on day 14 | |
|---|---|
| Aerothricin 5 | 0.3 |
| Aerothricin 16 | 0.3 |
| Aerothricin 18 | 0.6 |
| Aerothricin 36 | 0.6 |
| Aerothricin 41 | 0.3 |
| Aerothricin 42 | 0.6 |
| Aerothricin 45 | 0.3 |
| Aerothricin 46 | 0.4 |
| Aerothricin 50 | <0.3 |
| Aerothricin 55 | <0.3 |
| Aerothricin 65 | 0.6 |

3. In vitro hepatotoxicity test

The mouse hepatocytes were isolated by a collagenase digestion and cultured in microtest plates. The hepatocyte monolayers were exposed to the test Aerothricins in the culture system for 1 day. After the culture period, the hepatocytes were observed under a microscope and evaluated morphologically. The degree of the morphological alteration (degeneration) of the hepatocytes by the test Aerothricins were compared with WF 11243 and LY303366.

TABLE 4

| Cytotoxicity to hepatocyte ($\mu$g/ml) | |
|---|---|
| Aerothricin 14 | >100 |
| Aerothricin 15 | >100 |
| Aerothricin 21 | >100 |
| Aerothricin 34 | >100 |
| Aerothricin 38 | >100 |
| Aerothricin 45 | >100 |
| Aerothricin 47 | >100 |
| Aerothricin 48 | >100 |
| Aerothricin 53 | >100 |
| Aerothricin 65 | >100 |
| Aerothricin 67 | >100 |
| Aerothricin 72 | >100 |
| Aerothricin 81 | >100 |
| WF11243 | 100 |

TABLE 4-continued

| Cytotoxicity to hepatocyte ($\mu$g/ml) | |
|---|---|
| (= Aerothricin 3) | |
| LY303366 | 10 |

5 mg/kg and 30 mg/kg of Aerothricin 1 administration to mice for 4 weeks showed no acute toxicity.

Therefore, the novel Aerothricins of Formula (I) as well as pharmaceutically acceptable salts thereof exhibit potent antifungal activity against various fungal infections, including Aspergillosis, in mice over a wide range of dosages and are useful as antifungal agents. Moreover, the Aerothricins provided by this invention are much less cytotoxic to hepatocytes than the known cyclic peptide derivatives (WF11243 and LY303366).

Aerothricins of the present invention may also be useful for inhibiting or alleviating *Pneumocystis carinii* infections in immune-compromised patients.

The present invention further relates to the pharmaceutical compositions containing the novel Aerothricins of Formula (I) as well as pharmaceutically acceptable salts thereof.

The novel Aerothricins of Formula (I) as well as pharmaceutically acceptable salts thereof are highly active fungicidal agents. They are active against a variety of fungal species including Candida spp., Aspergillus spp., Fusarium spp., Mucor spp. and Absidia Thus, Aerothricins of the present invention are useful for topical and systemic treatment of mycoses in animals as well as humans. For example, they are useful in treating topical and mucosal fungal infections caused by Candida spp., Trichophyton spp., and Microsporum spp. They may also be used in the treatment of systemic fungal infections caused by, for example, Candida spp., Aspergillus spp., or Fusarium spp.

For clinical use, the novel Aerothricins of Formula (I) as well as pharmaceutically acceptable salts thereof can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, nasal, rectal or topical administration.

Pharmaceutical formulations of Aerothricins for oral administration may be granule, tablet, sugar coated tablet, capsule, pill, suspension or emulsion. For parenteral injection, for example, intravenously, intramuscularly or subcutaneously, Aerothricins of Formula (I) may be used in the form of a sterile aqueous solution which may contain other substances, for example, salts or glucose to make the solution isotonic. These compositions also may be presented in unit dosage form in ampoules or in multidose containers, preferable with added preservatives. Alternatively, the active ingredients may be in powder form for reconstituting with a suitable vehicle prior to administration. Aerothricins can also be administered in the form of a suppository or pessary, or they may be applied topically in the form of a lotion, solution, cream, ointment or dusting powder.

The daily dosage level of Aerothricins of Formula (I) is from 0.1 to 50 mg/kg (in divided doses) when administered by either the oral or parenteral route. Thus tablets or capsules of Aerothricins can be expected to contain from 5 mg to 0.5 g of active compound for administration singly or two or more at a time as appropriate. In any event the actual dosage can be determined by the physician and it may be varied upon the age, weight and response of the particular patient.

When Aerothricins are for antifungal use any method of administration may be employed. For treating mycotic infections, oral or intravenous administration is usually employed.

When Aerothricins are to be employed for control of pneumocystis infections it is desirable to directly treat lung and bronchi. For this reason inhalation methods are preferred. For administration by inhalation or nasal, Aerothricins of the present invention are conveniently delivered in the form of an aerosol spray presentation from pressurized packs or nebulisers. The preferred delivery system for inhalation or nasal is a metered dose inhalation aerosol, which may be formulated as a powder, suspension or solution of a compound of Formula (I) in suitable propellants, such as fluorocarbons or hydrocarbons.

Although Aerothricins of the present invention may be employed as tablets, capsules, topical compositions, insufflation powders, suppositories, and the like, the solubility of Aerothricins of the present invention in water and aqueous media render them adaptable for use in injectable formulations and also in liquid compositions suitable for aerosol sprays.

The following Examples illustrate the preferred methods for the preparation of Aerothricins of the present invention, which are not intended to limit the scope of the invention thereto.

In the following Examples, the products were analyzed and purified by HPLC using a reverse phase column selected from those listed below. The mixed solvent consisted of 0.05% trifluoroacetic acid-water: 0.05% trifluoroacetic acid-acetonitrile with the appropriate ratio described in each working Example.

| HPLC columns: | |
|---|---|
| Column A: | CAPCELL PAK C18, UG-120, 4.6 × 250 mm |
| Column B: | CAPCELL PAK C18, UG-120, 10 × 250 mm |
| Column C: | CAPCELL PAK C18, UG-80, 20 × 250 mm |
| Column D: | CAPCELL PAK C18, SG-120, 4.6 × 250 mm |
| Column E: | CAPCELL PAK C18, SG-120, 10 × 250 mm |
| Column F: | TSK GEL ODS-80Ts, 20 × 250 mm |

In the following working Examples, Aerothricins were obtained as trifluoroacetic acid salts unless otherwise indicated.

REFERENCE EXAMPLE 1

Preparation of (R)-3-(9-fluorenylmethoxycarbonylamino)-5-(4'-heptyloxybiphenyl-4-yl)-pentanoic Acid a) Preparation of 4-bromo-4'-heptyloxybiphenyl

To a stirred solution of 4-bromo-4'-hydroxybiphenyl (5.05 g, 20.2 mmol) in DMF (100 ml) were added $K_2CO_3$ (4.20 g, 30.4 mmol) and 1 -bromoheptane (4.14 ml, 26.4 mmol), and then the mixture was heated at 80° C. After being stirred at 80° C. for 20 h, the mixture was cooled to room temperature. The mixture was diluted with $Et_2O$ (250 ml) and then the solution was washed with sat. brine (150 ml×2). The organic layer was dried over anhydrous $Na_2SO_4$ and concentrated in vacuo. The residue was recrystallized from $CH_2Cl_2$-petroleum ether to give 4-bromo-4'-heptyloxybiphenyl (6.21 g, 88%) as a white solid; FAB-MS: m/z 347[$MH^+$].

b) Preparation of 4-formyl-4'-heptyloxybiphenyl

To a cold (0° C.) stirred solution of 4-bromo-4'-heptyloxybiphenyl (6.21 g, 17.9 mmol) in THF (120 ml) was added n-BuLi (1.66 M solution in hexane, 32.3 ml, 53.6 mmol). After the mixture was stirred at 0° C. for 20 min., DMF (4.85 ml, 62.6 mmol) was added at −78° C. The mixture was stirred at −78° C. for additional 20 min., and then quenched with sat. aqueous $NH_4Cl$. The mixture was diluted with EtOAc (220 ml), and then successively washed with sat. aqueous $NH_4Cl$. (125 ml) and sat. brine (100 ml). The organic layer was dried over anhydrous $Na_2SO_4$ and concentrated in vacuo. The residue was purified by column chromatography on silica gel (EtOAc/hexane, 1:20) to give 4-formyl-4'-heptyloxybiphenyl (2.21 g, 42%) as a white amorphous powder.

c) Preparation of 3-(4'-heptyloxybiphenyl-4-yl) Acrylic Acid Ethyl Ester

To a stirred solution of 4-formyl-4'-heptyloxybiphenyl (2.21 g, 7.46 mmol) in benzene (40 ml) was added $Ph_3P{=}CHCOOEt$ (5.19 g, 14.9 mmol), and then the mixture was heated at 60° C. After being stirred at 60° C. for 3 h, the mixture was cooled to room temperature and concentrated in vacuo. The residue was purified by column chromatography on silica gel ($CH_2Cl_2$/hexane, 1:2) to give 3-(4'-heptyloxybiphenyl-4-yl)acrylic acid ethyl ester (2.66 g, 97%) as a white amorphous powder.

FAB-MS: m/z 367[$MH^+$], $^1H$ NMR: δ0.90 (t, J=6.8 Hz, 3H), 1.25–1.55 (m, 8H), 1.35 (t, J=7.1 Hz, 3H), 1.81 (quint, J=6.6 Hz, 2H), 4.00 (t, J=6.4 Hz, 2H), 4.28 (q, J=7.1 Hz, 2H), 6.46 (d, J=16.0 Hz, 1H), 6.94–7.00 (m, 2H), 7.50–7.60 (m, 6H), 7.72 (d, J=16.0 Hz, 1H).

d) Preparation of 3-(4'-heptyloxybiphenyl-4-yl) propionic Acid Ethyl Ester

To a stirred solution of 3-(4'-heptyloxybiphenyl-4-yl) acrylic acid ethyl ester (2.65 g, 7.23 mmol) in $CH_2Cl_2$ (60 ml) was added palladium on activated carbon (Pd ca.10 wt %, 1.07 g), and then the mixture was set under $H_2$ atmosphere. After being stirred for 2 h, the mixture was filtered through a pad of Celite and washed with $CH_2Cl_2$. Filtrate and washings were combined and concentrated in vacuo to give 3-(4'-heptyloxybiphenyl-4-yl)propionic acid ethyl ester (crude, 2.74 g) which was used for the next step without further purification.

$^1H$ NMR: δ0.90 (t, J=6.6 Hz, 3H), 1.25 (t, J=7.3 Hz, 3H), 1.29–1.56 (m, 8H), 1.75–1.86 (m, 2H), 2.65 (t, J=7.8 Hz, 2H), 2.98 (t, J=7.8 Hz, 2H), 3.99 (t, J=6.6 Hz, 2H), 4.14 (q, J=7.3 Hz, 2H), 6.93–6.98 (m, 2H), 7.25 (d, J=8.6 Hz, 2H), 7.43–7.52 (m, 4H).

e) Preparation of 3-(4'-heptyloxybiphenyl-4-yl) propan-1-ol

To a cold (0° C.) stirred suspension of LiAlH4 (0.47 g, 12.4 mmol) in THF (20 ml) was added a solution of 3-(4'-heptyloxybiphenyl-4-yl)propionic acid ethyl ester (crude, 2.74 g) in THF (30 ml). After being stirred for 30 min. at room temperature, the mixture was quenched with $H_2O$ at 0° C. The mixture was filtered through a pad of Celite and washed with $CH_2Cl_2$. The filtrate and washings were combined and concentrated in vacuo. The residue was purified by column chromatography on silica gel (EtOAc/hexane, 2:3) to give 3-(4'-heptyloxy-biphenyl-4-yl)propan-1-ol (2.27 g, 96% for 2 steps) as a white amorphous powder.

EI-MS: m/z 326[$M^+$], $^1H$ NMR: δ0.90 (t, J=6.8 Hz, 3H), 1.21–1.55 (m, 8H), 1.81 (quint, J=6.6 Hz, 2H), 1.86–2.00 (m, 2H), 2.75 (t, J=7.3

Hz, 2H), 3.71 (t, J=6.6 Hz, 2H), 3.99 (t, J=6.6 Hz, 2H), 6.92–7.00 (m, 2H), 7.25 (d, J=7.9 Hz, 2H), 7.44–7.55 (m, 4H).

f) Preparation of 3-(4'-heptyloxybiphenyl-4-yl) propionaldehyde

To a cold (0° C.) stirred solution of 3-(4'-heptyloxybiphenyl-4-yl)propan-1-ol (2.26 g, 6.92 mmol) in $CH_2Cl_2$ (60 ml) were added molecular sieves 4A powder (5.17 g) and PCC (5.25 g, 24.4 mmol). After being stirred for 2 h at room temperature, $Et_2O$ (20 ml) was added to the mixture. The reaction mixture was transferred to a short silica gel column and eluted with $CH_2Cl_2$. The eluate was concentrated in vacuo to give 3-(4'-heptyloxybiphenyl-4-yl) propionaldehyde (crude, 2.45 g) which was used for the next step without further purification.

g) Preparation of 3-(4'-heptyloxybiphenyl-4-yl)pent-2-enoic Acid tert-butyl Ester To a stirred solution of 3-(4'-heptyloxybiphenyl-4-yl) propionaldehyde (crude, 2.45 g) in benzene (150 ml) was added $Ph_3P{=}CHCOOt$-Bu (5.21 g, 13.8 mmol), and then the mixture was heated at 60° C. After being stirred for 30 min. at 60° C., the mixture was cooled to room temperature and concentrated in vacuo. The residue was purified by column chromatography on silica gel (EtOAc/hexane, 1:30) to give 3-(4'-heptyloxybiphenyl-4-yl)pent-2-enoic acid tert-butyl ester (1.95 g, 67% for 2 steps) as a white amorphous powder.

EI-MS: m/z 422[$M^+$], $^1H$ NMR: δ0.90 (t, J=6.6 Hz, 3H), 1.21–1.51 (m, 8H), 1.49 (s, 9H), 1.74–1.87 (m, 2H), 2.47–2.58 (m, 2H), 2.79 (t, J=7.3 Hz, 2H), 3.99 (t, J=6.6 Hz, 2H), 5.81 (d.t., J=1.5 Hz, 15.5 Hz, 1H), 6.87–7.01 (m, 3H), 7.23 (d, J=7.9 Hz, 2H), 7.44–7.53 (m, 4H).

h) Preparation of (R)-3-[benzyl-((R)-1-phenylethyl) amino]-5-(4'-heptyloxybiphenyl-4-yl)pentanoic Acid tert-butyl Ester To a cold (0° C.) stirred suspension of (R)-N-benzyl-1 -phenylethylamine hydrochloride (3.28 g, 13.2 mmol) in THF (40 ml) was added n-BuLi (1.61 M solution in hexane, 15.0 ml, 24.2 nunol). After the mixture was stirred for 25 min. at 0° C., a solution of 3-(4'-heptyloxybiphenyl-4-yl) pent-2-enoic acid tert-butyl ester (1.94 g, 4.38 mmol) in THF (30 ml) was added at −78° C. After the mixture was stirred for additional 20 min. at −78° C., the reaction mixture was quenched with sat. aqueous $NH_4Cl$. and concentrated in vacuo. The residue was diluted with sat. aqueous $NH_4Cl$. (200 ml), and then extracted with $CH_2Cl_2$ (200 ml×2). The combined extracts were dried over anhydrous $Na_2SO_4$ and concentrated in vacuo. The residue was purified by column chromatography on silica gel (EtOAc/hexane, 1:40) to give (R)-3-[benzyl-((R)-1-phenylethyl)amino]-5-(4'-heptyloxybiphenyl-4-yl)pentanoic acid tert-butyl ester (2.83 g, quant.) as a colorless oil.

EI-MS: m/z 633[$M^+$], $^1H$ NMR: δ0.91 (t, J=6.6 Hz, 3H), 1.24–1.55 (m, 13H), 1.38 (s, 9H), 1.57–2.04 (m, 6H), 2.52–2.69 (m, 1H), 2.97–3.10 (m, 1H), 3.37–3.49 (m, 1H), 3.55 (ABq, J=15.0 Hz, 1H), 3.85 (ABq, J=15.0 Hz, 1H), 3.88 (q, J=6.9 Hz, 1H), 4.00 (t, J=6.6 Hz, 1H), 6.96 (d, J=8.6 Hz, 2H), 7.16 (d, J=8.2 Hz, 2H), 7.21–7.53 (m, 16H).

i) Preparation of (R)-3-amino-5-(4'-heptyloxybiphenyl-4-yl)pentanoic Acid tert-butyl Ester To a stirred solution of (R)-3-[benzyl-((R)-1-phenylethyl) amino]-5-(4'-heptyloxy-biphenyl-4-yl)pentanoic acid tert-butyl ester (2.82 g, 4.45 mmol) in EtOAc (50 ml) were added AcOH (2.5 ml) and $Pd(OH)_2$ on carbon ($Pd(OH)_2$ ca. 20 wt %, 1.07 g), and then the mixture was set under $H_2$ atmosphere. After being stirred for 15 h, the mixture was filtered through a pad of Celite and washed with MeOH. The filtrate and washings were combined, and concentrated in vacuo to give (R)-3-amino-5-(4'-heptyloxybiphenyl-4-yl)pentanoic acid tert-butyl ester (crude, 3.14 g) which was used for the next step without further purification.

j) Preparation of (R)-3-(9-fluorenylmethoxycarbonylamino)-5-(4'-heptyloxybiphenyl-4-yl)pentanoic Acid tert-butyl Ester To a stirred suspension of (R)-3-amino-5-(4'-heptyloxybiphenyl-4-yl)pentanoic acid tert-butyl ester (crude, 3.14 g) in 50% aqueous 1,4-dioxane (40 ml) were added $Na_2CO_3$ (1.19 g, 11.2 mmol) and FmocCl (1.28 g, 4.95 mmol). After being stirred for 1 h, the mixture was diluted with sat. brine (100 ml) and extracted with $CH_2Cl_2$ (100 ml×3). The combined extracts were dried over anhydrous $Na_2SO_4$ and concentrated in vacuo to give (R)-3-(9-fluorenylmethoxycarbonylamino)-5-(4'-heptyloxybiphenyl-4-yl)pentanoic acid tert-butyl ester (crude, 3.34 g) which was used for the next step without further purification.

FAB-MS: m/z 668[$M^+$+Li], $^1H$ NMR: δ0.81 (t, J=6.6 Hz, 3H), 1.15–1.44 (m, 8H), 1.35 (s, 9H), 1.62–1.93 (m, 4H), 2.29–2.68 (m, 4H), 3.84–4.02 (m, 1H), 3.88 (t, J=6.6 Hz, 2H), 4.13 (t, J=6.8 Hz, 1H), 4.25–4.41 (m, 2H), 5.27 (d, J=9.2 Hz, 1H), 6.85 (d, J=8.6 Hz, 2H), 7.06–7.42 (m, 10H), 7.51 (d, J=7.3 Hz, 2H), 7.66 (d, J=7.6 Hz, 2H).

k) Preparation of (R)-3-(9-fluorenylmethyloxycarbonylamino)-5-(4'-heptyloxybiphenyl-4-yl)pentanoic Acid To a stirred solution of (R)-3-(9-fluorenylmethoxycarbonyl-amino)-5-(4'-heptyloxybiphenyl-4-yl)pentanoic acid tert-butyl ester (crude, 3.34 g) in $CH_2Cl_2$ (20 ml) was added TFA (20 ml) dropwise. After being stirred for 1 h at room temperature, the mixture was concentrated in vacuo. The residue was purified by column chromatography on silica gel ($MeOH/CH_2Cl_2$, 1:20) to give (R)-3-(9-fluorenylmethoxycarbonylamino)-5-(4'-heptyloxybiphenyl-4-yl)pentanoic acid (2.07 g, 77% in 3 steps) as a white amorphous powder.

FAB-MS: m/z 606[$MH^+$], $^1H$ NMR: δ0.88 (t, J=6.6 Hz, 3H), 1.21–1.51 (m, 8H), 1.64–2.04 (m, 2H), 1.78 (q, J=6.6 Hz, 2H), 2.27–2.78 (m, 4H), 3.91–4.07 (m, 1H), 3.96 (t, J=6.6 Hz, 2H), 4.20 (t, J=6.6 Hz, 1H), 4.34–4.56 (m, 2H), 5.09–5.28 (m, 1H), 6.92 (d, J=8.9 Hz, 2H), 7.10–7.49 (m, 10H), 7.57 (d, J=7.3 Hz, 2H), 7.73 (d, J=7.3 Hz, 2H).

The starting compounds of Formula (IV) [wherein Y is a single bond or $-CH_2-$] used in the process B were prepared according to the method similar to that described above.

REFERENCE EXAMPLE 2

Preparation of (S)-3-(9H-fluorenylmethoxycarbonylamino)-N-undecylsuccinamic Acid a) To a solution of (S)-2-(9H-fluoren-9-ylmethoxycarbonyl-amino)succinic acid (150 mg, 0.36 mmol), BOP reagent (162 mg, 0.36 mmol) and HOBT hydrate (56 mg, 0.36 mmol) in N,N-dimethylformamide (0.2 ml) was added N,N-diisopropylethylamine (64 μl, 0.36 mmol). After being stirred for 30 min at room temperature, 1-aminoundecane (79 μl, 0.37 mmol) was added. The mixture was stirred at room temperature for 3 h. The reaction mixture was diluted with water and extracted with $Et_2O$. The combined extracts were washed with water, dried over anhydrous sodium sulfate, filtered and concentrated. Purification of the residue by silica gel column chromatography (using n-hexane:ethyl acetate =3:1 as an eluent ) gave (S)-3-(9H-fluoren-9-ylmethoxycarbonylamino)-N-undecylsuccinamic acid tert-butyl ester (169 mg, 82% yield) as a colorless amorphous solid.

FAB-MS (m/z): 565[$MH^+$], $^1$H-NMR($CDCl_3$) δ: 0.88 (3H, t, J=7 Hz), 1.24 (16H, m), 1.45 (11H, m), 2.58 (1H, dd, $J_1$=17 Hz, $J_2$=7 Hz), 2.91 (1H, dd, $J_1$=17 Hz, $J_2$=4 Hz), 3.23 (2H, q, J=7 Hz), 4.22 (1H, t, J=7 Hz), 4.42~4.45 (3H, m), 5.94 (1H, broad d, J=8 Hz), 6.43 (1H, broad s), 7.31 (2H, t, J=7 Hz), 7.41 (2H, t, J=7 Hz), 7.58 (2H, d, J=7 Hz), 7.77 (2H, d, J=7 Hz).

b) A solution of (S)-3-(9H-fluoren-9-ylmethoxycarbonylamino)-N-undecylsuccinamic acid tert-butyl ester (113 mg, 0.2 mmol) in TFA (2 ml) was stirred at room temperature for 30 min. After completion of the reaction, TFA was removed by evaporation in vacuo. Purification of the residue by silica gel column chromatography (using dichloromethane:methanol=9:1 as an eluent) gave (S)-3-(9H-fluoren-9-ylmethoxycarbonylamino)-N-undecylsuccinamic acid (101 mg, 99% yield) as a colorless amorphous solid.

FAB-MS (m/z): 507[$MH^+$], $^1$H-NMR($CDCl_3$) δ: 0.87 (3H, t, J=7Hz), 1.23 (16H, m), 1.46 (2H, m), 2.62~2.80 (1H, m), 2.90~3.05 (1H, m), 3.21 (2H, m), 4.20 (1H, t, J=7 Hz), 4.44 (2H, d, J=6 Hz), 4.53 (1H, broad s), 5.98 (1H, m), 6.52 (1H, broad s), 7.30 (2H, t, J=7 Hz), 7.40 (2H, t, J=7 Hz), 7.56 (2H, d, J=7 Hz), 7.76 (2H, d, J=7 Hz The starting compounds of the general Formula (IV) [wherein Y is —CONH— or —CON($CH_3$)—] used in the process B were prepared according to the method described above.

REFERENCE EXAMPLE 3

Preparation of N-Boc-Aerothricin 3 (Compound A)

To a solution of Aerothricin 3 (10.0 g, 6.07 mmol) in MeOH (1500 ml) was added triethylamine (2.54 ml, 18.2 mmol), di-tert-butyl dicarbonate (13.9 ml, 60.7 mmol) successively. After the mixture was stirred at room temperature for 18 h, the solvent was evaporated in vacuo. The residue was dissolved in MeOH (ca. 10 ml) and the solution was added to the diethylether (1500 ml). The resultant precipitate was filtered and washed with diethylether to give 9.9 g of N-Boc-Aerothricin 3 (Compound A) as a pale yellow amorphous solid, which was used for further structural modification in the working examples described below without further purification.

EXAMPLE 4

Preparation of Aerothricins 1, 2 and 3 a) Solid fermentation

A 0.1 ml portion of the frozen culture of Deuteromycotina NR 7379 (FERM BP-6391) in 10% (v/v) glycerol solution was defrosted and inoculated into a 500-ml Erlenmeyer flask containing 100 ml of a medium consisting of 2% glucose, 1% potato starch, 1.5% glycerol, 1% Toast soya (Nissin Seiyu), 0.35% yeast extract (Nippon Seiyaku), 0.25% Polypepton (Nihon Seiyaku), 0.3% NaCl, 0.5% $CaCO_3$, 0.005% $ZnSO_4.7H_2O$, 0.0005% $CuSO_4.5H_2O$, and 0.0005% $MnSO_4.4H_2O$. The pH of the medium was not adjusted. The seed culture was incubated on a rotary shaker at 27° C. for 7 days at 220 rpm. 2 ml of the seed culture was transferred into a 3-liter Erlenmeyer flask containing a solid medium consisting of 200 g pressed barley, 0.12 g yeast extract (Difco), 0.06 g sodium tartarate, 0.06 g $KH_2PO_4$, and 120 ml water. The fermentation was carried out at 27° C. under static condition. The production reached maximum at around 240 h of fermentation and the culture was subjected to the isolation procedure of Aerothricins 1, 2 and 3.

The cultured solid (10 kg) obtained was added methanol (40 L) and the mixture was stirred, followed by removal filtration to obtain methanol extract (39 L). The methanol extract thus obtained was concentrated to dryness under reduced pressure, and the residue (64.8 g) was added ethyl acetate (1 L) and water (1 L). And the mixture was stirred, followed by removal of the ethyl acetate layer.

Furthermore, the aqueous layer was likewise washed with ethyl acetate (1 L) twice. The remaining aqueous layer was extracted with n-butanol (1 L) three times. The extracts thus obtained were combined and concentrated to dryness under reduced pressure, and the residue (28.5 g) was dissolved into a mixture (250 ml) of acetonitrile-0.1% aqueous trifluoroacetic acid (1:1). After removal of the insoluble materials by centrifugation, the solution thus obtained was evaporated to dryness under reduced pressure, and the residue was added methanol (300 ml) and the mixture was stirred, followed by removal filtration to obtain the methanol solution (280 ml). The methanol soluble materials (9.3 g) thus obtained were then subjected to a column chromatography on reversed phase silica gel C18 (1 L). The column was eluted stepwise using a mixture of methanol-0.1% aqueous trifluoroacetic acid (2:8, 4:6, 5:5, 6:4, 7:3, and 8:2). The Aerothricins 1, 2 and 3 eluted in this order with methanol-0.1% aqueous trifluoroacetic acid (7:3) were concentrated to dryness in vacuo to obtain white powdery Aerothricin 3 trifluoroacetic acid salt (731 mg) and Aerothricin 1 trifluoroacetic acid salt (747 mg), respectively. The fractions containing Aerothricin 2 was concentrated under reduced pressure and further purified by HPLC under the following conditions: column: Capcell Pak C18 (i.d. 30×250 mm, Shiseido Co., LTD.); mobile phase: acetonitrile-0.1% aqueous trifluoroacetic acid (45:55); flow rate: 40 ml/min.; detection: UV 220 nm. The appropriate eluates obtained under the above conditions were concentrated to dryness in vacuo to obtain white powdery Aerothricin 2 trifluoroacetic acid salt (42 mg).

b) Flask fermentation

A 2 ml portion of the frozen culture of Deuteromycotina NR 7379 (FERM BP-6391) in 10% (v/v) glycerol solution was defrosted and inoculated into a 500-ml Erlenmeyer flask containing 100 ml of a medium consisting of 1% glucose, 1% oat flour, 4% tomato paste, 0.5% corn steep liquor (Ando kasei), 0.001% $FeSO_4.7H_2O$, 0.001% $MnSO_4.4H_2O$, 0.0001% $CaCl_2$, 0.0002% $ZnSO_4.7H_2O$, 0.00002% $(NH_4)6MoO_2.4H_2O$, and 0.00006% $H_3BO_3$. The pH of the medium was adjusted to 6.8 before sterilization. The seed culture was incubated on a rotary shaker at 27° C. for 3 days at 220 rpm. 2 ml of the first seed culture was transferred into 500-ml Erlenmeyer flasks containing 100 ml of the same medium and incubated on a rotary shaker under the same conditions for 3 days. 2 ml of the second seed culture was inoculated into 500-ml Erlenmeyer flasks containing 100 ml of the medium consisting of 8.5% glycerol, 1% pectin from citrus, 0.4% peanuts powder, 0.4% casein from milk vitamin-free, 0.4% tomato paste, 0.4% corn steep liquor (Ando kasei), 0.2% glycine, and 0.2% $KH_2PO_4$. The pH of the medium was adjusted to 7.0 before sterilization. The fermentation was conducted at 27° C. with agitation of 220 rpm. After 10 days cultivation, the production reached maximum and the whole culture was subjected to the isolation procedure of Aerothricins 1, 2 and 3.

c) Jar fermentation

A 2 ml portion of the frozen culture of Deuteromycotina NR 7379 (FERM BP-6391) in 10% (v/v) glycerol solution was defrosted and inoculated into a 500-ml Erlenmeyer flask containing 100 ml of the same seed medium as described above. The flask was shaken at 220 rpm for 3 days at 27° C. 2 ml of the first seed culture was transferred into 500-ml Erlenmeyer flasks containing 100 ml of the same seed medium and incubated on a rotary shaker under the same conditions for 3 days. Six hundred ml of the second seed culture was inoculated into 50-liter jar fermentor containing 30 liters of the same production medium as described above and 0.4% disfoam (Nissan Disfoam CA-123). The fermentation was carried out at 27° C., with aeration of 30 liters/min. and agitation of 400 rpm. The production reached maximum at around 168 h of fermentation and the whole culture was subjected to the isolation procedure of Aerothricins 1, 2 and 3.

Aerothricin 1

1) Appearance:

white solid

2) Molecular weight (FAB-MS method):

m/z 1547 $(M+H)^+$

3) Molecular formula:

$C_{72}H_{118}N_{14}O_{23}$

4) High resolution mass spectroscopy (for $M+H)^+$:

Found: 1547.8568

Calculated for $C_{72}H_{119}N_{14}O_{23}$: 1547.8572

5) UV spectrum (FIG. 1): in methanol:

λ(ε)max (in MeOH): 225±5 (10600 sh), 270±5 (2000), 278±5 (2100)

λ(ε)max (in N/10 NaOH-MeOH): 240±5 (7700), 268±5 (1800), 298±5 (1800)

Figure 2:
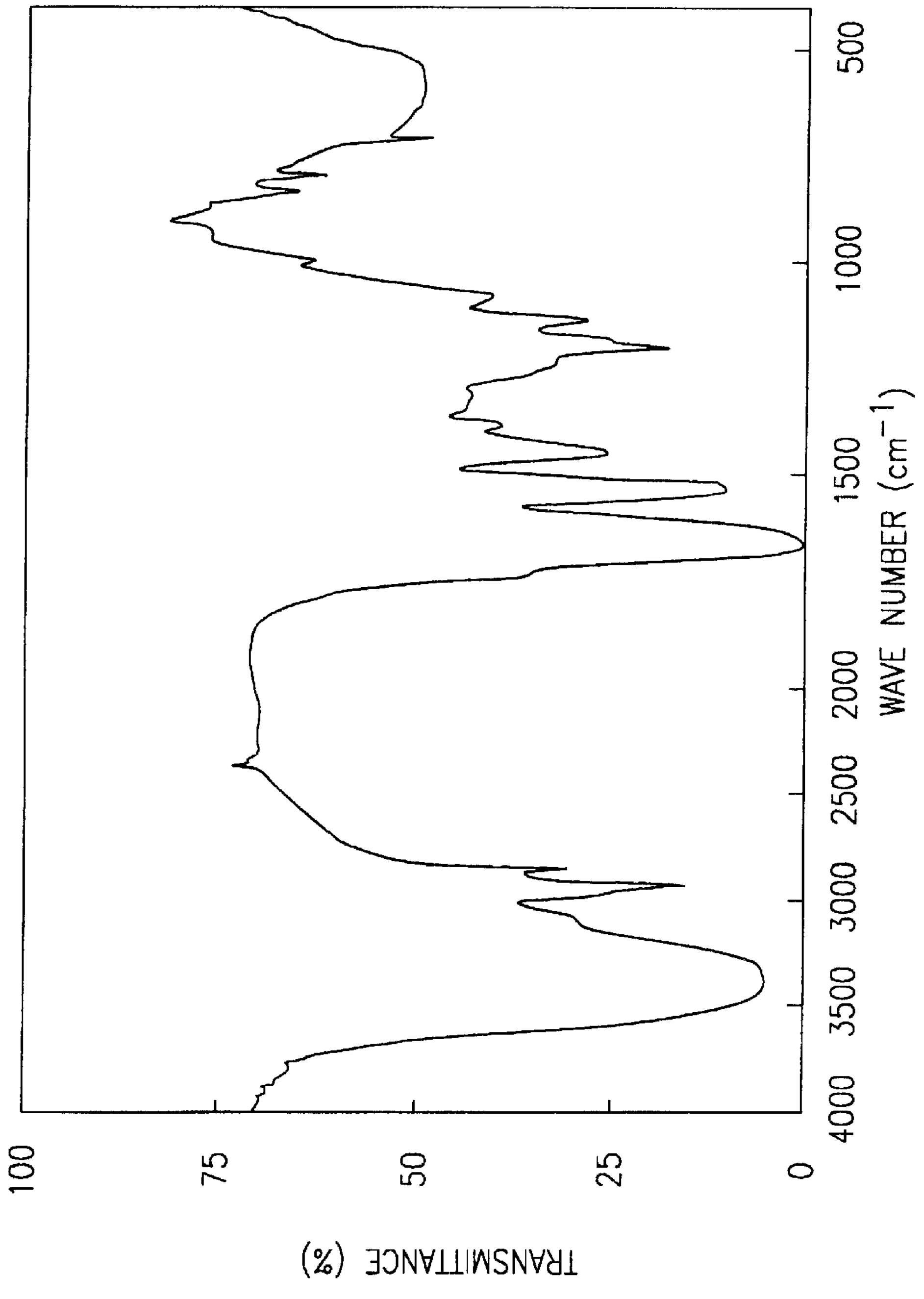
FIG. 2 is the IR spectrum (KBr) for Aerothricin 1.

6) IR spectrum (KBr) (FIG. 2):

Main absorption wave numbers ($cm^{-1}$) are as follows: 3379, 2927, 2855, 1740, 1660, 1535, 1453, 1203, 1139, 837

Figure 3:
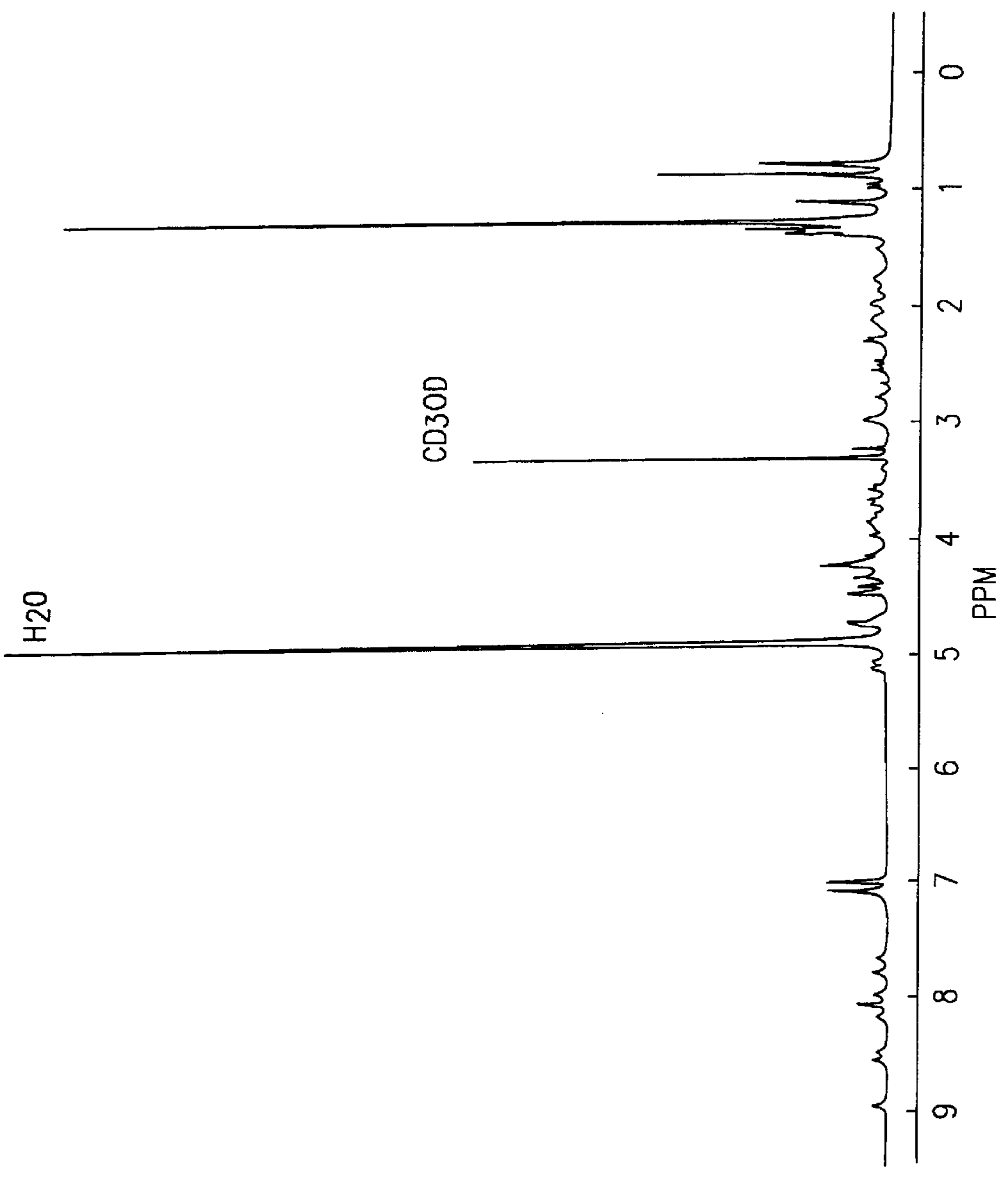
FIG. 3 is the $^1$H-NMR spectrum for Aerothricin 1.

7) $^1$H-NMR spectrum (FIG. 3):

400 MHz, in $CD_3OD$

Figure 4:
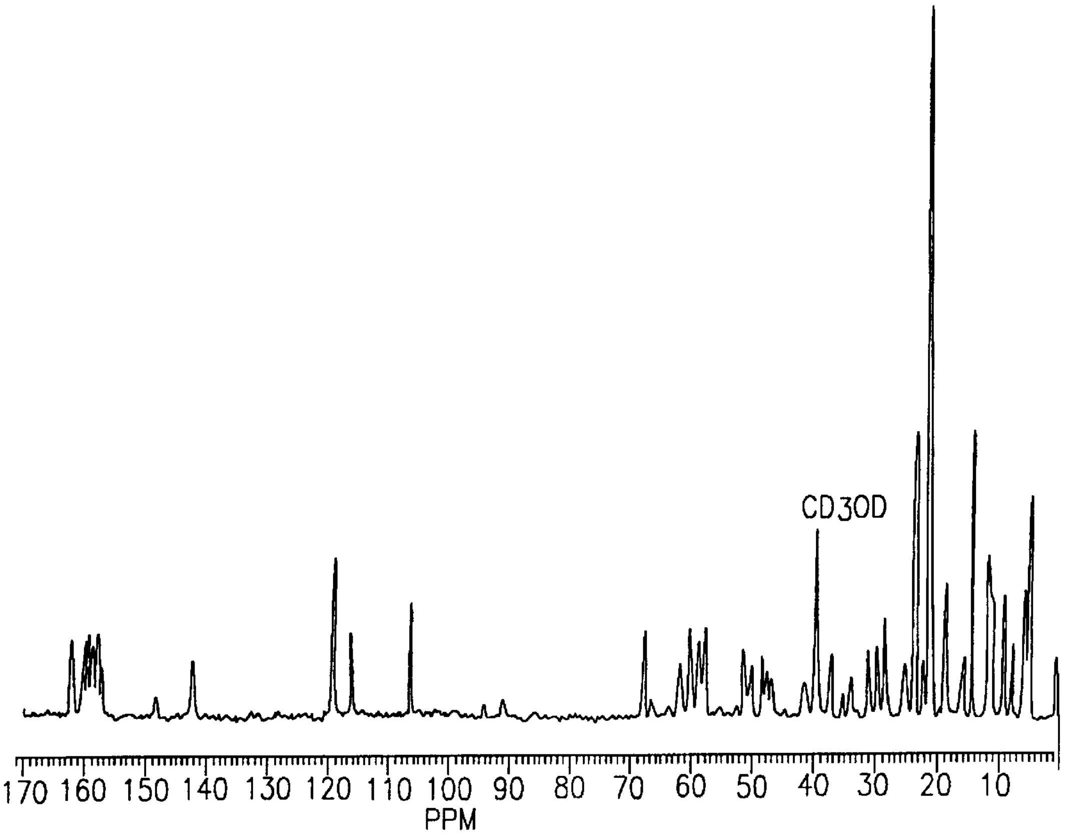
FIG. 4 is the $^{13}$C-NMR spectrum for Aerothricin 1.

8) $^{13}$C-NMR spectrum (FIG. 4):

100 MHz, in $CD_3OD$

9) Solubility:

Soluble: water, methanol, dimethylsulfoxide

10) Color reaction:

Positive: ninhydrin, anisaldehyde-sulfuric acid, iodine vapor, vanillin-sulfuric acid, Rydon-Smith reagent, molybdophosphoric acid Negative: Sakaguchi reagent, Bromocresol green, 2,4-dinitrophenylhydrazine-sulfuric acid 11) Thin-layer chromatography (TLC):

| Carrier | Solvent | Rf |
|---|---|---|
| silica gel F254*1 | n-BuOH: acetone:AcOH:$H_2O$ (4:5:1:1) | 0.74 |
| | MeOH: $H_2O$ (95:5) | 0.12 |

*1E. Merck AG., Germany

12) High Performance Liquid Chromatography:

Carrier: Capcell Pak C18 gel S120A, 4.6×250mm (manufactured by Shiseido, Co., LTD.)

Mobile phase: Acetonitrile: 0.05% aqueous trifluoroacetic acid =1:1

Flow rate: 1ml/min.

Rt=12.1±0.5

13) Amino acid analysis:

Aerothricin 1 was heated at 120° C. in 6N HCl for 24 h, followed by subjecting to amino acid analysis to detect threonine, 3 units of allo-threonine, glycine, alanine, valine, tyrosine, ornithine, 3-hydroxyproline, 4-hydroxyproline, 3-hydroxyglutamine.

Aerothricin 2

1) Appearance:

white solid

2) Molecular weight (FAB-MS method):

m/z 1549 $(M+H)^+$

3) Molecular formula:

$C_{71}H_{116}N_{14}O_{24}$

4) High resolution mass spectroscopy (for $M+H)^+$:

Found: 1549.8384

Calculated for $C_{71}H_{117}N_{14}O_{24}$: 1549.8365

Figure 5:
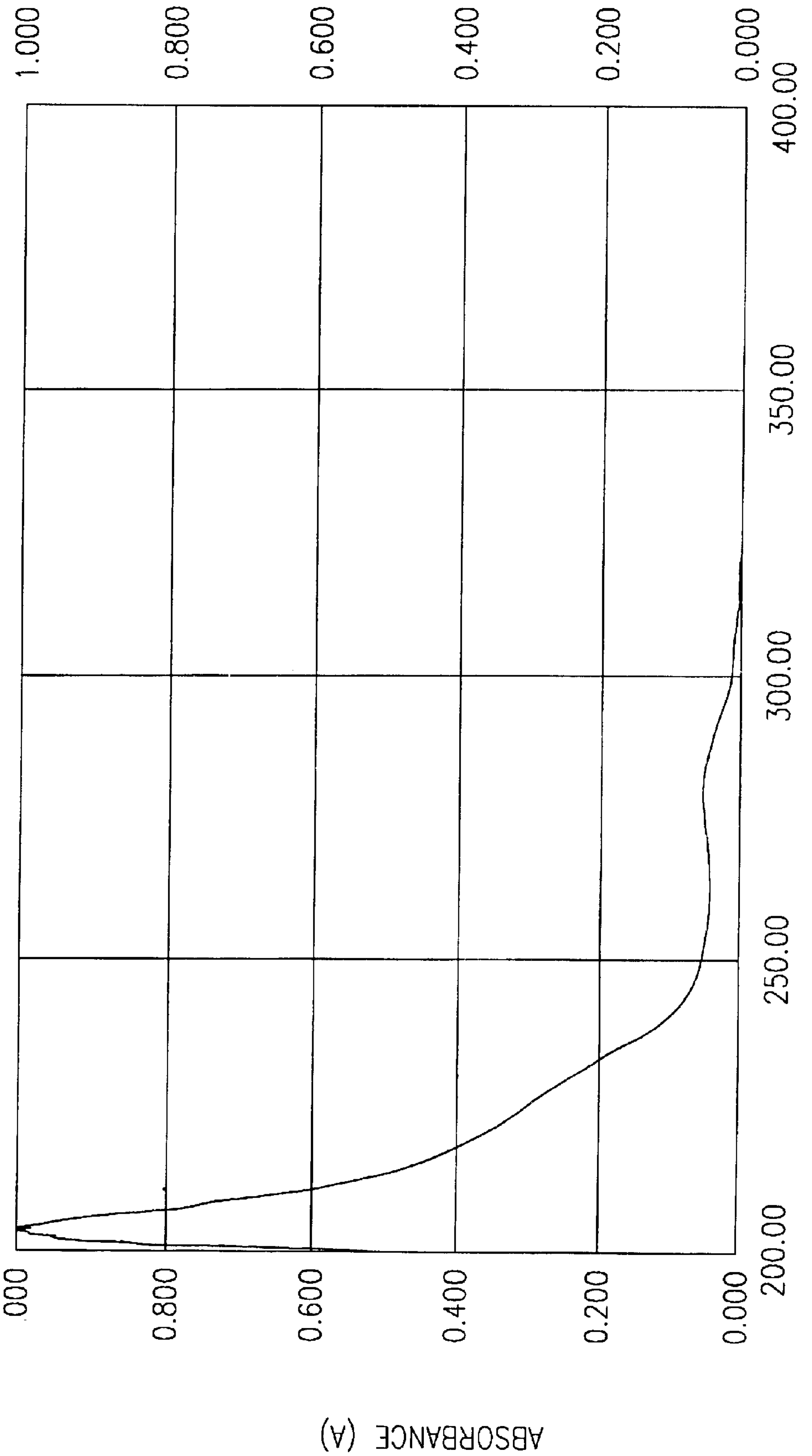
FIG. 5 is the UV spectrum, in methanol, for Aerothricin 2.

5) UV spectrum (FIG. 5): in methanol:

λ(ε)max (in MeOH): 225±5 (10200 sh), 275±5 (1900), 278±5 (2000)

λ(ε)max (in N/10 NaOH-MeOH): 240±15 (7700), 293±5 (2000)

Figure 6:
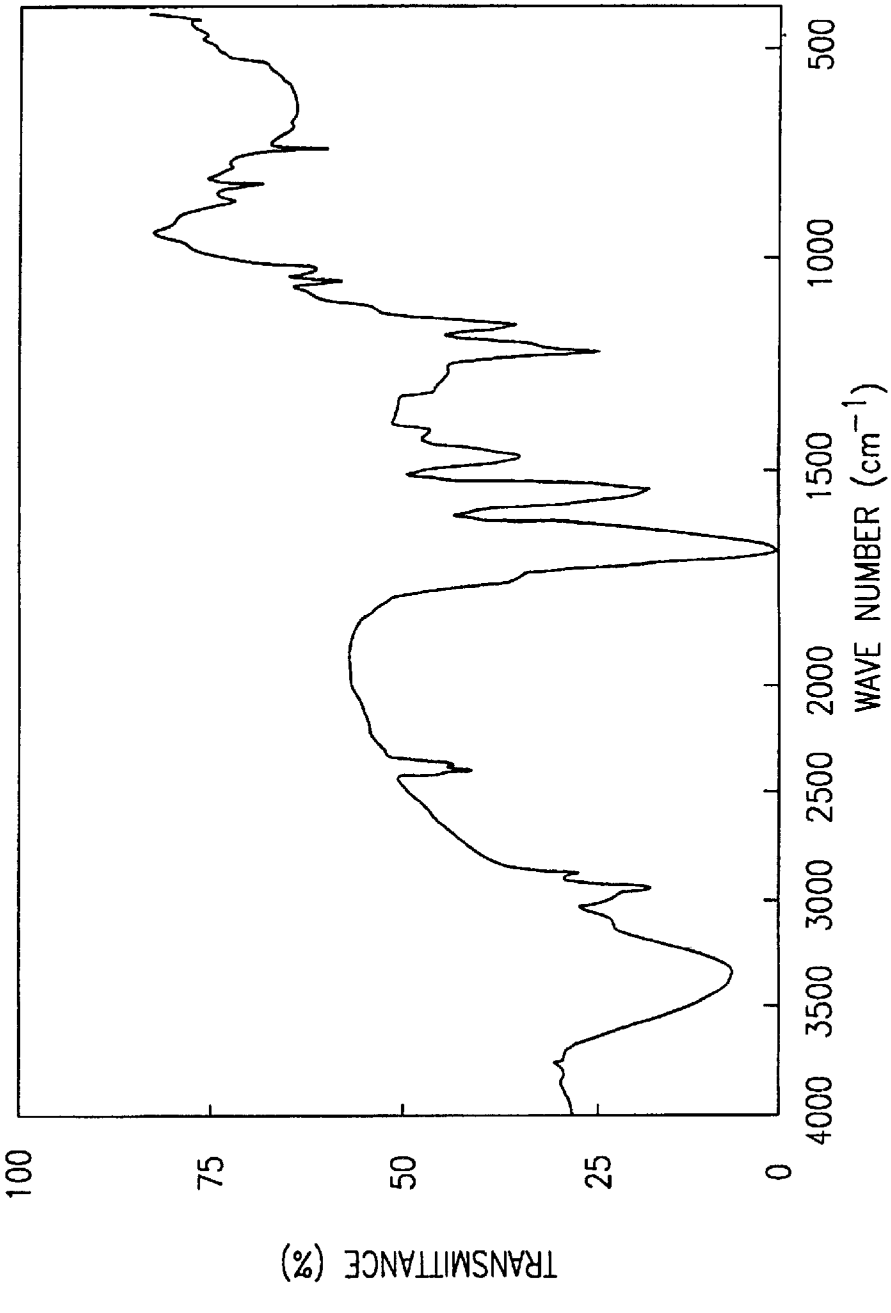
FIG. 6 is the IR spectrum (KBr) for Aerothricin 2.

6) IR spectrum (KBr) (FIG. 6):

Main absorption wave numbers ($cm^{-1}$) are as follows: 3323, 2928, 2856, 1740, 1670, 1531, 1450, 1203, 1137, 837

Figure 7:
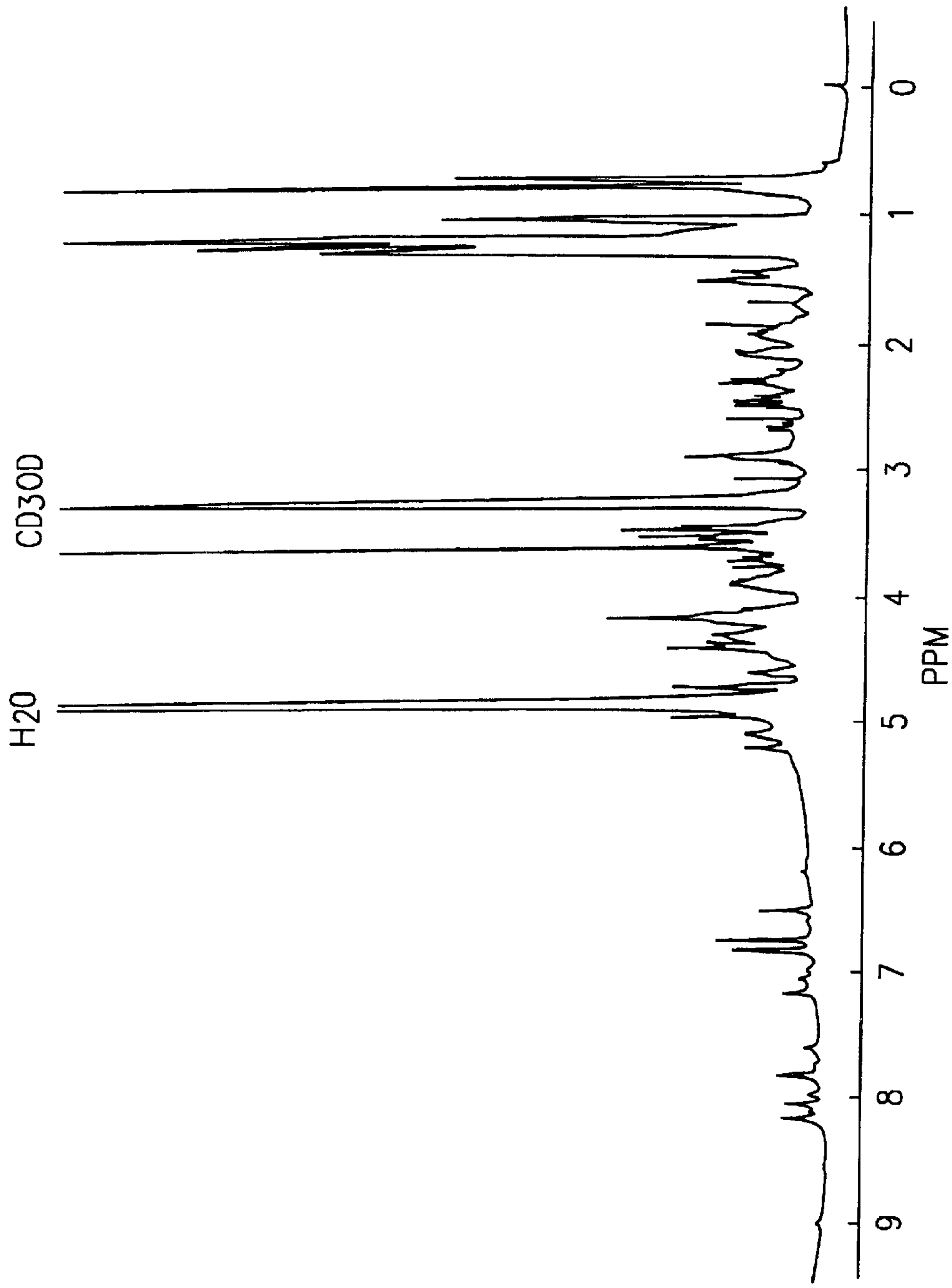
FIG. 7 is the $^1$H-NMR spectrum for Aerothricin 2.
Figure 8:
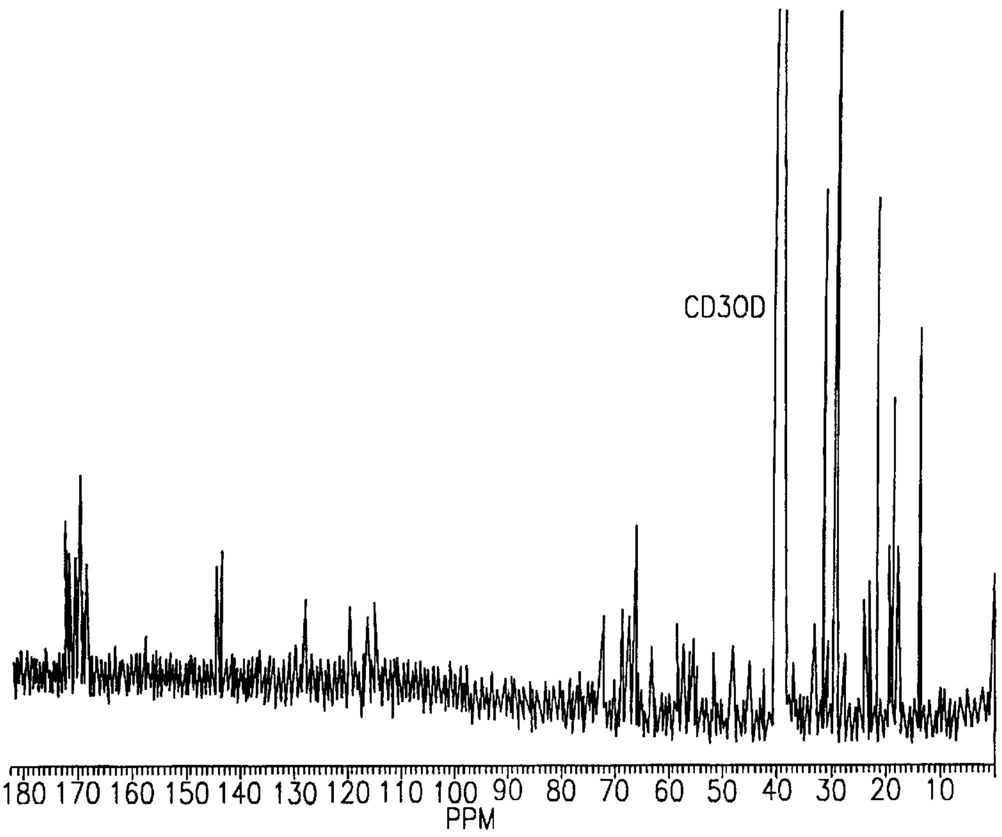
FIG. 8 is the $^{13}$C-NMR spectrum for Aerothricin 2.

7) $^1$H-NMR spectrum (FIG. 7):

400 MHz, in $CD_3OD$ 8) 13C-NMR spectrum (FIG. 8):

100 MHz, in $CD_3OD$

9) Solubility:

Soluble: water, methanol, dimethylsulfoxide

10) Color reaction:

Positive: ninhydrin, anisaldehyde-sulfuric acid, Iodine vapor, vanillin-sulfuric acid, Rydon-Smith reagent, molybdophosphoric acid Negative: Sakaguchi reagent, bromocresol green, 2,4-dinitrophenylhydrazine-sulfuric acid 11) Thin-layer chromatography (TLC):

| Carrier | Solvent | Rf |
|---|---|---|
| Silica gel F254*1 | n-BuOH: acetone:ACOH:$H_2O$ (4:5:1:1) | 0.29 |
| | MeOH: $H_2O$ (95:5) | 0.15 |

*1E. Merck AG., Germany

12) High Performance Liquid Chromatography:

Carrier: Capcell Pak C18 gel S120A, 4.6×250mm (manufactured by Shiseido, Co., LTD.)

Mobile phase: Acetonitrile : 0.05% aqueous trifluoroacetic acid=1:1

Flow rate: 1 ml/min.

Rt=9.9±0.5

13) Amino acid analysis:

Aerothricin 2 was heated at 120° C. in 6N HCl for 24 h, followed by subjecting to amino acid analysis to detect threonine, 3 units of allo-threonine, glycine, alanine, valine, 3-hydroxytyrosml (DOPA), ornithine, 3-hydroxyproline, 4-hydroxyproline, 3 -hydroxyglutamine.

Aerothricin 3

1) Appearance:

white solid

2) Molecular weight (FAB-MS method):

m/z 1533 $(M+H)^+$

3) Molecular formula:

$C_{71}H_{116}N_{14}O_{23}$

4) UV spectrum: in methanol

λ(ε)max (in MeOH): 225±5 (11000 sh), 275±5 (2000), 280±5 (1900)

λ(ε)max (in N/10 NaOH-MeOH): 243±5 (7800), 295±5 (1800)

5) IR spectrum (KBr):

Main absorption wave numbers ($cm^{-1}$) are as follows: 3334, 2928, 2852, 1742, 1662, 1520, 1449, 1202, 1136, 836

6) Solubility:

Soluble: water, methanol, dimethylsulfoxide

7) Color reaction:

Positive: ninhydrin, anisaldehyde-sulfuric acid, Iodine vapor, vanillin-sulfuric acid, Rydon-Smith reagent, molybdophosphoric acid Negative: Sakaguchi reagent, bromocresol green, 2,4-dinitrophenylhydrazine-sulfuric acid 8) Thin-layer chromatography (TLC):

| Carrier | Solvent | Rf |
|---|---|---|
| silica gel F254*1 | n-BuOH: acetone:AcOH:$H_2O$ (4:5:1:1) | 0.26 |
| | MeOH: $H_2O$ (95:5) | 0.09 |

*1E. Merck AG., Germany

9) High Performance Liquid Chromatography:

Carrier: Capcell Pak C18 gel S120A, 4.6×250mm (manufactured by Shiseido, Co., LTD.)

Mobile phase: Acetonitrile: 0.05% aqueous trifluoroacetic acid=1:1

Flow rate: 1 ml/min.

Rt=9.1±0.5

10) Amino acid analysis:

Aerothricin 3 was heated at 120° C. in 6N HCl for 24 h, followed by subjecting to amino acid analysis to detect threonine, 3 units of allo-threonine, glycine, alanine, valine, tyrosine, ornithine, 3-hydroxyproline, 4-hydroxyproline, 3 -hydroxyglutamine.

EXAMPLE 5

Preparation of compound (IX)

1) Flask fermentation

A 2 ml portion of the frozen culture of Deuteromycotina NR 7379 (FERM BP-6391) in 10% (v/v) glycerol solution was defrosted and inoculated into a 500-ml Erlenmeyer flask containing 100 ml of a medium consisting of 1% glucose, 1% oat flour, 4% tomato paste, 0.5% corn steep liquor (Ando kasei), 0.001% $FeSO_4.7H_2O$, 0.001% $MnSO_4.4H_2O$, 0.0001% $CaCl_2$, 0.0002% $ZnSO_4.7H_2O$, 0.00002% $(NH_4)_6MoO_2.4H_2O$, and 0.00006% $H_3BO_3$. The pH of the medium was adjusted to 6.8 before sterilization. The seed culture was incubated on a rotary shaker at 27° C. for 4 days at 220 rpm. 2 ml of the seed culture was inoculated into 500-ml Erlenmeyer flasks containing 100 ml of the medium consisting of 8.5% glycerol, 1% pectin from citrus, 2% peanuts powder, 0.4% casein from milk vitamin-free, 0.4% tomato paste, 0.4% glycine, and 0.2% $KH_2PO_4$. The pH of the medium was adjusted to 7.0 before sterilization. The fermentation was conducted at 27° C. with agitation of 220 rpm. After 14 days cultivation, the production reached maximum and the whole culture was subjected to the isolation work.

The cultured whole broth (1.9 L) obtained was added n-butanol (2 L) and the mixture was stirred. The extracts thus obtained were concentrated to dryness under reduced pressure. And the residue was added hexane (500 ml) and methanol (500 ml) and the mixture thus obtained was stirred, followed by removal of the hexane layer. After removal of the methanol under reduced pressure, the residue thus obtained was washed with a mixture of hexane and ethyl acetate (1:1; 200 ml, twice), and dried under reduced pressure.

The residue (3.9 g) was added water (20 ml) and the mixture was stirred, followed by centrifugation to obtain the water solution. The solution thus obtained were then subjected to a column chromatography on reversed phase silica gel C18 (200 L). The column was first eluted with 0.1% aqueous trifluoroacetic acid and then eluted stepwise using a mixture of methanol-0.1% aqueous trifluoroacetic acid (1:9, 3:7, 5:5, 6:4, 7:3, and 8:2). The compound (IX) eluted with methanol-0.1% aqueous trifluoroacetic acid (7:3) were combined and the solution was neutralized with 1 N aqueous sodium hydroxide, followed by concentration to dryness in vacuo. The residue thus obtained was added water (10 ml) and n-butanol (10 ml) and the mixture was stirred. The extract thus obtained was concentrated under reduced pressure to obtain compound (IX) (96.9 mg) as white powder. The further purification to obtain compound (IX) for spectroscopy was achieved by HPLC under the following conditions: column: Capcell Pak C18 UG80 (i.d. 20×250 mm, Shiseido Co., LTD.); mobile phase: 0.05% trifluoroacetic acid/acetonitrile-0.05% trifluoroacetic acid/water (38:62); flow rate: 22.86 ml/min.; detection: UV 210 nm. The appropriate eluates obtained under the above conditions were concentrated to dryness in vacuo to obtain white powdery compound (IX) trifluoroacetic acid salt.

c) Jar fermentation

A 2ml portion of the frozen culture of Deuteromycotina NR 7379 (FERM BP-6391) in 10% (v/v) glycerol solution was defrosted and inoculated into a 500-ml Erlenmeyer flask containing 100 ml of the same seed medium as described above. The flask was ishaken at 220 rpm for 4 days at 27° C. Two ml of the first seed culture was transferred into 500-ml Erlenmeyer flasks containing 100 ml of the same seed medium and incubated on a rotary shaker under the same conditions for 3 days. 600 ml of the second seed culture was inoculated into 50-liter jar fermentor containing 30 liters of the same production medium as described above and 0.4% disfoam (Nissan Disfoam CA-123). The fermentation was carried out at 27° C., with aeration of 30 liters/min. and agitation of 400 rpm. The production reached maximum at around 278 h of fermentation and the whole culture was subjected to the isolation procedure of compound (IX).

Compound (IX)

1) Appearance:

white solid

2) Molecular weight (FAB-MS method):

m/z 1317 $(M+H)^+$

3) Molecular formula:

$C_{59}H_{104}N_{12}O_{21}$

4) High resolution mass spectroscopy (for $M+H)^+$:

Found: 1317.7555

Calculated for $C_{59}H_{105}N_2O_{21}$: 1317.7517

5) UV spectrum: in methanol:

λ(ε)max (in MeOH): End absorption

Figure 9:
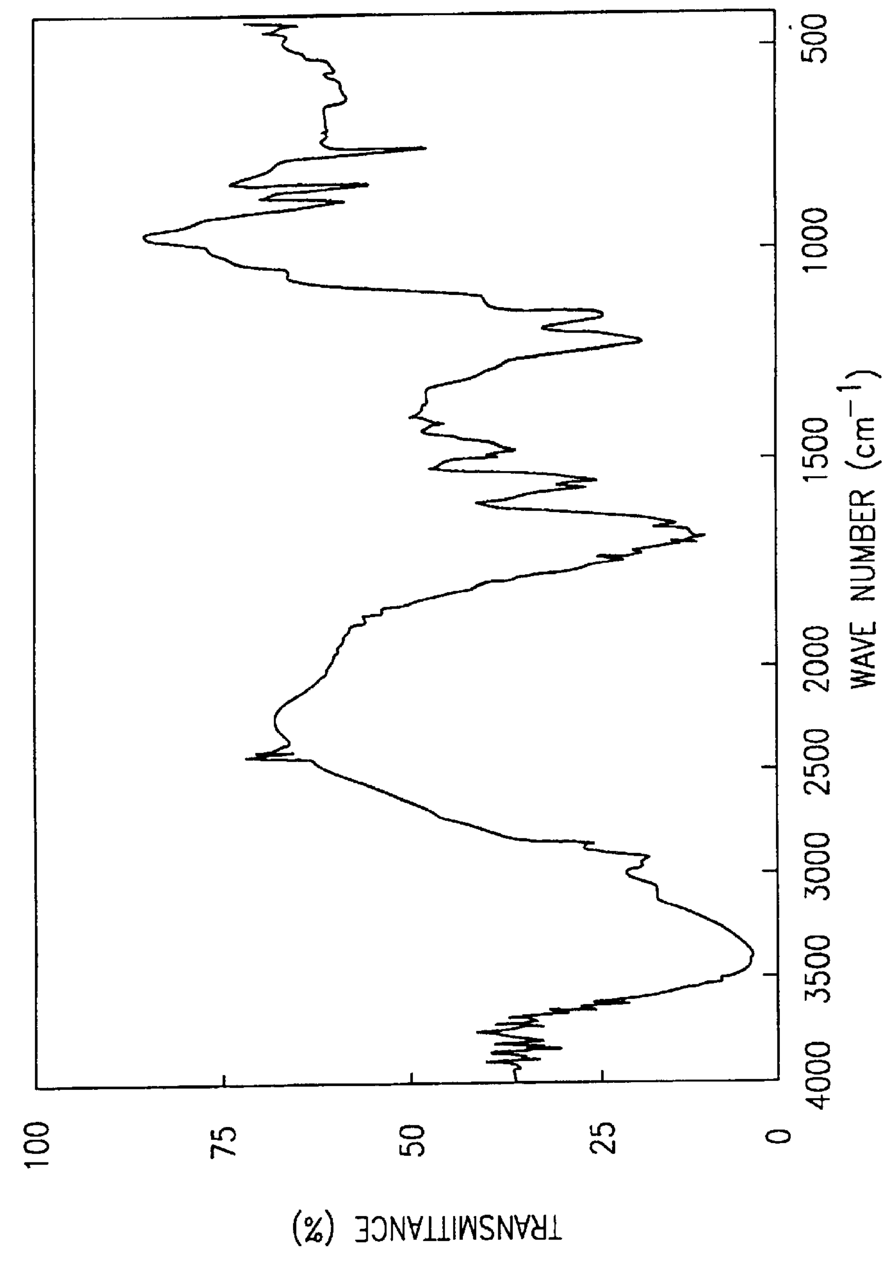
FIG. 9 is the IR spectrum (KBr) for Compound (IX).

6) IR spectrum (KBr) (FIG. 9):

Main absorption wave numbers ($cm^{-1}$) are as follows: 3450, 2928, 1665, 1520, 1450, 1225, 1135

Figure 10:
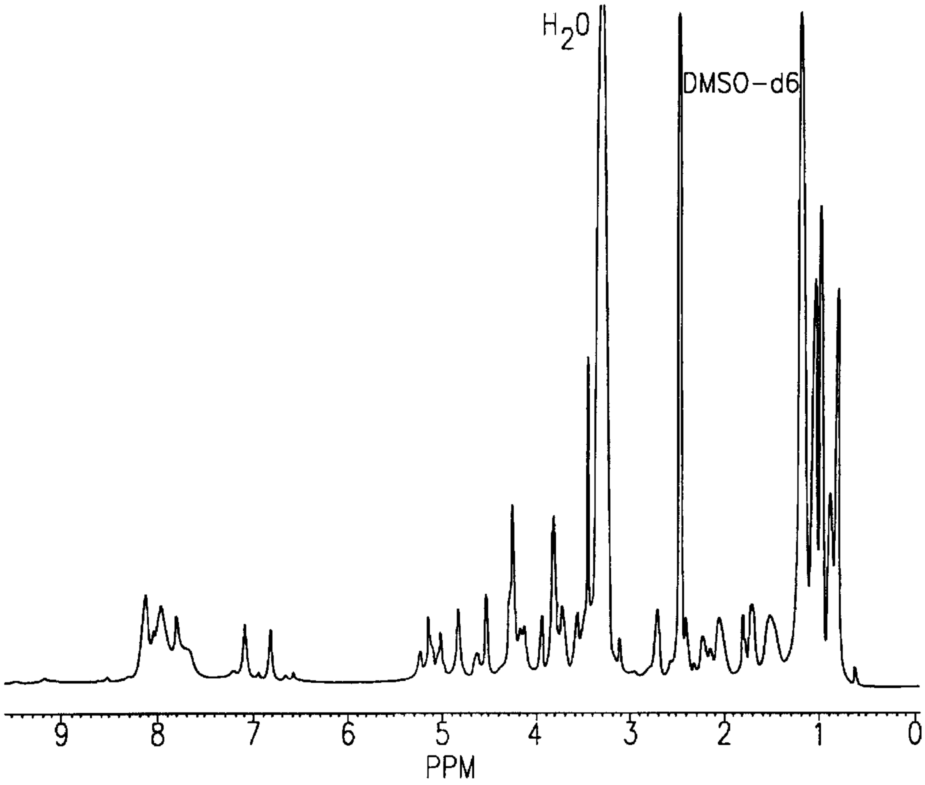
FIG. 10 is the $^1$H-NMR spectrum for Compound (IX).

7) $^1$H-NMR spectrum (FIG. 10):

500 MHz, in DMSO-$d_6$

Figure 11:
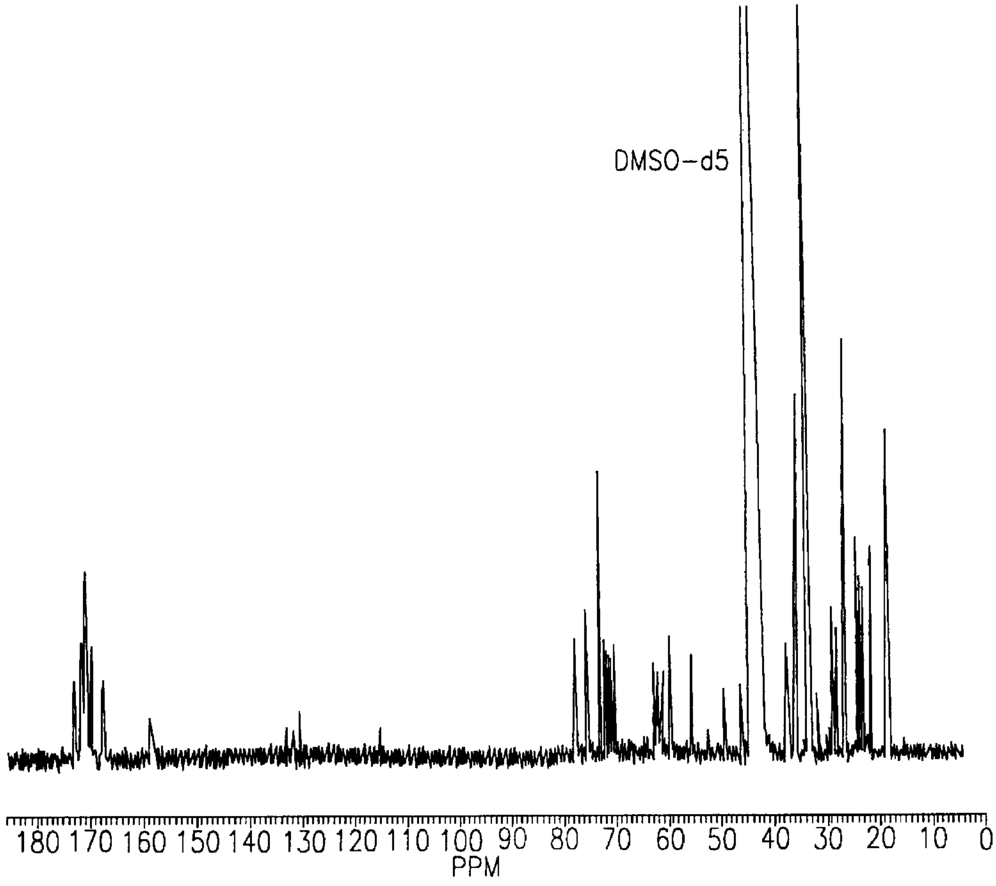
FIG. 11 is the $^{13}$C-NMR spectrum for Compound (IX).

8) $^{13}$C-NMR spectrum (FIG. 11):

125 MHz, in DMSO-$d_6$

9) Solubility:

Soluble: water, methanol, dimethylsulfoxide

10) Color reaction:

Positive: ninhydrin, anisaldehyde-sulfuric acid, iodine vapor, vanillin-sulfuric acid, Rydon-Smith reagent, molybdophosphoric acid Negative: Sakaguchi reagent, Bromocresol green, 2,4-dinitrophenylhydrazine-sulfuric acid 11) High Performance Liquid Chromatography:

Carrier: Capcell Pak C18 UG80A, 4.6×250 mm (manufactured by Shiseido, Co., LTD.)

Mobile phase: 0.05% trifluoroacetic acid/acetonitrile: 0.05% trifluoroacetic acid/water=38:62

Flow rate: 1 ml/min.

Rt=7.7±0.5

EXAMPLE 6

Preparation of N-Boc derivative (N(orn)-Boc-IX) of the ornitine residue of the compound (IX): The compound of Formula (XII: $R^6$=Boc)

To a solution of the compound (IX) obtained in the Example 5 (10.4 mg, 0.0073 mmol) in dioxane-$H_2O$ (0.43 ml-0.5 ml), were added triethylamine (3 μl) and 0.1 M solution of tert-butyl N-succinimidyl carbonate (0.0073111, 0.0073 mmol) in dioxane at room temperature. After being stirred for 1.5 h, the mixture was acidified with acetic acid and was evaporated under reduced pressure. Purification of the residue by HPLC gave N(orn)-Boc-IX as a colorless amorphous (4.8 mg, 45% yield);

HPLC (Rt) 18.0 min. (column: Soken-ODS, 20×250 mm, flow rate: 9 ml/min., eluent: $H_2O$:$CH_3CN$=gradient 1% acetic acid); FAB-MS $[M+Na]^+$1440.

EXAMPLE 7

Preparation of N-Boc derivative (N(va1)-Boc-IX) of the valine residue of the compound (IX): The compound of Formula (X: $R^7$=Boc)

A mixture of the compound (IX) obtained in the Example 5 (15.0 mg, 0.0105 mol), di-tert-butyl dicarbonate (0.073M in methanol solution, 0.20 ml, 0.015 mmol) and triethylamine (7.8 μl) in MeOH (3 ml) was stirred at 0° C. for 24 h. The mixture was washed with n-hexane was evaporated under reduced pressure. Purification of the residue by reverse phase HPLC gave the (N(vao)-Boc-IX) as a colorless amorphous (1.0 mg, 6% yield);

HPLC (Rt) 16.0 min. (column: Soken-ODS, 20×250 mm, flow rate: 9 ml/min., eluent: $H_2O$:$CH_3CN$=gradient 1% acetic acid); FAB-MS $[M+H]^+$1418.

EXAMPLE 8

Preparation of Aerothricin 33

To a stirred solution of (R)-3-(9-fluorenylmethoxycarbonylamino)-7-(4-pentyloxyphenyl) heptanoic acid (25.5 mg, 0.048 mmol) in DMF (0.5 ml) were added BOP reagent (21.3 mg, 0.048 mmol), HOBT hydrate (7.5 mg, 0.049 mmol) and N,N-duisopropylethylamnine (0.0095 ml, 0.055 mmol). After the mixture was stirred at room temperature for 1 h, a solution of Compound B [=the linear peptide of Formula (III) wherein $R^2$ and $R^3$ are hydrogen, $R^5$ is carbamoyl group and $R^7$ is tert-butoxycarbonyl which was prepared from Aerothricin 1 or 3 according to the procedure described in WO 96/303991] (50.7 mg, 0.036 mmol) and N,N-diisopropylethmine (0.0095 ml, 0.055 mmol) in DMF (0.6 ml) was added to the reaction mixture. After the mixture was stirred for 2.5 h at room temperature, piperidine (0.20 ml) was added, and the mixture was stirred for additional 2 h at room temperature. The solvent was evaporated in vacuo. The residue was purified by preparative reverse phase HPLC (column C, flow rate: 9 ml/min.; gradient: eluent: 1% AcOH—$H_2O$:1% AcOH—$CH_3CN$==80:20→2:98). The appropriate fractions were combined, frozen and lyophilized to give 49.5 mg of the linear peptide C, a precursor for cyclization, as a white amorphous solid.

To a stirred solution of the linear peptide C (49.5 mg, 0.029 mmol) obtained above in DMF (27 ml) was added HOBT hydrate (11.3 mg, 0.074 mmol), N,N-diisopropyletylamine (0.018 ml, 0.105 mmol) and a solution of BOP reagent (33.1 mg, 0.075 mmol) in DMF (4 ml). After the mixture was stirred for 3 h at room temperature, the solvent was evaporated in vacuo.

The residue obtained above was dissolved in TFA (6 ml), and stirred at 0° C. for 30 min. TFA was then evaporated in vacuo. The residue was purified by preparative reverse phase HPLC, the detailed condition of which is shown below. The appropriate fractions were combined, frozen and lyophilized to give 19.4 mg of Aerothricin 33 as a white amorphous solid.

HPLC(Rt): 12.4 min. (column C, flow rate: 9 ml/min.; eluent: 0.05% trifluoroacetic acid-water: 0.05% trifluoroacetic acid-acetonitrile =61:39); FAB-MS (m/z): 1568 $[MH^+]$.

The following Aerothricins 34–38, 40–53, 64–73 and 89–95, 97–99 and 123 were prepared according to the method similar to that descried in this Example 8 using the corresponding building block represented as Formula (IV).

| Compound name | FAB-MS m/z: [MH+] | HPLC retention time (min.) | Analytical condition (column) (flow rate; ratio of eluent*) |
|---|---|---|---|
| Aerothricin 34 | 1568 | 14.1 | (C)(9 ml/min.; 60/40) |
| Aerothricin 35 | 1568 | 13.2 | (C)(9 ml/min.; 57/43) |
| Aerothricin 36 | 1610 | 21.9 | (C)(9 ml/min.; 55/45) |
| Aerothricin 37 | 1638 | 44.1 | (C)(9 ml/min.; 54/46) |
| Aerothricin 38 | 1610 | 28.1 | (C)(9 ml/min.; 58/42) |
| Aerothricin 40 | 1602 | 16.8 | (F)(10 ml/min.; 57/43) |
| Aerothricin 41 | 1616 | 20.6 | (C)(9 ml/min.; 60/40) |
| Aerothricin 42 | 1630 | 16.8 | (F)(10 ml/min.; 62/38) |
| Aerothricin 43 | 1644 | 29.2 | (C)(9 ml/min.; 57/43) |
| Aerothricin 44 | 1658 | 35.5 | (F)(10 ml/min.; 50/50) |
| Aerothricin 45 | 1630 | 24.7 | (C)(9 ml/min.; 59/41) |
| Aerothricin 46 | 1664 | 18.7 | (C)(9 ml/min.; 59/41) |
| Aerothricin 47 | 1594 | 22.9 | (C)(9 ml/min.; 54/46) |
| Aerothricin 48 | 1576 | 24.4 | (F)(10 ml/min.; 58/42) |
| Aerothricin 49 | 1590 | 24.2 | (C)(9 ml/min.; 65/35) |
| Aerothricin 50 | 1604 | 48.9 | (F)(10 ml/min.; 55/45) |
| Aerothricin 51 | 1618 | 40.4 | (F)(9 ml/min.; 60/40) |
| Aerothricin 52 | 1632 | 32.5 | (F)(10 ml/min.; 50/50) |
| Aerothricin 53 | 1646 | 27.0 | (C)(9 ml/min.; 54/46) |
| Aerothricin 64 | 1547 | 15.5 | (B)(4 ml/min.; 65/35) |
| Aerothricin 65 | 1575 | 15.5 | (C)(9 ml/min.; 55/45) |
| Aerothricin 66 | 1603 | 16.6 | (C)(9 ml/min.; 52/48) |
| Aerothricin 67 | 1587 | 19.9 | (C)(9 ml/min.; 59/41) |
| Aerothricin 68 | 1587 | 19.6 | (C)(9 ml/min.; 59/41) |
| Aerothricin 69 | 1589 | 21.8 | (C)(9 ml/min.; 58/42) |
| Aerothricin 70 | 1617 | 21.6 | (C)(9 ml/min.; 53/47) |
| Aerothricin 71 | 1746 | 30.0 | (C)(9 ml/min.; 64/36) |
| Aerothricin 72 | 1673 | 22.6 | (C)(9 ml/min.; 57/43) |
| Aerothricin 73 | 1721 | 20.2 | (C)(9 ml/min.; 55/45) |
| Aerothricin 89 | 1630 | 22.1 | (F)(10 ml/min.; 55/45) |
| Aerothricin 90 | 1658 | 24.9 | (F)(10 ml/min.; 50/50) |
| Aerothricin 91 | 1670 | 26.7 | (F)(10 ml/min.; 50/50) |
| Aerothricin 92 | 1642 | 26.0 | (F)(10 ml/min.; 55/45) |
| Aerothricin 93 | 1650 | 21.4 | (F)(10 ml/min.; 57/43) |
| Aerothricin 94 | 1658 | 30.8 | (F)(10 ml/min.; 52/48) |
| Aerothricin 95 | 1574 | 28.3 | (C)(9 ml/min.; 57/43) |
| Aerothricin 97 | 1740 | 44.7 | (F)(10 ml/min.; 57/43) |
| Aerothricin 98 | 1656 | 30.0 | (F)(10 ml/min.; 62/38) |
| Aerothricin 99 | 1644 | 16.9 | (F)(10 ml/min.; 53/47) |
| Aerothricin 123 | 1630 | 20.7 | (F)(10 ml/min.; 56/44) |

*ratio of 0.05% trifluoroacetic acid-water: 0.05% trifluoroacetic acid-acetonitrile

EXAMPLE 9

Preparation of Aerotliricin 16

(a). To a stirred solution of Compound A (described in Reference Example 3) (1 g, 0.61 mmol) in pyridine (2.5 ml) was added tetranitromethane (0.365 ml, 3.05 mmol). After being stirred for 4 h at room temperature, the reaction mixture was concentrated in vacuo. The dark-brown residue was purified by reverse phase HPLC (Lobar RP 18, 10 ml/min., 0.05% trifluoroacetic acid-water: 0.05% trifluoro-acetic acid-acetonitrile=50:50→33:66 0.05% TFA). The appropriate fractions were combined, frozen and lyophilized to give 711 mg of the crude nitro derivative of Compound A as a pale yellow amorphous solid.

(b). A mixture of the crude product obtained above (12 mg, 0.0071 mmol) and TFA 0.5 ml) was stirred at 0° C. for 30 min. TFA was evaporated under a stream of dry nitrogen. The yellow residue was purified by preparative reverse phase HPLC. The appropriate fractions were combined, frozen and lyophilized to give 8 mg of Aerothricin 16.TFA salt as a pale yellow amorphous solid.

HPLC(Rt): 15.5 min. (column B, flow rate: 4 ml/min., eluent: 0.05% trifluoroacetic acid-water: 0.05% trifluoro-acetic acid-acetonitrile =55:45); FAB-MS (m/z): 1578 [$MH^+$].

The following Aerothricins 39, 54, 55 and 77 were prepared according to the method similar to that described in Example 9, using Aerothricins obtained in Example 8 as the starting material.

| Compound name | FAB/MS m/z: [MH+] | HPLC retention time (min.) | Analytical condition (column) (flow rate; ratio of eluent*) |
|---|---|---|---|
| Aerothricin 39 | 1577 | 13.2 | (C)(9 ml/min.; 55/45) |
| Aerothricin 54 | 1661 | 14.2 | (C)(9 ml/min.; 57/43) |
| Aerothricin 55 | 1689 | 27.8 | (C)(9 ml/min.; 55/45) |
| Aerothricin 77 | 1648 | 25.0 | (C)(9 ml/min.; 53/47) |

*ratio of 0.05% trifluoroacetic acid-water: 0.05% trifluoroacetic acid-acetonitrile

EXAMPLE 10

Preparation of Aerothricin 17

(a). To the solution of the crude nitro derivative of Compound A, obtained in Example 9(a), (55 mg, 0.033 mmol) in MeOH (5 ml) was added 10% palladium on charcoal (20 mg), and the reaction vessel was filled with hydrogen. After being stirred for 13.5 h at room temperature, the mixture was filtered through membrane filter (pore size: 0.2 tim) and the solvent was evaporated to give 52 mg of the crude amino derivative of Aerothricin 3 as brown amorphous, which was used in the next step without further purification.

(b). A mixture of the crude amino derivative of Compound A (described in Reference Example 3), obtained above, (3.4 mg, 0.0021 mmol) and TFA (0.2 ml) was stirred at 0° C. for 30 min. TFA was evaporated under a stream of dry nitrogen. The brown residue was purified by preparative reverse phase HPLC. The appropriate fractions were combined, frozen and lyophilized to give 1.3 mg of Aerothricin 17 as a colorless amorphous solid.

HPLC(Rt): 12.8 min. (column A, flow rate: 1 min./ml, eluent: 0.05% trifluoroacetic acid-water: 0.05% trifluoro-acetic acid-acetonitrile =59:41); FAB-MS (m/z): 1548 [$MH^+$].

The following Aerothricins 29, 56 and 78 were prepared according to the method similar to that described in Example 10, using Aerothricins obtained in Example 9 as the starting material.

| Compound name | FAB-MS m/z: [MH+] | HPLC retention time (min.) | Analytical condition (column) (flow rate; ratio of eluent*) |
|---|---|---|---|
| Aerothricin 29 | 1606 | 31.0 | (C)(9 ml/min.; 60/40) |
| Aerothricin 56 | 1659 | 15.1 | (C)(9 ml/min.; 57/43) |
| Aerothricin 78 | 1618 | 16.8 | (C)(9 ml/min.; 57/43) |

*ratio of 0.05% trifluoroacetic acid-water: 0.05% trifluoroacetic acid-acetonitrile

EXAMPLE 11

Preparation of Aerothricin 18

(a). To a solution of the crude amino derivative of Compound A, obtained in Example 10(a), (1.7 mg, 0.001 mmol) in methanol (0.05 ml) and pyridine (0.025 ml) was added Boc-Gly-OH (18 mg, 0.10 mmol), WSCI (30 mg, 0.15 mmol) and HOBT hydrate (24 mg, 0.15 mmol) successively. After the mixture was stirred for 15 h at room temperature, the solvent was removed by a stream of dry nitrogen.

(b). The crude residue obtained above was dissolved in TFA (0.1 ml) and stirred at 0° C. for 30 min. TFA was removed with a stream of dry nitrogen. The residue was purified by preparative reverse phase HPLC. The appropriate fractions were combined, frozen and lyophilized to give 0.54 mg of Aerothricin 18 as a colorless amorphous solid.

HPLC(Rt): 8.9 min. (column B, flow rate: 4 ml/min., eluent: 0.05% trifluoroacetic acid-water: 0.05% trifluoroacetic acid-acetonitrile =57:43); FAB-MS (m/z): 1605 [$MH^+$].

The following Aerothricins 19–23, 30, 57–62, 79, and 81 were prepared according to the method similar to that described in Example 11 using the corresponding acylating agent and Aerothricins obtained in Example 10 as the starting material.

| Compound name | FAB-MS m/z: [$MH^+$] | HPLC retention time (min.) | Analytical condition (column) (flow rate; ratio of eluent*) |
|---|---|---|---|
| Aerothricin 19 | 1590 | 17.5 | (A)(1 ml/min.; 57/43) |
| Aerothricin 20 | 1619 | 6.0 | (B)(4 ml/min.; 55/45) |
| Aerothricin 21 | 1663 | 18.0 | (C)(9 ml/min.; 60/40) |
| Aerothricin 22 | 1605 | 12.5 | (A)(1 ml/min.; 55/45) |
| Aerothricin 23 | 1620 | 23.9 | (C)(9 ml/min.; 55/45) |
| Aerothricin 30 | 1676 | 24.6 | (C)(9 ml/min.; 61/39) |
| Aerothricin 57 | 1701 | 21.2 | (C)(9 ml/min.; 56/44) |
| Aerothricin 58 | 1730 | 23.4 | (C)(9 ml/min.; 55/45) |
| Aerothricin 59 | 1716 | 13.7 | (C)(9 ml/min.; 58/42) |
| Aerothricin 60 | 1730 | 16.3 | (C)(9 ml/min.; 55/45) |
| Aerothricin 61 | 1730 | 39.1 | (C)(9 ml/min.; 47/53) |
| Aerothricin 62 | 1730 | 15.8 | (C)(9 ml/min.; 55/45) |
| Aerothricin 79 | 1689 | 36.1 | (C)(9 ml/min.; 57/43) |
| Aerothricin 81 | 1675 | 24.4 | (C)(9 ml/min.; 60/40) |

*ratio of 0.05% trifluoroacetic acid-water: 0.05% trifluoroacetic acid-acetonitrile

EXAMPLE 12

Preparation of Aerothricin 12

To a solution of Aerothricin 5 (7.5 mg, 0.0048 mmol), 37% formalin (150 11) and acetic acid (50 $\mu$l) in MeOH (1.0 ml) was added sodium cyanoborohydride (7.5 mg, 0.119 mmol) in MeOH (100 $\mu$l) at room temperature and the mixture was stirred for 7 h at room temperature. After the solvent was evaporated in vacuo, the residue was dissolved in n-butanol and washed with diluted hydrochloric acid and water successively. The organic layer was evaporated in vacuo. The residue was purified by preparative reverse phase HPLC, the detailed condition of which is shown below. The appropriate fractions were combined, frozen and lyophilized to give 5.4 mg of Aerothricin 12 as a colorless amorphous solid.

HPLC(Rt): 7.1 min. (column B, flow rate: 4 ml/min., eluent: 0.05% trifluoroacetic acid-water: 0.05% trifluoroacetic acid-acetonitrile=50:50); FAB-MS (m/z): 1575 [$MH^+$].

The following Aerothricins 13, 25, 30 and 75 were prepared according to the method similar to that described in Example 12.

| Compound name | FAB-MS m/z: [$MH^+$] | HPLC retention time (min.) | Analytical condition (column) (flow rate; ratio of eluent*) |
|---|---|---|---|
| Aerothricin 13 | 1561 | 13.7 | (B)(4 ml/min.; 55/45) |
| Aerothricin 25 | 1607 | 23.5 | (C)(4 ml/min.; 55/45) |
| Aerothricin 30 | 1676 | 24.6 | (C)(9 ml/min.; 61/39) |
| Aerothricin 75 | 1631 | 24.2 | (C)(9 ml/min.; 55/45) |

*ratio of 0.05% trifluoroacetic acid-water: 0.05% trifluoroacetic acid-acetonitrile

EXAMPLE 13

Preparation of Aerothricin 111

(a). To a solution of Aerothricin 3 (500 mg, 0.326 mmol), (2-oxoethyl)-carbamic acid tert-butyl ester* (1.66g, 10.4 mmol) and acetic acid (5 ml) in MeOH (45 ml) was added sodium cyanoborohydride (410 mg, 6.52 mmol) in MeOH (5 ml) at room temperature. The mixture was stirred for 18 h at room temperature. After the solvent was evaporated in vacuo, the residue was dissolved in n-butanol and washed with diluted hydrochloric acid and water successively. The organic layer was evaporated in vacuo.

The crude residue was used for the next step without further purification.

*CAS No. 89711-08-0

(b). A solution of the crude residue obtained above in TFA (20 ml) was stirred at 0° C. for 30 min. TFA was evaporated in vacuo. The residue was purified by preparative reverse HPLC, the detailed condition of which is shown below. The appropriate fraction were combined, frozen and lyophilized to give 253 mg of Aerothricin 111 as a colorless amorphous solid.

HPLC(Rt) 18.6 min. (column F, flow rate: 10 ml/min., eluent: 0.05% trifluoroacetic acid-water: 0.05% trifluoroacetic acid-acetonitrile=57:43); FAB-MS (m/z): 1619 $[M+H]^+$.

The following Aerothricins 100, 112, 114 and 115 were prepared according to the method similar to that described in Example 13.

| Compound name | FAB-MS m/z: [$MH^+$] | HPLC retention time (min.) | Analytical condition (column) (flow rate; ratio of eluent*) |
|---|---|---|---|
| Aerothricin 100 | 1730 | 14.8 | (F)(10 ml/min.; 56/44) |
| Aerothricin 112 | 1647 | 11.8 | (F)(10 ml/min.; 57/43) |
| Aerothricin 114 | 1759 | 23.1 | (C)(10 ml/min.; 60/40) |
| Aerothricin 115 | 1633 | 19.6 | (F)(10 ml/min.; 59/41) |

*ratio of 0.05% trifluoroacetic acid-water: 0.05% trifluoroacetic acid-acetonitrile

EXAMPLE 14

Preparation of Aerothricin 120

To a mixture of Aerothricin 3 (500 mg, 0.326 mmol) and triethylamine (682 $\mu$l, 4.89 mmol) in MeOH (10 ml) was added acrylonitrile (214 $\mu$l, 3.27 mmol) at room temperature. The mixture was stirred for 20 h at room temperature. After the solvent was evaporated in vacuo, the residue was dissolved in n-butanol and washed with diluted hydrochloric acid and water successively. The organic layer was evaporated in vacuo. The crude residue was purified by preparative reverse HPLC, the detailed condition of which is shown below. The appropriate fraction were combined, frozen and lyophilized to give 207 mg of Aerothricin 120 as a colorless amorphous solid.

HPLC(Rt) 27.5 min. (column F, flow rate: 10 ml/min., eluent: 0.05% trifluoroacetic acid-water: 0.05% trifluoroacetic acid-acetonitrile=53:47); FAB-MS (m/z): 1586 $[M+H]^+$.

EXAMPLE 15

Preparation of Aerothricin 113

To a mixture of Aerothricin 120 (100 mg, 0.063 mmol) in MeOH (5 ml) was added 10% palladium on charcoal (20 mg), and the reaction vessel was filled with hydrogen. After being stirred for 20 h at room temperature, the mixture was filtered through membrane filter (pore size: 0.2 $\mu$m) and the solvent was evaporated in vacuo. The crude residue was purified by preparative reverse HPLC, the detailed condition of which is shown below. The appropriate fraction were combined, frozen and lyophilized to give 87.2 mg of Aerothricin 113 as a colorless amorphous solid.

HPLC(Rt) 23.0 min. (column F, flow rate: 10 ml/min., mobile phase: 0.05% trifluoroacetic acid-water: 0.05% trifluoroacetic acid-acetonitrile=57:43); FAB-MS (m/z): 1590 $[M+H]^+$.

Aerothricin 129 was prepared according to the method similar to that described in Example 14–15 followed by removal Boc group of the ornitine residue with trifluoroacetic acid. The starting material, in this case, was the $N^6$-Boc derivative of the (D)-ornitin moiety of Aerothricin 106 obtained in the process similar to Example 16.

| Compound name | FAB-MS m/z: $[MH^+]$ | HPLC retention time (min.) | Analytical condition (column) (flow rate; ratio of eluent*) |
|---|---|---|---|
| Aerothricin 129 | 1705 | 33.8 | (F)(10 ml/min.; 62/38) |

*ratio of 0.05% trifluoroacetic acid-water: 0.05% trifluoroacetic acid-acetonitrile

EXAMPLE 16

Preparation of Aerothricin 14

To a solution of N-Boc-Sarcosine (123 mg, 0.65 mmol), WSC.HCl (240 mg, 1.25 mmol) and DMAP (150 mg, 1.23 mmol) in $CH_3CN$ (10 ml) was added a solution of Aerothricin 3 (100 mg, 0.065 mmol) in $CH_3OH$ (3 ml). The mixture was stirred at room temperature for 15 h and then concentrated in vacuo. The residue was dissolved in n-BuOH (10 ml) and washed with $H_2O$ (5 ml×2, adjusted pH 3~4 with 1 N HCl). The n-BuOH layer was concentrated in vacuo and the residue was dissolved in TFA (5 ml) at 0° C. After the solution was stirred at room temperature for 1 h, TFA was evaporated in vacuo. The residue was purified by preparative reverse phase HPLC to give 40.8 mg (39% yield) of Aerothricin 14 as a white amorphous powder.

HPLC(Rt): 23.1 min. (column C, flow rate: 9 ml/min., 0.05% trifluoroacetic acid-water: 0.05% trifluoroacetic acid-acetonitrile=60:40); FAB-MS (m/z): $1605[MH^+]$.

The following Aerothricins 15, 21, 26–29 and 101–107, 109, 110, 118, 130 and 131 were prepared according to the method similar to that described in Example 16 using the corresponding acid as a building block.

| Compound name | FAB-MS m/z: $[MH^+]$ | HPLC retention time (min.) | Analytical condition (column) (flow rate; ratio of eluent*) |
|---|---|---|---|
| Aerothricin 15 | 1631 | 24.0 | (C)(9 ml/min.; 57/43) |
| Aerothricin 21 | 1663 | 18.0 | (C)(9 ml/min.; 60/40) |
| Aerothricin 26 | 1650 | 19.9 | (C)(9 ml/min.; 50/50) |
| Aerothricin 27 | 1676 | 22.5 | (C)(9 ml/min.; 55/45) |
| Aerothricin 28 | 1636 | 20.9 | (C)(9 ml/min.; 50/50) |
| Aerothricin 29 | 1606 | 31.0 | (C)(9 ml/min.; 60/40) |
| Aerothricin 101 | 1647 | 16.5 | (F)(10 ml/min.; 56/44) |
| Aerothricin 102 | 1661 | 16.3 | (F)(10 ml/min.; 56/44) |
| Aerothricin 103 | 1689 | 13.4 | (F)(10 ml/min.; 54/46) |
| Aerothricin 104 | 1633 | 22.6 | (F)(10 ml/min.; 58/42) |
| Aerothricin 105 | 1619 | 29.2 | (F)(10 ml/min.; 52/38) |
| Aerothricin 106 | 1647 | 17.3 | (F)(10 ml/min.; 56/44) |
| Aerothricin 107 | 1661 | 36.5 | (F)(10 ml/min.; 60/40) |
| Aerothricin 109 | 1633 | 26.1 | (F)(10 ml/min.; 58/42) |
| Aerothricin 110 | 1619 | 28.8 | (F)(9 ml/min.; 58/42) |
| Aerothricin 118 | 1685 | 15.2 | (F)(10 ml/min.; 51/49) |
| Aerothricin 130 | 1847 | 16.0 | (F)(10 ml/min.; 63/37) |
| Aerothricin 131 | 1818 | 21.1 | (F)(10 ml/min.; 63/37) |

*ratio of 0.05% trifluoroacetic acid-water: 0.05% trifluoroacetic acid-acetonitrile

EXAMPLE 17

Preparation of Aerothricin 74

A mixture of Aerothricin 66 (20 mg, 0.012 mmol), 3,5-dimethylpyrazole-1-carboxamidine nitrate (13 mg, 0.064 mmol) and triethylamine (18 ml, 0.13 mmol) in MeOH (1 ml) was stirred at room temperature for 15 h. After solvent was evaporated, the crude residue was purified by preparative reverse phase HPLC, the detailed condition of which is shown below. The appropriate fractions were combined, frozen and lyophilized to give 10.2 mg of Aerothricin 74 as a colorless amorphous solid.

HPLC(Rt) 21.2 min. (column C, flow rate: 9 ml/min., eluent: 0.05% trifluoroacetic acid-water: 0.05% trifluoroacetic acid-acetonitrile=54:46); FAB-MS (m/z): 1645 $[MH^+]$.

The following Aerothricins 4 and 116 were prepared according to the method similar to that described in Example 17 using Aerothricin 3 and 111 as a starting material, respectively.

| Compound name | FAB-MS m/z: $[MH^+]$ | HPLC retention time (min.) | Analytical condition (column) (flow rate; ratio of eluent*) |
|---|---|---|---|
| Aerothricin 4 | 1576 | 7.6 | (D)(1 ml/min.; 50/50) |
| Aerothricin 116 | 1703 | 14.9 | (F)(10 ml/min.; 57/43) |

*ratio of 0.05% trifluoroacetic acid-water: 0.05% trifluoroacetic acid-acetonitrile

EXAMPLE 18

Preparation of Aerothricin 5

(a). To a solution of Compound A, obtained in Reference Example 3, (10 mg, 0.0061 mmol) and potassium carbonate (10 mg, 0.072 mmol) in DMF (1 ml) was added methyl iodide (8 $\mu$l , 0.129 mmol) at room temperature and the mixture was stirred for 43 h at room temperature. After the mixture was filtered by Celite-pad and the filtrate was evaporated in vacuo. The residue was dissolved in n-butanol and washed with diluted hydrochloric acid and water successively. The organic layer was evaporated in vacuo. The crude residue was used for the next step without further purification.

(b). A solution of the crude residue obtained above in TFA (1.0 ml) was stirred at 0° C. for 30 min. TFA was evaporated in vacuo. The residue was purified by preparative reverse phase HPLC, the detailed condition of which is shown below. The appropriate fractions were combined, frozen and lyophilized to give 3.8 mg of Aerothricin 5 as a colorless amorphous solid.

HPLC(Rt): 14.5 min. (column B, flow rate: 4 ml/min., eluent: 0.05% trifluoroacetic acid-water: 0.05% trifluoroacetic acid-acetonitrile=55:45); FAB-MS (m/z): 1547 [$MH^+$].

The following Aerothricins 6–10 and 76 were prepared according to the method similar to that described in Example 18 using the corresponding alkylating agent.

| Compound name | FAB-MS m/z: [$MH^+$] | HPLC retention time (min.) | Analytical condition (column) (flow rate; ratio of eluent*) |
|---|---|---|---|
| Aerothricin 6 | 1561 | 16.0 | (A)(1 ml/min.; 55/45) |
| Aerothricin 7 | 1573 | 8.4 | (A)(1 ml/min.; 50/50) |
| Aerothricin 8 | 1589 | 26.1 | (B)(4.7 ml/min.; 58/42) |
| Aerothricin 9 | 1591 | 38.5 | (B)(4 ml/min.; 60/40) |
| Aerothricin 10 | 1590 | 6.7 | (A)(1 ml/min.; 53/47) |
| Aerothricin 76 | 1617 | 26.0 | (C)(9 ml/min.; 53/47) |

*ratio of 0.05% trifluoroacetic acid-water: 0.05% trifluoroacetic acid-acetonitrile

EXAMPLE 19

Preparation of Aerothricin 24

(a). A cold mixture of Compound A, obtained in Reference Example 3, (100 mg), sodium iodide (29.5 mg, 0.197 mmol) and sodium hypochlorite solution (250 μl) in methanol (2 ml) was stirred at 0° C. for 2 h. The reaction mixture was quenched with saturated aqueous sodium thiosulfate, acidified with 1 N HCl and extracted with n-butanol. The combined organic extracts were evaporated in vacuo. At this point, the starting material was still remained. To complete the iodination reaction, the same experimental procedure was repeated. After the same work up, the residue was purified by preparative reverse phase HPLC to give the iodino derivative of the Compound A as colorless solid (54 mg, 50% yield).

(b). A mixture of the iodido derivative of Compound A obtained above (23.8 mg), methyl acrylate (16 μl), triethylamine (40 μl) and palladium acetate (2.1 mg) in acetonitrile (250 μl) and N,N-dimethylformamide (750 μl) was heated at 70° C. for 28 h. The resulting mixture was passed through C-18 short column and the residue was treated with trifluoroacetic acid (1 ml) at 0° C. for 1 h. The resulting mixture was evaporated in vacuo. Purification of the residue by preparative reverse phase HPLC gave Aerothricin 24 as colorless solid (8.8 mg, 40% yield).

HPLC(Rt): 86.3 min. (column F, flow rate: 9 ml/min., eluent: 0.05% trifluoroacetic acid-water: 0.05% trifluoroacetic acid-acetonitrile=58:42); FAB-MS (m/z): 1617 [$MH^+$].

EXAMPLE 20

Preparation of Aerothricin 96

A mixture of the iodido derivative of the Compound A (30 mg), obtained in Example 19(a), potassium acetate (6.9 mg) and tetrakis(triphenylphoshine)palladium (4.6 mg) in degassed dimethysulfoxide (2 ml) was heated at 60° C. for 20 h under carbon monooxide atmosphere. The resulting mixture was passed through C-18 reverse phase short column and the residue was treated with trifluoroacetic acid at 0° C. for 1 h. The resulting mixture was evaporated under reduced pressure. Purification of the residue by preparative reverse phase HPLC gave Aerothricin 96 as colorless solid (2.3 mg, 8% yield).

HPLC(Rt): 23.2 min. (column F, flow rate: 10 ml/min., eluent: 0.05% trifluoroacetic acid-water: 0.05% trifluoroacetic acid-acetonitrile=52.2:47.8); FAB-MS (m/z): 1677 [$MH^+$].

EXAMPLE 21

Preparation of Aerothricin 32

(a). A mixture of the Compound A, obtained in Reference Example 3, (20 mg) and (methoxycarbonylsulfamoyl) triethylammonium hydroxide (26.5 mg, 0.108 mmol) in acetonitrile (3 ml) was stirred at room temperature for 8 h. The reaction mixture was acidified with 1 N HCl and was evaporated in vacuo. The residue was extracted with n-butanol and the extracts were evaporated in vacuo.

(b). The crude product was treated with trifluoroacetic acid at 0° C. for 1 h. TFA was evaporated in vacuo. Purification of the residue by preparative reverse phase HPLC gave Aerothricin 32 as colorless solid (2.0 mg, 10% yield).

HPLC(Rt): 42.9 min. (column B, flow rate: 4 ml/min., eluent: 0.05% trifluoroacetic acid-water: 0.05% trifluoroacetic acid-acetonitrile=55:45); FAB-MS (m/z): 1516 [$MH^+$].

EXAMPLE 22

Preparation of Aerothricin 31

(a). To a cold solution of the Compound A, obtained in Reference Example 3, (25.7 mg) in tetrahydrofurane (5 ml) was added borane-dimethylsulfide complex (25 ml) at −10 ° C. After being stirred at −10° C. for 5 h, the reaction mixture was quenched with 2 N HCl and was extracted with n-butanol. The combined extracts were evaporated in vacuo.

(b). The crude product was treated with trifluoroacetic acid at 0° C. for 1 h. THF was evaporated under reduced pressure. Purification of the residue by preparative reverse phase HPLC gave Aerothricin 31 as colorless solid (3.7 mg, 15% yield).

HPLC(Rt): 25.1 min. (column B, flow rate: 4 ml/min., eluent: 0.05% trifluoroacetic acid-water: 0.05% trifluoroacetic acid-acetonitrile=62:38); FAB-MS (m/z): 1519 [$MH^+$].

EXAMPLE 23

Preparation of Aerothricin 121

To a solution of Aerothricin 3 (50 mg) in DMF(l ml) and triethylamine (0.025 ml) was added methyl iodide (0.010 ml). After being stirred for 16 h at room temperature, to the mixture was further added triethylamine (0.025 ml) and methyl iodide (0.05 ml) and stirred for 24 h at room temperature. LCMS analysis of the mixture indicated >90% conversion to the desired compound. The solvent was purged with a stream of nitrogen and the residue was purified by preparative reverse phase HPLC, the detailed condition of which is shown below. The appropriate fractions were combined, frozen and lyophilized to give 23 mg of Aerothricin 121, as a colorless amorphous solid.

HPLC(Rt): 20.5 min. (column B, flow rate: 4 ml/min., eluent: 0.05% trifluoroacetic acid-water: 0.05% trifluoroacetic acid-acetonitrile=52:48); FAB-MS (m/z): 1576[$M^+$].

EXAMPLE 24

Preparation of Aerothricin 122

To a solution of Aerothricin 3 (50 mg) in pyridine(1 ml) was added sulfur trioxide N,N-dimethylformamide complex (23 mg). After being stirred for 2 h at room temperature, the solvent was purged with a stream of dry nitrogen.

A solution of the crude residue obtained above in TFA (1 ml) was stirred at 0° C. for 30 min. TFA was purged with a stream of dry nitrogen and the residue was purified by preparative reverse phase HPLC, the detailed condition of which is shown below. The pure fractions were combined, frozen and lyophilized to give 5 mg of Aerothricin 122, as a colorless amorphous solid.

HPLC(Rt): 24.6 min. (column F, flow rate: 10 ml/min., eluent: 0.05% trifluoroacetic acid-water: 0.05% trifluoroacetic acid-acetonitrile=52:48); FAB-MS (m/z): 1613 [$MH^+$].

EXAMPLE 25

Preparation of Aerothricin 63

(a). To a stirred solution of $N^\alpha$-Fmoc-$N^\beta$-Boc(S)2,3-diaminopropionic acid (343 mg, 0.80 mmol) in DMF (10 ml) were added BOP reagent (355 mg, 0.80 mmol), HOBT hydrate (.24 mg, 0.81 mmol) and NN-diisopropylethylamine (0.174 ml, 1.00 mmol). After the mixture was stirred for 1.5 h at room temperature, a solution of Aerothricin 3 (1.10 g, 0.67 mmol) and N,N-diisopropylethylamine (0.174 ml, 1.00 mmol) in DMF (9.5 ml) was added to the mixture. After being stirred for additional 1 h at room temperature, the mixture was concentrated in vacuo.

(b). To a stirred solution of the residue obtained above in DMF (20 ml) was added piperidine-4-carboxylic acid polyamine resin (200–400 mesh),HL (1.50 mmol/g, 2.66 g), and the reaction mixture was irradiated with ultrasonic sound for 6 h. The resin was removed by filtration through a Celite pad, washed with MeOH and the combined filtrate and washing were frozen and lyophilized to give 1.08 g of the crude derivative of Aerothricin 3 as a white amorphous solid, which was used for the next step without further purification.

(c). To a stirred solution of the crude derivative of Aerothricin 3, obtained above, (25.6 mg, 0.015 mmol) in MeOH (1 ml) were added (2-oxo-ethyl)carbamic acid tert-butyl ester (crude, 207 mg), AcOH (0.1 ml) and $NaBH_3CN$ (19.1 mg). After the mixture was stirred for 2 h at room temperature, the reaction mixture was concentrated in vacuo. The residue was diluted with n-BuOH (4 ml) and washed with $H_2O$ (1 ml×2, adjusted pH 3–4 with 0.1 N HCl). The n-BuOH layer was concentrated in vacuo. The crude residue was used for the next step without further purification.

(d). A solution of the crude residue obtained above in TFA (2 ml) was stirred at 0° C. for 2 h. TFA was evaporated in vacuo and the residue was purified by preparative reverse phase HPLC, the detailed condition of which is shown below. The pure fractions were combined, frozen and lyophilized to give 8.8 mg of Aerothricin 63 as a white amorphous solid.

HPLC(Rt): 24.8 min. (column F, flow rate: 9 ml/min., eluent: 0.05% trifluoroacetic acid-water: 0.05% trifluoroacetic acid-acetonitrile 54:36); FAB-MS(m/z): 1706 [$MH^+$].

EXAMPLE 26

Preparation of Aerothricin 127

Aerothricin 127 was prepared by the same method as that described for Aerothricin 63 by use of $N^\alpha$-Fmoc-$N^\delta$-Boc-(D)-ornitin. Aerothricin 127 was obtained as a white amorphous solid.

HPLC(Rt): 23.9 min. (column F, flow rate: 9 ml/min., eluent: 0.05% trifluoroacetic acid-water: 0.05% trifluoroacetic acid-acetonitrile=54:36); FAB-MS(m/z): 1734 [$MH^+$].

EXAMPLE 27

Preparation of Aerothricin 124

(a). To a stirred solution of Boc-D-Orn(Boc)-OH (46 mg, 0.138 mmol) in DMF (2 ml) were added BOP reagent (62 mg, 0.14 mmol), HOBT hydrate (22 mg, 0.144 mmol) and N,N-diisopropylethylamine (24 pl, 0.138 mmol ). After being stirred for 30 min. at room temperature, a solution of Aerothricin 120 (100 mg, 0.063 mmol) and N-diisopropylethylamine (24 pl, 0.138 mmol ) in DMF (2 ml) was added to the reaction mixture. After being stirred for 18 h at room temperature, the solvent was evaporated in vacuo.

The residue was dissolved in TFA (4 ml), and the solution was stirred at 0° C. for 30 min. After removal of TFA with a stream of dry nitrogen, the residue was purified by preparative reverse phase HPLC, the detailed condition of which is shown below. The pure fractions were combined, frozen and lyophilized to give 48.6 mg of the nitrile derivative as a white amorphous solid.

HPLC(Rt): 20.2 min. (column F, flow rate: 10 ml/min., eluent: 0.05% trifluoroacetic acid-water: 0.05% trifluoroacetic acid-acetonitrile=57:43); FAB-MS (m/z): 1700 $[M+H]^+$.

(b). To a mixture of the nitrile derivative obtained above (48.6 mg, 0.0286 mmol) in dioxane (1 ml) and water (1 ml) was added 10% palladium on charcoal (10 mg), and the mixture was stirred under hydrogen atmosphere for 14 h at room temperature. Then the mixture was filtered through membrane filter (pore size: 0.2 $\mu$m) and the solvent was evaporated in vacuo. The crude residue was purified by preparative reverse phase HPLC, the detailed condition of which is shown below. The pure fractions were combined, frozen and lyophilized to give 26.5 mg of Aerothricin 124 as a colorless amorphous solid.

HPLC(Rt): 18.2 min. (column F, flow rate: 10 ml/min., eluent: 0.05% trifluoroacetic acid-water: 0.05% trifluoroacetic acid-acetonitrile=60:40); FAB-MS (m/z): 1704 $[M+H]^+$.

EXAMPLE 28

Preparation of Aerothricin 125

(a). To a solution of Aerothricin 3 mono TFA salt (natural product: 50 mg) in DMF(1 ml) and triethylamine(0.126 ml) was added 2-bromo-5-nitropyridine(185 mg). After being stirred for 25 h at room temperature, the solvent was purged with a stream of dry nitrogen. The residue was purified by preparative reverse phase HPLC. The appropriate fractions were combined, frozen and lyophilized to give 25 mg of 5-nitropyrid-2-yl derivative of Aerothricin 3 as a slight yellow amorphous solid.

HPLC(Rt): 29.9 min. (column F, flow rate: 10 ml/min., eluent: 0.05% trifluoroacetic acid-water: 0.05% trifluoroacetic acid-acetonitrile=47:53); FAB-MS (m/z): 1655 $[M+H]^+$.

(b). 5-Nitropyrid-2-yl derivative of Aerothricin 3 obtained above (10 mg) was dissolved in dioxane-$H_2O$ (1 ml–5 ml).

5% Palladium on charcoal (20 mg) was added and the reaction vessel was filled with hydrogen. After being stirred for 3 h at room temperature, filtration through membrane filter (pore size: 0.2 μm) and evaporation of solvent gave 14 mg of crude product, which was purified by preparative reverse phase HPLC, the detailed condition of which is shown below. The pure fractions were combined, frozen and lyophilized to give 2.5 mg of Aerothricin 125 as a colorless amorphous solid.

HPLC(Rt): 18.7 min. (column F, flow rate: 10 ml/min., eluent: 0.05% trifluoroacetic acid-water: 0.05% trifluoroacetic acid-acetonitrile=52:48); FAB-MS (m/z): 1625 $[M+H]^+$.

EXAMPLE 29

Preparation of Aerothricin 128

(a). To a stirred solution of Fmoc-D-Orn(Boc)-OH (389 mg, 0.86 mmol) in DMF (10 ml) were added BOP reagent (378 mg, 0.85 mmol), HOBT hydrate (131 mg, 0.86 mmol) and N,N-diisopropylethylamine (171 tl, 0.98 mmol). After the mixture was stirred at a room temperature for 40 min., a solution of Aerothricin 3 (1.08 g, 0.66 mmol) and N,N-diisopropylethylamine (171 μl, 0.98 mmol) in DMF (10 ml) was added to the mixture. After being stirred for 2.5 h at a room temperature, piperidine (4 ml) was added, and the mixture was stirred for additional 1 h at a room temperature. The mixture was concentrated in vacuo. The residue was diluted with n-BuOH (50 ml) and washed with $H_2O$ (25 ml×2, adjusted pH 3 with 1 N HCl). The n-BuOH layer was concentrated in vacuo.

(b). To a stirred solution of Boc-D-Orn(Boc)-OH (9.6 mg, 0.029 mmol) in DMF (1 ml) were added BOP reagent (13.3 mg, 0.030 mmol), HOBT hydrate (4.6 mg, 0.030 mmol) and N,N-diisopropylethylamine (4.8 μl, 0.028 mmol). After the mixture was stirred at room temperature for 30 min., a solution of the crude residue (31.9 mg) obtained above and N,N-diisopropylethylamine (4.8 μl, 0.028 mmol) in DMF (1 ml) was added to the mixture. After being stirred for 4 h at a room temperature, the reaction mixture was concentrated in vacuo.

(c). The crude residue obtained above was dissolved in TFA (1.5 ml) and stirred at 0° C. for 1 h. The reaction mixture was concentrated in vacuo, and the residue was purified by preparative reverse HPLC. The appropriate fraction were combined, frozen and lyophilized to give 16.6 mg of Aerothricin 128 as a white amorphous solid:

HPLC(Rt): 27.23 min. (column F, flow rate: 9 ml/min., eluent: 0.05% trifluoroacetic acid-water: 0.05% trifluoroacetic acid-acetonitrile=55:35); FAB-MS (m/z): 1762 $[MH^+]$.

EXAMPLE 30

Preparation of Aerothricin 106 from the Compound (IX)

(a). A mixture of Fmoc-Tyr($Bu^t$) (21 mg, 0.0457 mmol), HOBt mono hydrate (6.6 mg, 0.0431 mmol), BOP reagent (18.8 mg, 0.0424 mmol) and diisopropylethylamine (DIEA, 20 μl) in DMF (0.5 ml) was stirred at room temperature for 1 h and then was added to a mixture of N(orn)-Boc-IX (19.3 mg, 0.0131 mmol) obtained in Example 6 and DIEA (10 μl) in DMF (1 ml). After stirring at room temperature for 3 h, the resulting mixture was treated with piperidine (0.375 ml) for 1 h and then was concentrated in vacuo. The residue was washed with dichloromethane and diethylether to remove the reagents. Purification of the residue by HPLC gave the desired linear peptide A as a white solid (16.6 mg).

HPLC (Rt) 19 min. (column: Soken-ODS / 20×250 mm, flow rate: 9 ml/min., eluent $H_2O$: $CH_3CN$=gradient, 1% AcOH).

(b). A mixture of Fmoc-D-Ala mono hydrate (1.2 mg, 0.034 mmol), HOBt mono hydrate (4.7 mg, 0.031 mmol), BOP reagent (13.6 mg, 0.031 mmol) and DIEA (8 PL) in DMF (0.5 ml) was stirred at room temperature for 1 h and then was added to a mixture of the linear peptide A obtained above (16.6 mg, 0.0098 mmol) and DIEA (6 μl) in DMF (1 ml). The reaction mixture was stirred at room temperature and the activated ester was added until the almost starting material was consumed. The resulting mixture was concentrated in vacuo. The residue was washed with dichloromethane and diethylether to remove the reagents. The crude product was treated with trifluoroacetic acid at 0C for I h. The mixture was concentrated under reduced pressure. Purification of the residue by HPLC gave the desired linear peptide B as a white solid (6.1 mg).

HPLC(Rt) 19 min. (column: Soken-ODS/20×250 mm, flow rate: 9 ml/min., eluent: $H_2O$: $CH_3CN$=gradient, 1% AcOH).

(c). A mixture of Boc-D-Om($Bu^t$) (5.7 mg, 0.017 mmol), HOBt mono hydrate (2.3 mg, 0.015 mmol), BOP reagent (5.4 mg, 0.012 mmol) and DIEA (6 μl,) in DMF (0.5 ml) was stirred at room temperature for 1 h and then was added to a mixture of the linear peptide B (6.1 mg, 0.0033 mmol) and DIEA (3 μl) in DMF (1 ml). After stirring at room temperature for 2 h, the resulting mixture was treated with piperidine (0.375 ml) for 1 h. and was concentrated in vacuo. Purification of the residue by HPLC gave linear peptide C as a white solid (4.1 mg).

HPLC(Rt) 16.7 min. (column: Soken-ODS /20×250 mm, flow rate: 9 ml/min., eluent $H_2O$: $CH_3CN$=gradient, 1% AcOH).

(d). The linear peptide C was acidified with 0.01 N hydrochloride and was extracted with n-butanol. The butanol extract was concentrated in vacuo. The extract was dissolved into DMF (2 ml). Then HOBt mono hydrate (0.1 M in DMF, 60 μl), BOP reagent (0.1 M in DMF, 60 μl) and DIEA (2 μl) were added to the mixture. After stirring at room temperature for 1 h, the resulting mixture was concentrated in vacuo. The residue was treated with trifluoroacetic acid at 0° C. for 1 h. The mixture was concentrated under reduced pressure. Purification of the residue by HPLC gave Aerothricin 106 as a white solid (2.2 mg, 9% from N(orn)-Boc-IX).

The analytical data is described in the table of Example 16.

EXAMPLE A

Injectable solutions each containing the following ingredients were manufactured in the conventional manner per se:

| | |
|---|---|
| Aerothricin 45 | 20 mg |
| di-Sodium hydrogenphosphate, anhydrous | 7.6 mg |
| Sodium diphosphate dihydrate | 2.0 mg |
| Ethyl alcohol | 150 mg |
| Distilled water, deionized, sterile | 850 mg |
| Total | 1029.6 mg |

What is claimed is:

1. A compound of the formula (I)

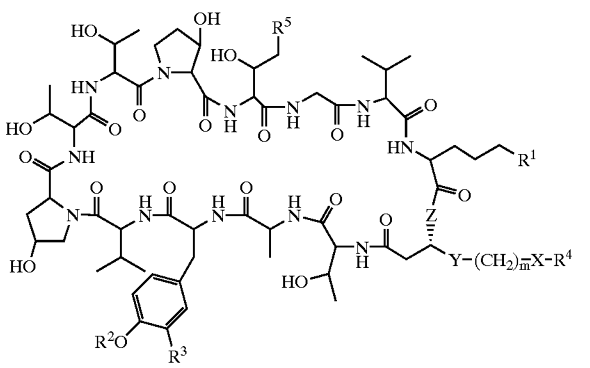

wherein $R^1$ is guanidino, tri-lower alkylammonio, $-N(R^{10})-R^{11}$, $-N(R^{15})-CO-R^{14}$, $-N(R^{15})-CO-CH[N(R^{10})R^{11}]-R^{13}$, $-NHCOCH(R^{13})-NHCOCH(NH_2)-R^{13}$,

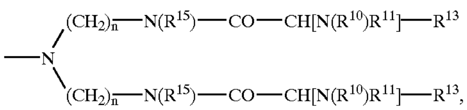

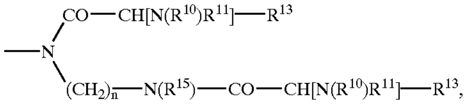

or

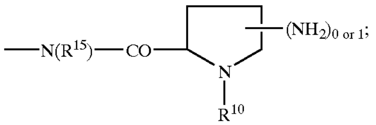

;

$R^{10}$ and $R^{11}$ are each independently selected from hydrogen; heteroaryl substituted with one or two amino; lower alkyl optionally substituted with one or more amino, amino-lower alkyl, cyano, guanidino, nitrogen containing heterocycle(s) or phenyl group(s) containing an amino, amidino or guanidino group;

$R^{13}$ is a residue derived from natural or unnatural amino acids;

$R^{14}$ is lower alkyl substituted with one or more amino, guanidino, nitrogen containing heterocycle(s) or phenyl group(s) containing an amino, amidino or guanidino group;

$R^{15}$ is hydrogen, lower alkyl optionally substituted with one or more amino, guanidino, nitrogen containing heterocycle(s) or phenyl group(s) containing an amino, amidino or guanidino group;

$R^2$ is hydrogen, hydroxysulfonyl, lower alkyl or lower alkenyl, wherein lower alkyl and lower alkenyl optionally substituted with acyl, carbamoyl, amino, mono-lower alkylamino or di-lower alkylamino;

$R^3$ is hydrogen, hydroxy, nitro, amino, acylamino, (lower alkylcarbamoyl)amino, carboxyl, lower alkoxy, lower alkoxycarbonyl, lower alkyl, lower alkenyl or lower alkynyl, wherein lower alkyl, lower alkenyl and lower alkynyl is optionally substituted with hydroxy, amino, mono-lower alkylamino, di-lower alkylamino, lower alkoxycarbonyl or carbamoyl;

$R^4$ is alkyl, alkenyl, alkoxy or alkenyloxy which is optionally substituted with lower alkyl, aryl, cycloalkyl or fluorine atom(s);

$R^5$ is $-CONH_2$, $-CN$ or $-CH_2NH_2$;

X is a single bond, or an aryl, biphenyl or terphenyl group optionally containing one or more hetero atom(s) and/or being substituted with halogen atom(s) or lower alkyl;

Y is a single bond, $-CH_2-$, $-CH(\text{lower alkyl})-$, $-CONH-$ or $-CON(\text{lower alkyl})-$;

Z is $-O-$, $-NH-$ or $-N(\text{lower alkyl})-$;

m is an integer of 0 to 4; and n is an integer of 2 to 5;

with the proviso that when $-Y-(CH_2)m-X-R^4$ is alkyl or aralkyl, then $R^1$ is not amino, $R^2$ and $R^3$ are not hydrogen, $R^5$ is not $-CONH_2$, and Z is not $-O-$ or $-NH-$ at the same time;

or a pharmaceutically acceptable salt thereof.

2. The compound of claim 1 wherein $R^1$ is $-N(R^{10})-R^{11}$, with $R^{10}$ and $R^{11}$ as defined in claim 1.

3. The compound of claim 1 wherein $R^1$ is $-N(R^{15})-CO-CH[N(R^{10})R^{11}]-R^{13}$, with $R^{10}$, $R^{11}$, $R^{13}$ and $R^{15}$ as defined in claim 1.

4. The compound of claim 1 wherein $R^1$ is $-NHCOCH(R^{13})-NHCOCH(NH_2)-R^{13}$, with $R^{13}$ defined in claim 1.

5. The compound of claim 1 wherein $R^1$ is

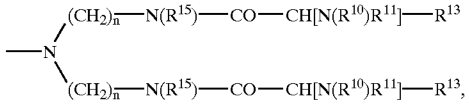

with $R^{10}$, $R^{11}$, $R^{13}$, $R^{15}$ and n as defined in claim 1.

6. The compound of claim 1 wherein $R^1$ is

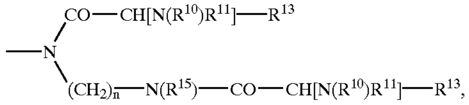

with $R^{10}$, $R^{11}$, $R^{13}$, $R^{15}$ and n as defined in claim 1.

7. The compound of claim 1 wherein $R^1$ is $-N(R^{15})-CO-R^{14}$, with $R^{14}$ and $R^{15}$ as defined in claim 1.

8. The compound of claim 1 wherein $R^1$ is

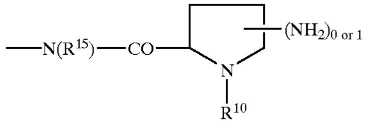

with $R^{10}$ and $R^{15}$ as defined in claim 1.

9. The compound of claim 1 wherein $R^1$ is amino or guanidino.

10. The compound of claim 1 wherein $R^2$ is hydrogen, hydroxysulfonyl or lower alkyl.

11. The compound of claim 3 wherein $R^2$ is hydrogen, hydroxysulfonyl or lower alkyl.

12. The compound of claim 1 wherein $R^3$ is hydrogen, hydroxy, nitro, amino or acylamino.

13. The compound of claim 3 wherein $R^3$ is hydrogen, hydroxy, nitro, amino or acylamino.

14. The compound of claim 11 wherein $R^3$ is hydrogen, hydroxy, nitro, amino or acylamino.

15. The compound of claim 1 wherein $R^3$ is (lower alkylcarbamoyl)amino, carboxyl, lower alkoxy or lower alkoxycarbonyl.

16. The compound of claim 3 wherein $R^3$ is (lower alkylcarbamoyl)amino, carboxyl, lower alkoxy or lower alkoxycarbonyl.

17. The compound of claim 11 wherein $R^3$ is (lower alkylcarbamoyl)amino, carboxyl, lower alkoxy or lower alkoxycarbonyl.

18. The compound of claim 1 wherein $R^5$ is $—CONH_2$ or $—CH_2NH_2$.

19. The compound of claim 3 wherein $R^5$ is $—CONH_2$ or $—CH_2NH_2$.

20. The compound of claim 14 wherein $R^5$ is $—CONH_2$ or $—CH_2NH_2$.

21. The compound of claim 17 wherein $R^5$ is $—CONH_2$ or $—CH_2NH_2$.

22. The compound of claim 1 wherein X is a single bond or one of the following radicals:

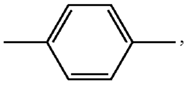,
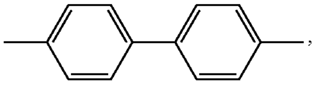,
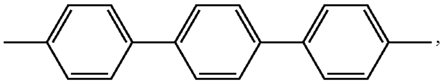,
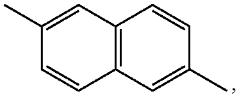,
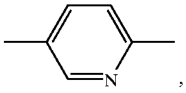,
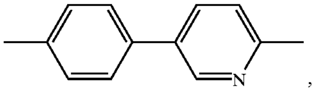,
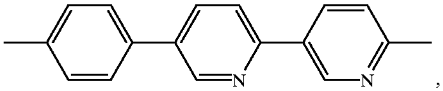,
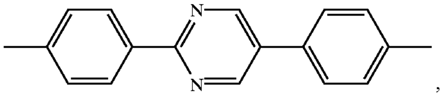,
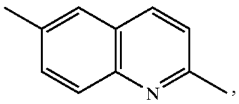,
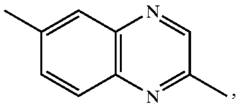,
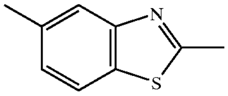,
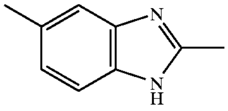,
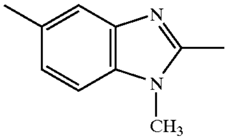,
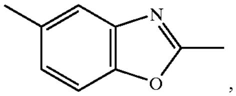,
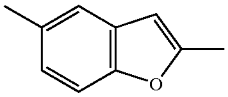,
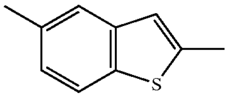 or
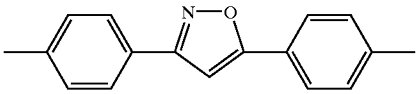

which may be further substituted with halogen atom(s) or lower alkyl.

23. The compound of claim 3 wherein X is a single bond or one of the following radicals:

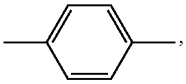,
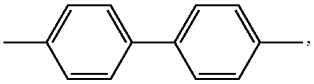,
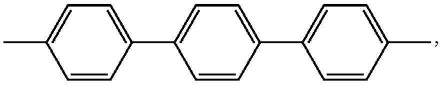,
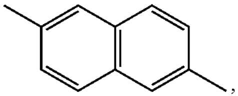,
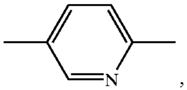,
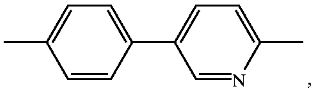,
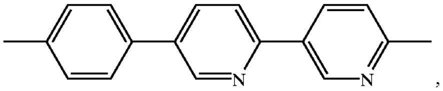,
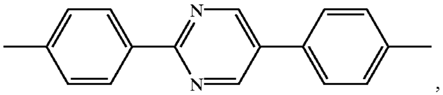,
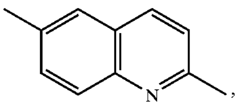,
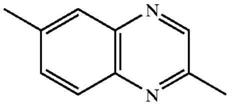,
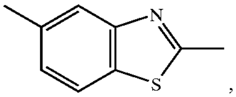,
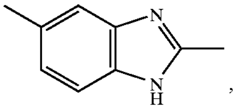,
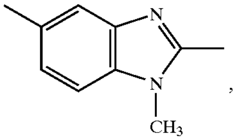,
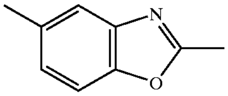,
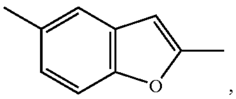,
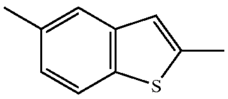 or
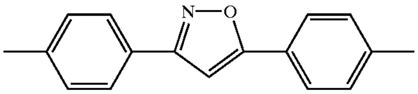

which may be further substituted with halogen atom(s) or lower alkyl.

24. The compound of claim 20 wherein X is a single bond or one of the following radicals:

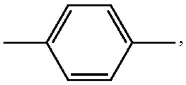,
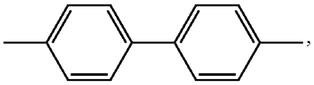,
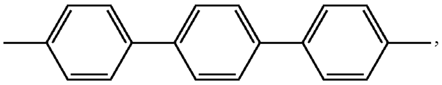,
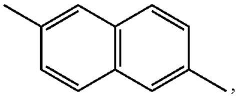,
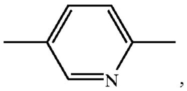,
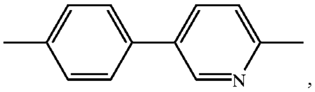,

-continued

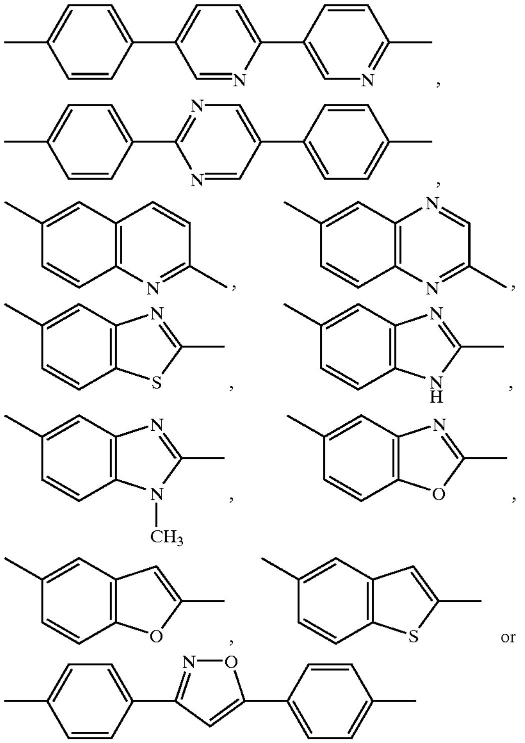

or which may be further substituted with halogen atom(s) or lower alkyl.

25. The compound of claim 21 wherein X is a single bond or one of the following radicals:

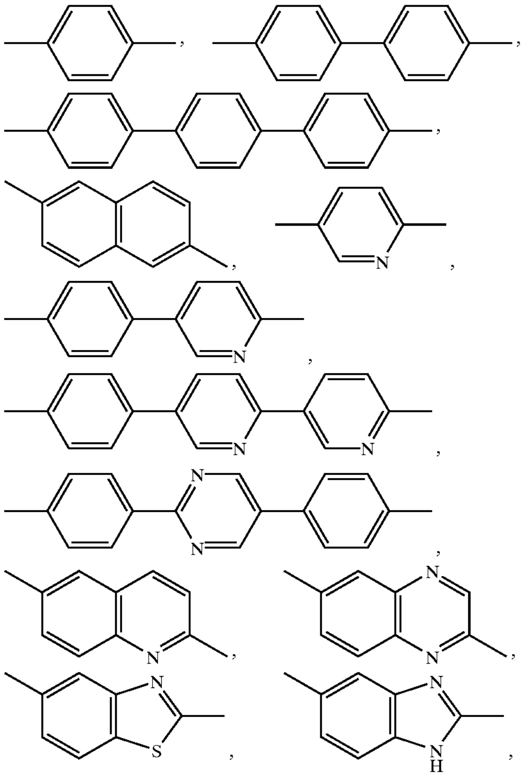

-continued

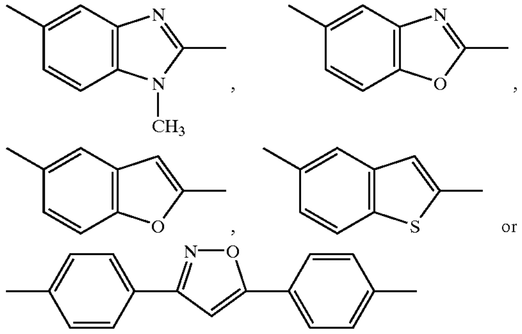

or which may be further substituted with halogen atom(s) or lower alkyl.

26. The compound of claim 1 wherein X is a single bond, phenyl, biphenyl or naphthyl which may be further substituted with halogen atom(s) or lower alkyl.

27. The compound of claim 3 wherein X is a single bond, phenyl, biphenyl or naphthyl which may be further substituted with halogen atom(s) or lower alkyl.

28. The compound of claim 24 wherein X is a single bond, phenyl, biphenyl or naphthyl which may be further substituted with halogen atom(s) or lower alkyl.

29. The compound of claim 25 wherein X is a single bond, phenyl, biphenyl or naphthyl which may be further substituted with halogen atom(s) or lower alkyl.

30. The compound of claim 1 wherein $R^4$ is alkyl or alkoxy which may be optionally substituted with lower alkyl, aryl, cycloalkyl or fluorine atom(s).

31. The compound of claim 3 wherein $R^4$ is alkyl or alkoxy which may be optionally substituted with lower alkyl, aryl, cycloalkyl or fluorine atom(s).

32. The compound of claim 28 wherein $R^4$ is alkyl or alkoxy which may be optionally substituted with lower alkyl, aryl, cycloalkyl or fluorine atom(s).

33. The compound of claim 29 wherein $R^4$ is alkyl or alkoxy which may be optionally substituted with lower alkyl, aryl, cycloalkyl or fluorine atom(s).

34. The compound of claim 1 wherein m is an integer of 0 to 2.

35. The compound of claim 3 wherein m is an integer of 0 to 2.

36. The compound of claim 32 wherein m is an integer of 0 to 2.

37. The compound of claim 33 wherein m is an integer of 0 to 2.

38. The compound of claim 1 wherein Y is —$CH(CH_3)$—, —$CON(CH_3)$—, —CONH—, —$CH_2$— or a single bond.

39. The compound of claim 3 wherein Y is —$CH(CH_3)$—, —$CON(CH_3)$—, —CONH—, —$CH_2$— or a single bond.

40. The compound of claim 36 wherein Y is —$CH(CH_3)$—, —$CON(CH_3)$—, —CONH—, —$CH_2$— or a single bond.

41. The compound of claim 37 wherein Y is —$CH(CH_3)$—, —$CON(CH_3)$—, —CONH—, —$CH_2$— or a single bond.

42. The compound of claim 1 wherein Z is —NH—.

43. The compound of claim 3 wherein Z is —NH—.

44. The compound of claim 40 wherein Z is —NH—.

45. The compound of claim 41 wherein Z is —NH—.

46. The compound of claim 1 wherein Z is —O—.

47. The compound of claim 3 wherein Z is —O—.

48. The compound of claim 40 wherein Z is —O—.

49. The compound of claim 41 wherein Z is —O—.

50. The compound of claim 1 wherein $R^1$ is amino, $R^2$ and $R^3$ are hydrogen, $R^5$ is $—CH_2NH_2$, Z is oxygen and $—Y—(CH_2)_m—X—R^4$ is $—(CH_2)_{12}CH_3$.

51. A composition comprising a compound of claim 1, or a pharmaceutically acceptable salt thereof, together with a pharmaceutically acceptable carrier.

* * * * *

UNITED STATES PATENT AND TRADEMARK OFFICE
CERTIFICATE OF CORRECTION

PATENT NO. : 6,489,440 B1
DATED : December 3, 2002
INVENTOR(S) : Masahiro Aoki et al.

It is certified that error appears in the above-identified patent and that said Letters Patent is hereby corrected as shown below:

Title page,
Item [57], ABSTRACT, replace Formula (I) with:

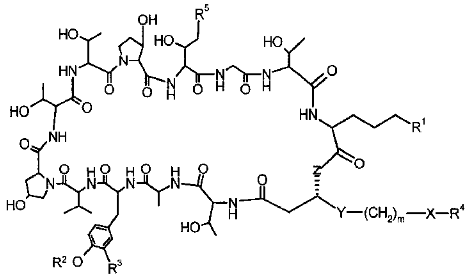

(I)

Column 1,
Lines 40-57 summary of the Invention, replace Formula (I) with:

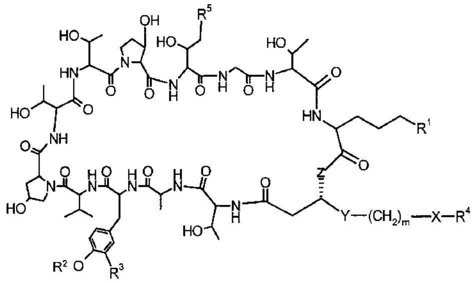

(I)

UNITED STATES PATENT AND TRADEMARK OFFICE

CERTIFICATE OF CORRECTION

PATENT NO. : 6,489,440 B1 Page 2 of 2
DATED : December 3, 2002
INVENTOR(S) : Masahiro Aoki et al.

It is certified that error appears in the above-identified patent and that said Letters Patent is hereby corrected as shown below:

Column 103,
Lines 5-21, replace Formula (I) with

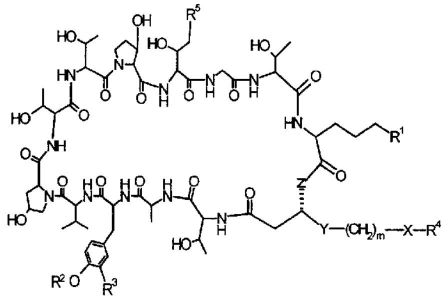

(I)

Signed and Sealed this

Seventeenth Day of June, 2003

JAMES E. ROGAN
*Director of the United States Patent and Trademark Office*